United States Patent [19]
Reitz et al.

[11] Patent Number: 5,663,180
[45] Date of Patent: *Sep. 2, 1997

[54] SUBSTITUTED CYCLOPENTENES FOR THE TREATMENT OF INFLAMMATION

[75] Inventors: David B. Reitz; Jinglin Li, both of Chesterfield, Mo.

[73] Assignee: G.D. Searle & Co., Skokie, Ill.

[ * ] Notice: The term of this patent shall not extend beyond the expiration date of Pat. No. 5,344,991.

[21] Appl. No.: 276,006

[22] Filed: Jul. 15, 1994

Related U.S. Application Data

[63] Continuation-in-part of Ser. No. 146,359, Oct. 29, 1983, Pat. No. 5,344,911.

[51] Int. Cl.$^6$ .................................................. A01N 43/42
[52] U.S. Cl. .................. 514/299; 514/678; 514/680; 514/684; 514/825; 514/916; 514/602; 514/709; 546/184; 546/192; 546/195; 546/203; 564/426; 564/427; 564/84; 568/34
[58] Field of Search .................................. 514/602, 678, 514/702, 680, 684, 825, 918; 564/84, 426, 427; 546/184, 192, 195, 203; 568/34

[56] References Cited

U.S. PATENT DOCUMENTS

| | | | |
|---|---|---|---|
| 4,229,207 | 10/1980 | Laanio et al. | 71/107 |
| 4,543,207 | 9/1985 | Sato et al. | 252/570 |
| 5,474,995 | 12/1995 | Ducharme et al. | 514/241 |

FOREIGN PATENT DOCUMENTS

| | | |
|---|---|---|
| 0 142 801 | 5/1985 | European Pat. Off. . |
| 4212628A1 | 4/1992 | Germany . |
| 95/00501 | 1/1995 | WIPO . |

OTHER PUBLICATIONS

T. Hla et al, Proc. Natl. Acad. Sci. USA, 89, 7384 (1992).
J. Masferrer et al., Proc. Natl. Acad. Sci, USA, 89, 3917 (1992).
E. Meade et al, J. Biol. Chem., 268, 6610 (1993).
Futaki et al, Prostaglandins, 47, 55 (1994).
E.J. Corey et al., J. Amer. Chem. Soc., 85, 1788–1792, (1963).
H. Ohash et al., Phytochemistry, 31,1317 (1992).
D. Y. Curtin et al, J. Org. Chem, 36, 565–72, (1971).
O.P. Malik et al, Ind. J. Chem., 14B, 975–78, (1976).
Somers et al, J. Photochem. Photobio., 48A, 353–74, (1989).
W.H. Laarhoven, Pure & Appl. Chem., 56, 1225–40, (1984).

*Primary Examiner*—Deborah D. Carr
*Attorney, Agent, or Firm*—Joseph W. Bulock

[57] ABSTRACT

A class of 1,2-diarylcyclopentenyl compounds is described for use in treating inflammation and inflammation-related disorders. Compounds of particular interest are defined by Formula III:

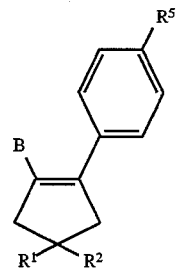

wherein each of $R^1$ and $R^2$ is independently selected from alkyl, hydrido, hydroxyalkyl, halo, haloalkyl, alkoxycarbonyl and carboxyl; wherein $R^5$ is selected from alkylsulfonyl, haloalkylsulfonyl and sulfamyl; and wherein B is phenyl or pyridyl, wherein B is optionally substituted at a substitutable position with alkyl, halo, alkylthio, cyano, haloalkyl, alkoxy, hydroxyalkyl and alkoxyalkyl; or a pharmaceutically-acceptable salt thereof.

37 Claims, No Drawings

SUBSTITUTED CYCLOPENTENES FOR THE TREATMENT OF INFLAMMATION

RELATED CASE

This is a continuation-in-part application of U.S. patent application Ser. No. 08/146,359, U.S. Pat. No. 5,344,991, with a filing date of Oct. 29, 1993.

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, Proc. Natl. Acad. Sci, USA, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, Proc. Natl. Acad. Sci, USA, 89, 3917 (1992)). The 6-methoxy-2-napthylacetic acid metabolite of nabumetone has been found by E. Meade et al to selectively inhibit the COX II enzyme (J. Biol. Chem., 268, 6610 (1993)). In addition, Futaki et al (Prostaglandins, 47, 55 (1994)) have reported that N-(2-cyclohexyloxy-4-nitrophenyl)methanesulfonamide inhibits the COX II enzyme.

The cyclopentene compounds disclosed herein are such safe and also effective antiinflammatory agents furthering such efforts. The invention compounds are found to show usefulness in vivo as antiinflammatory agents with minimal side effects. The substituted cyclopentene compounds disclosed herein preferably selectively inhibit cyclooxygenase II over cyclooxygenase I.

1,2-Diarylcycloalkenes have been made and used for a variety of utilities. For example, U.S. Pat. No. 4,543,207 to Sato, et al., describes diphenyl cyclohexene as an electrical insulating oil additive.

U.S. Pat. No. 4,229,207, to Laanio, et al., describes 1,2-diphenyl-cyclohex-1-ene-4-carboxylic acid esters, specifically, 1,2-di(4-phenylsulfonic acid)cyclohex-1-ene-4-carboxylic acid ethyl ester. These ester compounds are reported to be effective as plant growth regulating agents and as post-emergent herbicides for controlling wild oats.

DE 4,212,628, published Oct. 21, 1993, describes 3,4-bis-alkylphenylcyclohex-3-enes as anti-tumor agents.

The synthesis of 3,4-diphenyl-$\Delta^3$-cyclopentenone ethylene ketal is described as an intermediate for forming carbinols [E. J. Corey, et al., J. Amer. Chem. Soc., 85, 1788 (1963)]. 2,3-Bis-(4-hydroxyphenyl)-2-cyclopenten-1-one has been identified from the knot resin powder of Arqaucaria angustifolia [H. Ohash, et al., Phytochemistry, 31, 1371 (1992)].

Substituted 1,2-diphenylcyclopentenes have been synthesized for use in studies of their rotational behavior, includes specifically, 1-(2,4-Dimethylphenyl)-2-phenylcyclopentene [D. Y. Curtin, et al., J. Org. Chem., 36, 565 (1971)]. 1,2-Di-(2'-methoxyphenyl)-$\Delta^1$-cyclopentene has been identified as an impurity in the synthesis of cannabinoids [O. P. Malik, et al., Ind. J. Chem., 14B, 975 (1976)].

1-(Substitutedphenyl)-2-phenylcyclopentenes have been synthesized to study their photochemical reactions into phenanthrene derivatives. Compounds with meta substituents, such as 1-(3-chlorophenyl)-2-phenylcyclopentene, are described in Somers, et al., J. Photochem. Photobiol., 48A, 353 (1989). Para substituents, including specifically 1-(4-fluorophenyl)-2-phenylcyclopentene, are described in Laarhoven, Pure & Appl. Chem., 56, 1225 (1984).

DESCRIPTION OF THE INVENTION

A class of cyclopentene compounds useful in treating inflammation-related disorders is defined by Formula I:

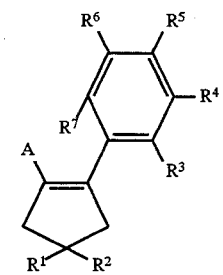

wherein A is selected from

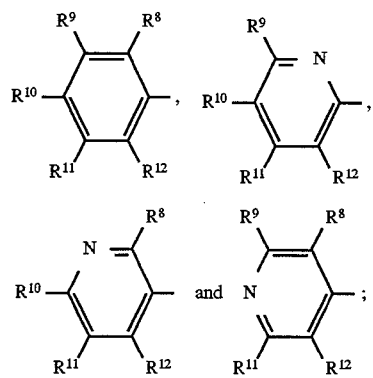

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl; provided that when A is

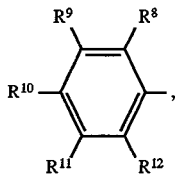

$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.

The phrase "further provided", as used in the above description, is intended to mean that the denoted proviso is not to be considered conjunctive with the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects.

The present invention preferably includes compounds which selectively inhibit cyclooxygenase II over cyclooxygenase I and do not significantly inhibit one or more other arachidonic pathway steps, such as thromboxane $B_2$ ($TXB_2$) production.

Preferably, the compounds have a cyclooxygenase II $IC_{50}$ of less than about 0.1 μM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 0.5 μM, and more preferably of greater than 5 μM. Such preferred selectivity may indicate an ability to reduce the incidence of common NSAID-induced side effects.

A preferred class of compounds consists of those compounds of Formula I wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl.

A class of compounds of particular interest consists of those compounds of Formula I wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, trifluoromethylsulfonyl and sulfamyl.

Within Formula I there is a subclass of compounds of high interest represented by Formula II:

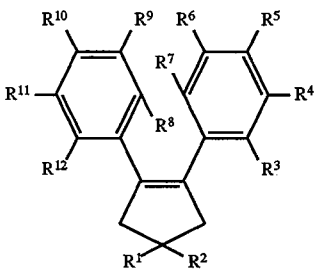

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl;

provided that $R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy;

or a pharmaceutically suitable salt thereof.

A preferred class of compounds consists of those compounds of Formula II wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl.

A class of compounds of particular interest consists of those compounds of Formula II wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, trifluoromethylsulfonyl and sulfamyl.

A more preferred class of compounds consists of those compounds of Formula II wherein $R^5$ is selected from methylsulfonyl, ethylsulfonyl, trifluoromethylsulfonyl and sulfamyl.

A family of specific compounds of particular interest within Formula II consists of compounds and pharmaceutically-acceptable salts thereof as follows:

1-[2-(3,4-dimethylphenyl)cyclopenten-1-yl]-4-(methylsulfonyl)benzene;
1-[2-(3-fluoro-4-methylphenyl)cyclopenten-1-yl]-4-(methylsulfonyl)benzene;
1-[2-(3-chloro-4-methylphenyl)cyclopenten-1-yl]-4-(methylsulfonyl)benzene;
1-[2-(3-trifluoromethyl-4-methylphenyl)cyclopenten-1-yl]-4-(methylsulfonyl)benzene;
1-[2-(3-methoxy-4-methylphenyl)cyclopenten-1-yl]-4-(methylsulfonyl)benzene;
1-[2-(3,4-difluorophenyl)cyclopenten-1-yl]-4-(methylsulfonyl)benzene;
1-[2-(3-methyl-4-fluorophenyl)cyclopenten-1-yl]-4-(methylsulfonyl)benzene;
1-[2-(3-chloro-4-fluorophenyl)cyclopenten-1-yl]-4-(methylsulfonyl)benzene;
1-[2-(3-trifluoromethyl-4-fluorophenyl)cyclopenten-1-yl]-4-(methylsulfonyl)benzene;
1-[2-(3-methoxy-4-fluorophenyl)cyclopenten-1-yl]-4-(methylsulfonyl)benzene;
1-[2-(3,4-dichlorophenyl)cyclopenten-1-yl]-4-(methylsulfonyl)benzene;
1-[2-(3-methyl-4-chlorophenyl)cyclopenten-1-yl]-4-(methylsulfonyl)benzene;
1-[2-(3-fluoro-4-chlorophenyl)cyclopenten-1-yl]-4-(methylsulfonyl)benzene;
1-[2-(3-trifluoromethyl-4-chlorophenyl)cyclopenten-1-yl]-4-(methylsulfonyl)benzene;
1-[2-(3-methoxy-4-chlorophenyl)cyclopenten-1-yl]-4-(methylsulfonyl)benzene;
1-[2-(3,4-methoxyphenyl)cyclopenten-1-yl]-4-(methylsulfonyl)benzene;
1-[2-(3-methyl-4-methoxyphenyl)cyclopenten-1-yl]-4-(methylsulfonyl)benzene;
1-[2-(3-fluoro-4-methoxyphenyl)cyclopenten-1-yl]-4-(methylsulfonyl)benzene;
1-[2-(3-trifluoromethyl-4-methoxyphenyl)cyclopenten-1-yl]-4-(methylsulfonyl)benzene;
1-[2-(3-chloro-4-methoxyphenyl)cyclopenten-1-yl]-4-(methylsulfonyl)benzene;
1-[2-[3,4-di(trifluoromethyl)phenyl]cyclopenten-1-yl]-4-(methylsulfonyl)benzene;
1-[2-(3-methyl-4-trifluoromethylphenyl)cyclopenten-1-yl]-4-(methylsulfonyl)benzene;
1-[2-(3-fluoro-4-trifluoromethylphenyl)cyclopenten-1-yl]-4-(methylsulfonyl)benzene;
1-[2-(3-methoxy-4-trifluoromethylphenyl)cyclopenten-1-yl]-4-(methylsulfonyl)benzene;
1-[2-(3-chloro-4-trifluoromethylphenyl)cyclopenten-1-yl]-4-(methylsulfonyl)benzene;
1-[2-(3-difluoromethyl-4-methylphenyl)cyclopenten-1-yl]-4-(methylsulfonyl)benzene;
1-[2-(3-difluoromethyl-4-fluorophenyl)cyclopenten-1-yl]-4-(methylsulfonyl)benzene;
1-[2-(3-difluoromethyl-4-chlorophenyl)cyclopenten-1-yl]-4-(methylsulfonyl)benzene;
1-[2-(3-difluoromethyl-4-methoxyphenyl)cyclopenten-1-yl]-4-(methylsulfonyl)benzene;
1-[2-[3,4-di(difluoromethyl)phenyl]cyclopenten-1-yl]-4-(methylsulfonyl)benzene;
1-[2-(3-methyl-4-difluoromethylphenyl)cyclopenten-1-yl]-4-(methylsulfonyl)benzene;
1-[2-(3-fluoro-4-difluoromethylphenyl)cyclopenten-1-yl]-4-(methylsulfonyl)benzene;
1-[2-(3-methoxy-4-difluoromethylphenyl)cyclopenten-1-yl]-4-(methylsulfonyl)benzene;
1-[2-(3-chloro-4-difluoromethylphenyl)cyclopenten-1-yl]-4-(methylsulfonyl)benzene;
1-[2-(2,3-difluorophenyl)cyclopenten-1-yl]-4-(methylsulfonyl)benzene;
4-[2-(2,3-difluorophenyl)cyclopenten-1-yl]-benzenesulfonamide;
4-[2-(3,4-dimethylphenyl)cyclopenten-1-yl]benzenesulfonamide;
4-[2-(3-fluoro-4-methylphenyl)cyclopenten-1-yl]benzenesulfonamide;
4-[2-(3-chloro-4-methylphenyl)cyclopenten-1-yl]benzenesulfonamide;
4-[2-(3-trifluoromethyl-4-methylphenyl)cyclopenten-1-yl]benzenesulfonamide;
4-[2-(3-methoxy-4-methylphenyl)cyclopenten-1-yl]benzenesulfonamide;
4-[2-(3,4-difluorophenyl)cyclopenten-1-yl]benzenesulfonamide;
4-[2-(3-methyl-4-fluorophenyl)cyclopenten-1-yl]benzenesulfonamide;
4-[2-(3-chloro-4-fluorophenyl)cyclopenten-1-yl]benzenesulfonamide;
4-[2-(3-trifluoromethyl-4-fluorophenyl)cyclopenten-1-yl]benzenesulfonamide;
4-[2-(3-methoxy-4-fluorophenyl)cyclopenten-1-yl]benzenesulfonamide;
4-[2-(3,4-dichlorophenyl)cyclopenten-1-yl]benzenesulfonamide;
4-[2-(3-methyl-4-chlorophenyl)cyclopenten-1-yl]benzenesulfonamide;
4-[2-(3-fluoro-4-chlorophenyl)cyclopenten-1-yl]benzenesulfonamide;
4-[2-(3-trifluoromethyl-4-chlorophenyl)cyclopenten-1-yl]benzenesulfonamide;
4-[2-(3-methoxy-4-chlorophenyl)cyclopenten-1-yl]benzenesulfonamide;

4-[2-(3,4-methoxyphenyl)cyclopenten-1-yl]
benzenesulfonamide;
4-[2-(3-methyl-4-methoxyphenyl)cyclopenten-1-yl]
benzenesulfonamide;
4-[2-(3-fluoro-4-methoxyphenyl)cyclopenten-1-yl]
benzenesulfonamide;
4-[2-(3-trifluoromethyl-4-methoxyphenyl)cyclopenten-1-yl]benzenesulfonamide;
4-[2-(3-chloro-4-methoxyphenyl)cyclopenten-1-yl]
benzenesulfonamide;
4-[2-[3,4-di(trifluoromethyl)phenyl]cyclopenten-1-yl]
benzenesulfonamide;
4-[2-(3-methyl-4-trifluoromethylphenyl)cyclopenten-1-yl]
benzenesulfonamide;
4-[2-(3-fluoro-4-trifluoromethylphenyl)cyclopenten-1-yl]
benzenesulfonamide;
4-[2-(3-methoxy-4-trifluoromethylphenyl)cyclopenten-1-yl]benzenesulfonamide;
4-[2-(3-chloro-4-trifluoromethylphenyl)cyclopenten-1-yl]
benzenesulfonamide;
4-[2-(3-difluoromethyl-4-methylphenyl)cyclopenten-1-yl]
benzenesulfonamide;
4-[2-(3-difluoromethyl-4-fluorophenyl)cyclopenten-1-yl]
benzenesulfonamide;
4-[2-(3-difluoromethyl-4-chlorophenyl)cyclopenten-1-yl]
benzenesulfonamide;
4-[2-(3-difluoromethyl-4-methoxyphenyl)cyclopenten-1-yl]
benzenesulfonamide;
4-[2-[3,4-di(difluoromethyl)phenyl]cyclopenten-1-yl]
benzenesulfonamide;
4-[2-(3-methyl-4-difluoromethylphenyl)cyclopenten-1-yl]
benzenesulfonamide;
4-[2-(3-fluoro-4-difluoromethylphenyl)cyclopenten-1-yl]
benzenesulfonamide;
4-[2-(3-methoxy-4-difluoromethylphenyl)cyclopenten-1-yl]
benzenesulfonamide;
4-[2-(3-chloro-4-difluoromethylphenyl)cyclopenten-1-yl]
benzenesulfonamide;
1-(2-phenylcyclopenten-1-yl)-4-(methylsulfonyl)benzene;
1-[2-(4-fluorophenyl)cyclopenten-1-yl]-4-(methylsulfonyl)
benzene;
1-[2-(4-chlorophenyl)cyclopenten-1-yl]-4-(methylsulfonyl)
benzene;
1-[2-(4-bromophenyl)cyclopenten-1-yl]-4-(methylsulfonyl)
benzene;
1-[2-(4-iodophenyl)cyclopenten-1-yl]-4-(methylsulfonyl)
benzene;
1-[2-(4-methylphenyl)cyclopenten-1-yl]-4-(methylsulfonyl)
benzene;
1-[2-(4-ethylphenyl)cyclopenten-1-yl]-4-(methylsulfonyl)
benzene;
1-[2-(4-cyanophenyl)cyclopenten-1-yl]-4-(methylsulfonyl)
benzene;
1-[2-(4-trifluoromethylphenyl)cyclopenten-1-yl]-4-
(methylsulfonyl)benzene;
1-[2-(4-methoxyphenyl)cyclopenten-1-yl]-4-
(methylsulfonyl)benzene;
1-[2-(4-methylthiophenyl)cyclopenten-1-yl]-4-
(methylsulfonyl)benzene;
1-[2-(4-hydroxymethylphenyl)cyclopenten-1-yl]-4-
(methylsulfonyl)benzene;
1-[2-(4-methoxymethylphenyl)cyclopenten-1-yl]-4-
(methylsulfonyl)benzene;
1-[2-(2,4-dimethylphenyl)cyclopenten-1-yl]-4-
(methylsulfonyl)benzene;
1-[2-(2-methyl-4-fluorophenyl)cyclopenten-1-yl]-4-
(methylsulfonyl)benzene;
1-[2-(2-methyl-4-chlorophenyl)cyclopenten-1-yl]-4-
(methylsulfonyl)benzene;
1-[2-(2-fluoro-4-methylphenyl)cyclopenten-1-yl]-4-
(methylsulfonyl)benzene;
1-[2-(2,4-difluorophenyl)cyclopenten-1-yl]-4-
(methylsulfonyl)benzene;
1-[2-(2-fluoro-4-chlorophenyl)cyclopenten-1-yl]-4-
(methylsulfonyl)benzene;
1-[2-chloro-4-methylphenyl)cyclopenten-1-yl]-4-
(methylsulfonyl)benzene;
1-[2-(2-chloro-4-fluorophenyl)cyclopenten-1-yl]-4-
(methylsulfonyl)benzene;
1-[2-(2,4-dichlorophenyl)cyclopenten-1-yl]-4-
(methylsulfonyl)benzene;
4-(2-phenylcyclopenten-1-yl)benzenesulfonamide;
4-[2-(4-fluorophenyl)cyclopenten-1-yl]
benzenesulfonamide;
4-[2-(4-chlorophenyl)cyclopenten-1-yl]
benzenesulfonamide;
4-[2-(4-methylphenyl)cyclopenten-1-yl]
benzenesulfonamide;
4-[2-(4-cyanophenyl)cyclopenten-1-yl]
benzenesulfonamide;
4-[2-(4-methoxyphenyl)cyclopenten-1-yl]
benzenesulfonamide;
4-[2-(4-methylthiophenyl)cyclopenten-1-yl]
benzenesulfonamide;
4-[2-(4-hydroxymethylphenyl)cyclopenten-1-yl]
benzenesulfonamide;
4-[2-(4-methoxymethylphenyl)cyclopenten-1-yl]
benzenesulfonamide;
4-[2-(4-trifluoromethylphenyl)cyclopenten-1-yl]
benzenesulfonamide;
4-[2-(2,4-dimethylphenyl)cyclopenten-1-yl]
benzenesulfonamide;
4-[2-(2-methyl-4-fluorophenyl)cyclopenten-1-yl]
benzenesulfonamide;
4-[2-(2-methyl-4-chlorophenyl)cyclopenten-1-yl]
benzenesulfonamide;
4-[2-(2-fluoro-4-methylphenyl)cyclopenten-1-yl]
benzenesulfonamide;
4-[2-(2,4-difluorophenyl)cyclopenten-1-yl]
benzenesulfonamide;
4-[2-(2-fluoro-4-chlorophenyl)cyclopenten-1-yl]
benzenesulfonamide;
4-[2-(2-chloro-4-methylphenyl)cyclopenten-1-yl]
benzenesulfonamide;
4-[2-(2-chloro-4-fluorophenyl)cyclopenten-1-yl]
benzenesulfonamide;
4-[2-(2,4-dichlorophenyl)cyclopenten-1-yl]
benzenesulfonamide;
4-[2-(4-chlorophenyl)-4,4-dimethylcyclopenten-1-yl]
benzenesulfonamide;
1-[2-(4-fluorophenyl)cyclopenten-1-yl]-4-
(fluoromethylsulfonyl)benzene;
1-[2-(4-chlorophenyl)-4,4-dimethylcyclopenten-1-yl]-4-
(methylsulfonyl)benzene;
5-[2-(4-(methylsulfonyl)phenyl]cyclopenten-1-yl]-1,3-
benzodioxole;
5-[2-(4-(aminosulfonyl)phenyl]cyclopenten-1-yl]-1,3-
benzodioxole;
1-[2-(4-fluorophenyl)-4,4-dimethylcyclopenten-1-yl]-4-
(methylsulfonyl)benzene;
1-[2-(4-fluorophenyl)-4,4-diethylcyclopenten-1-yl]-4-
(methylsulfonyl)benzene;
1-[2-(4-fluorophenyl)-4,4-di(hydroxymethyl)cyclopenten-
1-yl]-4-(methylsulfonyl)benzene;

1-[2-(4-fluorophenyl)-4,4-dicarbomethoxycyclopenten-1-yl]-4-(methylsulfonyl)benzene;
1-[2-(4-fluorophenyl)-4,4-difluorocyclopenten-1-yl]-4-(methylsulfonyl)benzene;
1-[2-(4-fluorophenyl)-4,4-di(trifluoromethyl)cyclopenten-1-yl]-4-(methylsulfonyl)benzene;
1-[2-(4-fluorophenyl)-4,4-di(fluoromethyl)cyclopenten-1-yl]-4-(methylsulfonyl)benzene;
1-[2-(4-trifluoromethylphenyl)-4,4-dimethylcyclopenten-1-yl]-4-(methylsulfonyl)benzene;
1-[2-(4-trifluoromethylphenyl)-4,4-diethylcyclopenten-1-yl]-4-(methylsulfonyl)benzene;
1-[2-(4-trifluoromethylphenyl)-4,4-di(hydroxymethyl)cyclopenten-1-yl]-4-(methylsulfonyl)benzene;
1-[2-(4-trifluoromethylphenyl)-4,4-dicarbomethoxycyclopenten-1-yl]-4-(methylsulfonyl)benzene;
1-[2-(4-trifluoromethylphenyl)-4,4-difluorocyclopenten-1-yl]-4-(methylsulfonyl)benzene;
1-[2-(4-trifluoromethylphenyl)-4,4-di(trifluoromethyl)cyclopenten-1-yl]-4-(methylsulfonyl)benzene;
1-[2-(4-trifluoromethylphenyl)-4,4-di(fluoromethyl)cyclopenten-1-yl]-4-(methylsulfonyl)benzene;
4-[2-(4-fluorophenyl)-4,4-dimethylcyclopenten-1-yl]benzenesulfonamide;
4-[2-(4-fluorophenyl)-4,4-diethylcyclopenten-1-yl]benzenesulfonamide;
4-[2-(4-fluorophenyl)-4,4-di(hydroxymethyl)cyclopenten-1-yl]benzenesulfonamide;
4-[2-(4-fluorophenyl)-4,4-dicarbomethoxycyclopenten-1-yl]benzenesulfonamide;
4-[2-(4-fluorophenyl)-4,4-difluorocyclopenten-1-yl]benzenesulfonamide;
4-[2-(4-fluorophenyl)-4,4-di(trifluoromethyl)cyclopenten-1-yl]benzenesulfonamide;
4-[2-(4-fluorophenyl)-4,4-di(fluoromethyl)cyclopenten-1-yl]benzenesulfonamide;
4-[2-(4-trifluoromethylphenyl)-4,4-dimethylcyclopenten-1-yl]benzenesulfonamide;
4-[2-(4-trifluoromethylphenyl)-4,4-diethylcyclopenten-1-yl]benzenesulfonamide;
4-[2-(4-trifluoromethylphenyl)-4,4-di(hydroxymethyl)cyclopenten-1-yl]benzenesulfonamide;
4-[2-(4-trifluoromethylphenyl)-4,4-dicarbomethoxycyclopenten-1-yl]benzenesulfonamide;
4-[2-(4-trifluoromethylphenyl)-4,4-difluorocyclopenten-1-yl]benzenesulfonamide;
4-[2-(4-trifluoromethylphenyl)-4,4-di(trifluoromethyl)cyclopenten-1-yl]benzenesulfonamide;
4-[2-(4-trifluoromethylphenyl)-4,4-di(fluoromethyl)cyclopenten-1-yl]benzenesulfonamide;
1-[2-(4-fluorophenyl)-4-methylcyclopenten-1-yl]-4-(methylsulfonyl)benzene;
1-[2-(4-fluorophenyl)-4-ethylcyclopenten-1-yl]-4-(methylsulfonyl)benzene;
1-[2-(4-fluorophenyl)-4-(hydroxymethyl)cyclopenten-1-yl]-4-(methylsulfonyl)benzene;
1-[2-(4-fluorophenyl)-4-carbomethoxycyclopenten-1-yl]-4-(methylsulfonyl)benzene;
1-[2-(4-fluorophenyl)-4-fluorocyclopenten-1-yl]-4-(methylsulfonyl)benzene;
1-[2-(4-fluorophenyl)-4-(trifluoromethylcyclopenten-1-yl]-4-(methylsulfonyl)benzene;
1-[2-(4-fluorophenyl)-4-carboxycyclopenten-1-yl]-4-(methylsulfonyl)benzene;
1-[2-(4-fluorophenyl)-4-(fluoromethyl)cyclopenten-1-yl]-4-(methylsulfonyl)benzene;
1-[2-(4-trifluoromethylphenyl)-4-methylcyclopenten-1-yl]-4-(methylsulfonyl)benzene;
1-[2-(4-trifluoromethylphenyl)-4-ethylcyclopenten-1-yl]-4-(methylsulfonyl)benzene;
1-[2-(4-trifluoromethylphenyl)-4-(hydroxymethyl)cyclopenten-1-yl]-4-(methylsulfonyl)benzene;
1-[2-(4-trifluoromethylphenyl)-4-carbomethoxycyclopenten-1-yl]-4-(methylsulfonyl)benzene;
1-[2-(4-trifluoromethylphenyl)-4-fluorocyclopenten-1-yl]-4-(methylsulfonyl)benzene;
1-[2-(4-trifluoromethylphenyl)-4-(trifluoromethyl)cyclopenten-1-yl]-4-(methylsulfonyl)benzene;
1-[2-(4-trifluoromethylphenyl)-4-carboxycyclopenten-1-yl]-4-(methylsulfonyl)benzene;
1-[2-(4-trifluoromethylphenyl)-4-(fluoromethyl)cyclopenten-1-yl]-4-(methylsulfonyl)benzene;
1-[2-(2,4,6-trifluorophenyl)cyclopenten-1-yl]-4-(methylsulfonyl)benzene;
4-[2-(4-fluorophenyl)-4-methylcyclopenten-1-yl]benzenesulfonamide;
4-[2-(4-fluorophenyl)-4-ethylcyclopenten-1-yl]benzenesulfonamide;
4-[2-(4-fluorophenyl)-4-(hydroxymethyl)cyclopenten-1-yl]benzenesulfonamide;
4-[2-(4-fluorophenyl)-4-carbomethoxycyclopenten-1-yl]benzenesulfonamide;
4-[2-(4-fluorophenyl)-4-fluorocyclopenten-1-yl]benzenesulfonamide;
4-[2-(4-fluorophenyl)-4-(trifluoromethyl)cyclopenten-1-yl]benzenesulfonamide;
4-[2-(4-fluorophenyl)-4-carboxycyclopenten-1-yl]benzenesulfonamide;
4-[2-(4-fluorophenyl)-4-(fluoromethyl)cyclopenten-1-yl]benzenesulfonamide;
4-[2-(4-trifluoromethylphenyl)-4-methylcyclopenten-1-yl]benzenesulfonamide;
4-[2-(4-trifluoromethylphenyl)-4-ethylcyclopenten-1-yl]benzenesulfonamide;
4-[2-(4-trifluoromethylphenyl)-4-(hydroxymethyl)cyclopenten-1-yl]benzenesulfonamide;
4-[2-(4-trifluoromethylphenyl)-4-carbomethoxycyclopenten-1-yl]benzenesulfonamide;
4-[2-(4-trifluoromethylphenyl)-4-fluorocyclopenten-1-yl]benzenesulfonamide;
4-[2-(4-trifluoromethylphenyl)-4-trifluoromethylcyclopenten-1-yl]benzenesulfonamide;
4-[2-(2,4,6-trifluorophenyl)cyclopenten-1-yl]benzenesulfonamide;
4-[2-(4-trifluoromethylphenyl)-4-carboxycyclopenten-1-yl]benzenesulfonamide; and
4-[2-(4-trifluoromethylphenyl)-4-(fluoromethyl)cyclopenten-1-yl]benzenesulfonamide.

A family of compounds of more particular interest within Formula II consists of compounds and their pharmaceutically-acceptable salts as follows:

1-[2-(4-chlorophenyl)-4,4-dimethylcyclopenten-1-yl]-4-(methylsulfonyl)benzene;
1-[2-(4-fluorophenyl)-4,4-di(fluoromethyl)cyclopenten-1-yl]-4-(methylsulfonyl)benzene;
1-[2-(4-fluorophenyl)-4,4-di(trifluoromethyl)cyclopenten-1-yl]-4-(methylsulfonyl)benzene;
1-[2-(4-fluorophenyl)-4,4-diethylcyclopenten-1-yl]-4-(methylsulfonyl)benzene;
4-[2-(4-fluorophenyl)-4,4-diethylcyclopenten-1-yl]benzenesulfonamide;
1-[2-(4-methoxyphenyl)cyclopenten-1-yl]-4-(methylsulfonyl)benzene;

4-[2-(4-methoxyphenyl)cyclopenten-1-yl]
benzenesulfonamide;

4-[2-(4-chlorophenyl)-4,4-dimethylcyclopenten-1-yl]
benzenesulfonamide;

1-[2-(4-fluorophenyl)cyclopenten-1-yl]-4-
(fluoromethylsulfonyl)benzene;

5-[2-(4-(methylsulfonyl)phenyl]cyclopenten-1-yl]-1,3-
benzodioxole;

4-[2-(4-fluorophenyl)-4,4-dimethylcyclopenten-1-yl]
benzenesulfonamide;

4-[2-(4-fluorophenyl)cyclopenten-1-yl]
benzenesulfonamide;

4-[2-(4-chlorophenyl)cyclopenten-1-yl]
benzenesulfonamide;

4-[2-(4-(trifluoromethyl)phenyl)cyclopenten-1-yl]
benzenesulfonamide;

1-[2-(2,3-difluorophenyl)cyclopenten-1-yl]-4-
(methylsulfonyl)benzene;

4-[2-(2,3-difluorophenyl)cyclopenten-1-yl]
benzenesulfonamide;

1-[2-(3,4-dichlorophenyl)cyclopenten-1-yl]-4-
(methylsulfonyl)benzene;

4-[2-(3,4-dichlorophenyl)cyclopenten-1-yl]
benzenesulfonamide;

1-[2-(3-fluoro-4-methoxyphenyl)cyclopenten-1-yl]-4-
(methylsulfonyl)benzene;

4-[2-(3-fluoro-4-methoxyphenyl)cyclopenten-1-yl]
benzenesulfonamide;

1-[2-(3-chloro-4-methoxyphenyl)cyclopenten-1-yl]-4-
(methylsulfonyl)benzene;

4-[2-(3-chloro-4-methoxyphenyl)cyclopenten-1-yl]
benzenesulfonamide;

1-[2-(3-chloro-4-fluorophenyl)cyclopenten-1-yl]-4-
(methylsulfonyl)benzene;

4-[2-(3-chloro-4-fluorophenyl)cyclopenten-1-yl]
benzenesulfonamide;

1-[2-(3,4-difluorophenyl)cyclopenten-1-yl]-4-
(methylsulfonyl)benzene;

4-[2-(3,4-difluorophenyl)cyclopenten-1-yl]
benzenesulfonamide;

1-[2-(4-fluorophenyl)cyclopenten-1-yl]-4-(methylsulfonyl)
benzene;

1-[2-(4-fluoro-2-methylphenyl)cyclopenten-1-yl]-4-
(methylsulfonyl)benzene;

1-[2-(2,4-dichlorophenyl)cyclopenten-1-yl]-4-
(methylsulfonyl)benzene;

1-[2-(4-chlorophenyl)cyclopenten-1-yl]-4-(methylsulfonyl)
benzene;

1-[2-(4-trifluoromethylphenyl)cyclopenten-1-yl]-4-
(methylsulfonyl)benzene;

1-[2-(4-methylphenyl)cyclopenten-1-yl]-4-(methylsulfonyl)
benzene;

1-(2-phenylcyclopenten-1-yl)-4-(methylsulfonyl)benzene;

1-[2-(4-cyanophenyl)cyclopenten-1-yl]-4-(methylsulfonyl)
benzene;

1-[2-(4-hydroxymethylphenyl)cyclopenten-1-yl]-4-
(methylsulfonyl)benzene;

1-[2-(4-methoxymethylphenyl)cyclopenten-1-yl]-4-
(methylsulfonyl)benzene;

1-[2-(4-methylthiophenyl)cyclopenten-1-yl]-4-
(methylsulfonyl)benzene; and

1-[2-(4-fluorophenyl)-4,4-dimethylcyclopenten-1-yl]-4-
(methylsulfonyl)benzene.

Within Formula I there is a second subclass of compounds of high interest represented by Formula III:

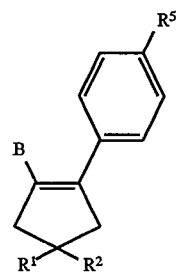

wherein each of $R^1$ and $R^2$ is independently selected from alkyl, hydrido, hydroxyalkyl, halo, haloalkyl, alkoxycarbonyl and carboxyl;

wherein $R^5$ is selected from alkylsulfonyl, haloalkylsulfonyl and sulfamyl; and wherein B is phenyl or pyridinyl, wherein B is optionally substituted at a substitutable position with alkyl, halo, alkylthio, cyano, haloalkyl, alkoxy, hydroxyalkyl and alkoxyalkyl; or a pharmaceutically-acceptable salt thereof.

A preferred class of compounds consists of those compounds of Formula III wherein each of $R^1$ and $R^2$ is independently selected from lower alkyl, hydrido, lower hydroxyalkyl, halo, lower haloalkyl, lower alkoxycarbonyl and carboxyl; wherein $R^5$ is selected from lower alkylsulfonyl, lower haloalkylsulfonyl and sulfamyl; and wherein B is phenyl or pyridinyl, wherein B is optionally substituted at a substitutable position with lower alkyl, halo, lower alkylthio, cyano, lower haloalkyl, lower alkoxy, lower hydroxyalkyl and lower alkoxyalkyl.

A class of compounds of particular interest consists of those compounds of Formula III wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; wherein $R^5$ is selected from methylsulfonyl, trifluoromethylsulfonyl and sulfamyl; and wherein B is optionally substituted with a radical selected from fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tertbutoxymethyl, propoxyethyl, butoxymethyl, isobutoxymethyl and pentoxymethyl.

Within Formula I there is a third subclass of compounds of high interest represented by Formula IV:

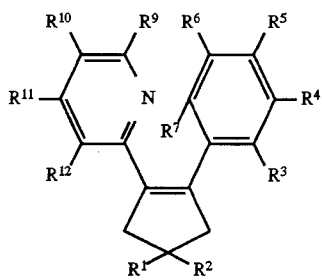

wherein each of $R^1$ and $R^2$ is independently selected from alkyl, hydrido, hydroxyalkyl, halo, haloalkyl, alkoxycarbonyl and carboxyl; and wherein each of $R^3$ through $R^7$ and $R^9$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl; or a pharmaceutically-acceptable salt thereof.

A preferred class of compounds consists of those compounds of Formula IV wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^7$ and $R^9$ through $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl.

A class of compounds of particular interest consists of those compounds of Formula IV wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^7$ and $R^9$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, trifluoromethylsulfonyl and sulfamyl.

A family of specific compounds of particular interest within Formula IV consists of compounds and pharmaceutically-acceptable salts thereof as follows:
2-[2-(4-(methylsulfonyl)phenyl]cyclopenten-1-yl]pyridine;
5-fluoro-2-[2-(4-(methylsulfonyl)phenyl]cyclopenten-1-yl]pyridine;
5-chloro-2-[2-(4-(methylsulfonyl)phenyl]cyclopenten-1-yl]pyridine;
5-methyl-2-[2-(4-(methylsulfonyl)phenyl]cyclopenten-1-yl]pyridine;
5-cyano-2-[2-(4-(methylsulfonyl)phenyl]cyclopenten-1-yl]pyridine;
5-trifluoromethyl-2-[2-(4-(methylsulfonyl)phenyl]cyclopenten-1-yl]pyridine;
4-[2-(pyridin-2-yl)cyclopenten-1-yl]benzenesulfonamide;
4-[2-(5-fluoropyridin-2-yl)cyclopenten-1-yl]benzenesulfonamide;
4-[2-(5-chloropyridin-2-yl)cyclopenten-1-yl]benzenesulfonamide;
4-[2-(5-methylpyridin-2-yl)cyclopenten-1-yl]benzenesulfonamide;
4-[2-(5-cyanopyridin-2-yl)cyclopenten-1-yl]benzenesulfonamide;
4-[2-(5-trifluoromethylpyridin-2-yl)cyclopenten-1-yl]benzenesulfonamide;
5-fluoro-2-[2-[4-(methylsulfonyl)phenyl]-4-methylcyclopenten-1-yl]pyridine;
5-fluoro-2-[2-[4-(methylsulfonyl)phenyl]-4-ethylcyclopenten-1yl]pyridine;
5-fluoro-2-[2-[4-(methylsulfonyl)phenyl]-4-(hydroxymethyl)cyclopenten-1-yl]pyridine;
5-fluoro-2-[2-[4-(methylsulfonyl)phenyl]-4-carbomethoxycyclopenten-1-yl]pyridine;
5-fluoro-2-[2-[4-(methylsulfonyl)phenyl]-4-fluorocyclopenten-1-yl]pyridine;
5-fluoro-2-[2-[4-(methylsulfonyl)phenyl]-4-(trifluoromethyl)cyclopenten-1-yl]pyridine;
5-fluoro-2-[2-[4-(methylsulfonyl)phenyl]-4-carboxycyclopenten-1-yl]pyridine;
5-fluoro-2-[2-[4-(methylsulfonyl)phenyl]-4-(fluoromethyl)cyclopenten-1-yl]pyridine;
5-trifluoromethyl-2-[2-[4-(methylsulfonyl)phenyl]-4-methylcyclopenten-1-yl]pyridine;
5-trifluoromethyl-2-[2-[4-(methylsulfonyl)phenyl]-4-ethylcyclopenten-1 yl]pyridine;
5-trifluoromethyl-2-[2-[4-(methylsulfonyl)phenyl]-4-(hydroxymethyl)cyclopenten-1-yl]pyridine;
5-trifluoromethyl-2-[2-[4-(methylsulfonyl)phenyl]-4-carbomethoxycyclopenten-1-yl]pyridine;
5-trifluoromethyl-2-[2-[4-(methylsulfonyl)phenyl]-4-fluorocyclopenten-1-yl]pyridine
5-trifluoromethyl-2-[2-[4-(methylsulfonyl)phenyl]-4-(trifluoromethyl)cyclopenten-1-yl]pyridine
5-trifluoromethyl-2-[2-[4-(methylsulfonyl)phenyl]-4-carboxycyclopenten-1-yl]pyridine;
5-trifluoromethyl-2-[2-[4-(methylsulfonyl)phenyl]-4-(fluoromethyl)cyclopenten-1-yl]pyridine;
4-[2-(5-fluoropyridin-2-yl)-4-methylcyclopenten-1-yl]benzenesulfonamide;
4-[2-(5-fluoropyridin-2-yl)-4-ethylcyclopenten-1-yl]benzenesulfonamide;
4-[2-(5-fluoropyridin-2-yl)-4-(hydroxymethyl)cyclopenten-1-yl]benzenesulfonamide;
4-[2-(5-fluoropyridin-2-yl)-4-carbomethoxycyclopenten-1-yl]benzenesulfonamide;
4-[2-(5-fluoropyridin-2-yl)-4-fluorocyclopenten-1-yl]benzenesulfonamide;
4-[2-(5-fluoropyridin-2-yl)-4-(trifluoromethyl)cyclopenten-1 -yl]benzenesulfonamide;
4-[2-(5-fluoropyridin-2-yl)-4-carboxycyclopenten-1-yl]benzenesulfonamide
4-[2-(5-fluoropyridin-2-yl)-4-(fluoromethyl)cyclopenten-1-yl]benzenesulfonamide;
4-[2-(5-trifluoromethylpyridin-2-yl)-4-methylcyclopenten-1-yl]benzenesulfonamide;
4-[2-(5-trifluoromethylpyridin-2-yl)-4-ethylcyclopenten-1-yl]benzenesulfonamide;
4-[2-(5-trifluoromethylpyridin-2-yl)-4-(hydroxymethyl)cyclopenten-1-yl]benzenesulfonamide;

4-[2-(5-trifluoromethylpyridin-2-yl)-4-carbomethoxycyclopenten-1-yl]benzenesulfonamide;

4-[2-(5-trifluoromethylpyridin-2-yl)-4-fluorocyclopenten-1-yl]benzenesulfonamide;

4-[2-(5-trifluoromethylpyridin-2-yl)-4-(trifluoromethyl)cyclopenten-1-yl]benzenesulfonamide;

4-[2-(5-trifluoromethylpyridin-2-yl)-4-carboxycyclopenten-1-yl]benzenesulfonamide;

4-[2-(5-trifluoromethylpyridin-2-yl)-4-fluoromethylcyclopenten-1-yl]benzenesulfonamide;

5-fluoro-2-[2-[4-(methylsulfonyl)phenyl]-4,4-dimethylcyclopenten-1-yl]pyridine;

5-fluoro-2-[2-[4-(methylsulfonyl)phenyl]-4,4-diethylcyclopenten-1-yl]pyridine;

5-fluoro-2-[2-[4-(methylsulfonyl)phenyl]-4-di(hydroxymethyl)cyclopenten-1-yl]pyridine;

5-fluoro-2-[2-[4-(methylsulfonyl)phenyl]-4,4-dicarbomethoxycyclopenten-1-yl]pyridine;

5-fluoro-2-[2-[4-(methylsulfonyl)phenyl]-4,4-difluorocyclopenten-1-yl]pyridine;

5-fluoro-2-[2-[4-(methylsulfonyl)phenyl]-4,4-di(trifluoromethyl)cyclopenten-1-yl]pyridine;

5-fluoro-2-[2-[4-(methylsulfonyl)phenyl]-4,4-di(fluoromethyl)cyclopenten-1-yl]pyridine;

5-trifluoromethyl-2-[2-[4-(methylsulfonyl)phenyl]-4,4-dimethylcyclopenten-1-yl]pyridine;

5-trifluoromethyl-2-[2-[4-(methylsulfonyl)phenyl]-4,4-diethylcyclopenten-1-yl]pyridine;

5-trifluoromethyl-2-[2-[4-(methylsulfonyl)phenyl]-4,4-di(hydroxymethyl)cyclopenten-1-yl]pyridine;

5-trifluoromethyl-2-[2-[4-(methylsulfonyl)phenyl]-4,4-dicarbomethoxycyclopenten-1-yl]pyridine;

5-trifluoromethyl-2-[2-[4-(methylsulfonyl)phenyl]-4,4-difluorocyclopenten-1-yl]pyridine;

5-trifluoromethyl-2-[2-[4-(methylsulfonyl)phenyl]-4,4-di(trifluoromethyl)cyclopenten-1-yl]pyridine;

5-trifluoromethyl-2-[2-[4-(methylsulfonyl)phenyl]-4,4-di(fluoromethyl)cyclopenten-1-yl]pyridine;

4-[2-(5-fluoropyridin-2-yl)-4,4-dimethylcyclopenten-1-yl]benzenesulfonamide;

4-[2-(5-fluoropyridin-2-yl)-4,4-diethylcyclopenten-1-yl]benzenesulfonamide;

4-[2-(5-fluoropyridin-2-yl)-4,4-di(hydroxymethyl)cyclopenten-1-yl]benzenesulfonamide;

4-[2-(5-fluoropyridin-2-yl)-4,4-dicarbomethoxycyclopenten-1-yl]benzenesulfonamide;

4-[2-(5-fluoropyridin-2-yl)-4,4-difluorocyclopenten-1-yl]benzenesulfonamide;

4-[2-(5-fluoropyridin-2-yl)-4,4-di(trifluoromethyl)cyclopenten-1-yl]benzenesulfonamide;

4-[2-(5-fluoropyridin-2-yl)-4,4-di(fluoromethyl)cyclopenten-1-yl]benzenesulfonamide;

4-[2-(5-trifluoromethylpyridin-2-yl)-4,4-dimethylcyclopenten-1-yl]benzenesulfonamide;

4-[2-(5-trifluoromethylpyridin-2-yl)-4,4-diethylcyclopenten-1-yl]benzenesulfonamide;

4-[2-(5-trifluoromethylpyridin-2-yl)-4,4-di(hydroxymethyl)cyclopenten-1-yl]benzenesulfonamide;

4-[2-(5-trifluoromethylpyridin-2-yl)-4,4-dicarbomethoxycyclopenten-1-yl]benzenesulfonamide;

4-[2-(5-trifluoromethylpyridin-2-yl)-4,4-difluorocyclopenten-1-yl]benzenesulfonamide;

4-[2-(5-trifluoromethylpyridin-2-yl)-4,4-di(trifluoromethyl)cyclopenten-1-1]benzenesulfonamide;

4-[2-(5-trifluoromethylpyridin-2-yl)-4,4-di(fluoromethyl)cyclopenten-1-yl]benzenesulfonamide;

2-[2-phenylcyclopenten-1-yl]-5(methylsulfonyl)pyridine;

2-[2-(4-fluorophenyl)cyclopenten-1-yl]5(methylsulfonyl)pyridine;

2-[2-(4-chlorophenyl)cyclopenten-1-yl]-5-(methylsulfonyl)pyridine;

2-[2-(4-methylphenyl)cyclopenten-1-yl]-5-(methylsulfonyl)pyridine;

2-[2-(4-cyanophenyl)cyclopenten-1-yl]-5(methylsulfonyl)pyridine;

2-[2-(4-trifluoromethylphenyl)cyclopenten-1-yl]-5(methylsulfonyl)pyridine;

2-[2-phenylcyclopenten-1-yl]pyridine-5-sulfonamide;

2-[2-(4-fluorophenyl)cyclopenten-1-yl]pyridine-5-sulfonamide;

2-[2-(4-chlorophenyl)cyclopenten-1-yl]pyridine-5-sulfonamide;

2-[2-(4-methylphenyl)cyclopenten-1-yl]pyridine-5-sulfonamide;

2-[2-(4-cyanophenyl)cyclopenten-1-yl]pyridine-5-sulfonamide;

2-[2-(4-trifluoromethylphenyl)cyclopenten-1-yl]pyridine-5-sulfonamide;

2-[2-(4-fluorophenyl)-4-methylcyclopenten-1-yl]-5-(methylsulfonyl)pyridine;

2-[2-(4-fluorophenyl)-4-ethylcyclopenten-1-yl]-5-(methylsulfonyl)pyridine;

2-[2-(4-fluorophenyl)-4-(hydroxymethyl)cyclopenten-1-yl]-5-(methylsulfonyl)pyridine;

2-[2-(4-fluorophenyl)-4-fluorocyclopenten-1-yl]-5-(methylsulfonyl)pyridine;

2-[2-(4-fluorophenyl)-4-(trifluoromethyl)cyclopenten-1-yl]-5-(methylsulfonyl)pyridine;

2-[2-(4-fluorophenyl)-4-carboxycyclopenten-1-yl]-5-(methylsulfonyl)pyridine;

2-[2-(4-fluorophenyl)-4-(fluoromethyl)cyclopenten-1-yl]-5-(methylsulfonyl)pyridine;

2-[2-(4-trifluoromethylphenyl)-4-methylcyclopenten-1-yl]-5-(methylsulfonyl)pyridine;

2-[2-(4-trifluoromethylphenyl)-4-ethylcyclopenten-1-yl]-5-(methylsulfonyl)pyridine;

2-[2-(4-trifluoromethylphenyl)-4-(hydroxymethyl)cyclopenten-1-yl]-5-(methylsulfonyl)pyridine;

2-[2-(4-trifluoromethylphenyl)-4-carbomethoxycyclopenten-1-yl]-5-(methylsulfonyl)pyridine;

2-[2-(4-trifluoromethylphenyl)-4-fluorocyclopenten-1-yl]-5-(methylsulfonyl)pyridine;

2-[2-(4-trifluoromethylphenyl)-4-carboxycyclopenten-1-yl]-5-(methylsulfonyl)pyridine;

2-[2-(4-trifluoromethylphenyl)-4-(trifluoromethyl)cyclopenten-1-yl]-5-(methylsulfonyl)pyridine;

2-[2-(4-fluorophenyl)-4-methylcyclopenten-1-yl]pyridine-5-sulfonamide;

2-[2-(4-fluorophenyl)-4-ethylcyclopenten-1-yl]pyridine-5-sulfonamide;

2-[2-(4-fluorophenyl)-4-(hydroxymethyl)cyclopenten-1-yl]pyridine-5-sulfonamide;

2-[2-(4-fluorophenyl)-4-carbomethoxycyclopenten-1-yl]pyridine-5-sulfonamide;

2-[2-(4-fluorophenyl)-4-fluorocyclopenten-1-yl]pyridine-5-sulfonamide;

2-[2-(4-fluorophenyl)-4-(trifluoromethyl)cyclopenten-1-yl]pyridine-5-sulfonamide;

2-[2-(4-fluorophenyl)-4-carboxycyclopenten-1-yl]pyridine-5-sulfonamide;

2-[2-(4-fluorophenyl)-4-(fluoromethyl)cyclopenten-1-yl]pyridine-5-sulfonamide;

2-[2-(4-trifluoromethylphenyl)-4-methylcyclopenten-1-yl]pyridine-5-sulfonamide;

2-[2-(4-trifluoromethylphenyl)-4-ethylcyclopenten-1-yl]pyridine-5-sulfonamide;

2-[2-(4-trifluoromethylphenyl)-4-(hydroxymethyl)cyclopenten-1-yl]pyridine-5-sulfonamide;

2-[2-(4-trifluoromethylphenyl)-4-carbomethoxycyclopenten-1-yl]pyridine-5-sulfonamide;

2-[2-(4-trifluoromethylphenyl)-4-fluorocyclopenten-1-yl]pyridine-5-sulfonamide;

2-[2-(4-trifluoromethylphenyl)-4-(trifluoromethyl)cyclopenten-1-yl]pyridine-5-sulfonamide;

2-[2-(4-trifluoromethylphenyl)-4-carboxycyclopenten-1-yl]pyridine-5-sulfonamide;

2-[2-(4-trifluoromethylphenyl)-4-(fluoromethyl)cyclopenten-1-yl]pyridine-5-sulfonamide;

2-[2-(4-fluorophenyl)-4,4-dimethylcyclopenten-1-yl]-5-(methylsulfonyl)pyridine;

2-[2-(4-fluorophenyl)-4,4-diethylcyclopenten-1-yl]-5-(methylsulfonyl)pyridine;

2-[2-(4-fluorophenyl)-4,4-di(hydroxymethyl)cyclopenten-1-yl]-5-(methylsulfonyl)pyridine;

2-[2-(4-fluorophenyl)-4,4-dicarbomethoxycyclopenten-1-yl]-5-(methylsulfonyl)pyridine;

2-[2-(4-fluorophenyl)-4,4-difluorocyclopenten-1-yl]-5-(methylsulfonyl)pyridine;

2-[2-(4-fluorophenyl)-4,4-di(trifluoromethyl)cyclopenten-1-yl]-5-(methylsulfonyl)pyridine;

2-[2-(4-fluorophenyl)-4,4-di(fluoromethyl)cyclopenten-1-yl]-5-(methylsulfonyl)pyridine;

2-[2-(4-trifluoromethylphenyl)-4,4-dimethylcyclopenten-1-yl]-5-(methylsulfonyl)pyridine;

2-[2-(4-trifluoromethylphenyl)-4,4-diethylcyclopenten-1-yl]-5-(methylsulfonyl)pyridine;

2-[2-(4-trifluoromethylphenyl)-4,4-di(hydroxymethyl)cyclopenten-1-yl]-5-(methylsulfonyl)pyridine;

2-[2-(4-trifluoromethylphenyl)-4,4-dicarbomethoxycyclopenten-1-yl]-5-(methylsulfonyl)pyridine;

2-[2-(4-trifluoromethylphenyl)-4,4-difluorocyclopenten-1-yl]-5-(methylsulfonyl)pyridine;

2-[2-(4-trifluoromethylphenyl)-4,4-di(trifluoromethyl)cyclopenten-1-yl]-5-(methylsulfonyl)pyridine;

2-[2-(4-trifluoromethylphenyl)-4,4-di(fluoromethyl)cyclopenten-1-yl]-5-(methylsulfonyl)pyridine;

2-[2-(4-fluorophenyl)-4,4-dimethylcyclopenten-1-yl]pyridine-5-sulfonamide;

2-[2-(4-fluorophenyl)-4,4-diethylcyclopenten-1-yl]pyridine-5-sulfonamide;

2-[2-(4-fluorophenyl)-4,4-di(hydroxymethyl)cyclopenten-1-yl]pyridine-5-sulfonamide;

2-[2-(4-fluorophenyl)-4,4-dicarbomethoxycyclopenten-1-yl]pyridine-5-sulfonamide;

2-[2-(4-fluorophenyl)-4,4-difluorocyclopenten-1-yl]pyridine-5-sulfonamide;

2-[2-(4-fluorophenyl)-4,4-di(trifluoromethyl)cyclopenten-1-yl]pyridine-5-sulfonamide;

2-[2-(4-fluorophenyl)-4,4-di(fluoromethyl)cyclopenten-1-yl]pyridine-5-sulfonamide;

2-[2-(4-trifluoromethylphenyl)-4,4-dimethylcyclopenten-1-yl]pyridine-5-sulfonamide;

2-[2-(4-trifluoromethylphenyl)-4,4-diethylcyclopenten-1-yl]pyridine-5-sulfonamide;

2-[2-(4-trifluoromethylphenyl)-4,4-di(hydroxymethyl)cyclopenten-1-yl]pyridine-5-sulfonamide;

2-[2-(4-trifluoromethylphenyl)-4,4-dicarbomethoxycyclopenten-1-yl]pyridine-5-sulfonamide;

2-[2-(4-trifluoromethylphenyl)-4,4-difluorocyclopenten-1-yl]pyridine-5-sulfonamide;

2-[2-(4-trifluoromethylphenyl)-4,4-di(trifluoromethyl)cyclopenten-1-yl]pyridine-5-sulfonamide; and 2-[2-(4-trifluoromethylphenyl)-4,4-di(fluoromethyl)cyclopenten-1-yl]pyridine-5-sulfonamide.

Within Formula I there is a fourth subclass of compounds of high interest represented by Formula V:

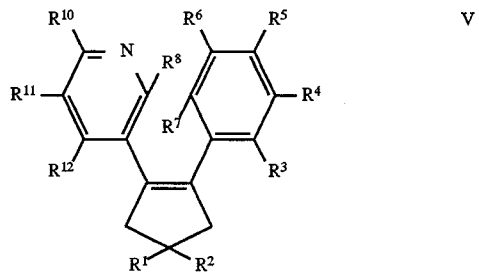

wherein each of $R^1$ and $R^2$ is independently selected from alkyl, hydrido, hydroxyalkyl, halo, haloalkyl, alkoxycarbonyl and carboxyl; and wherein each of $R^3$ through $R^7$, $R^8$, $R^{10}$, $R^{11}$ and $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl;

or a pharmaceutically-acceptable salt thereof.

A preferred class of compounds consists of those compounds of Formula V wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^7$, $R^8$, $R^{10}$, $R^{11}$ and $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl.

A class of compounds of particular interest consists of those compounds of Formula V wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^8$ and $R^{10}$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, trifluoromethylsulfonyl and sulfamyl.

A family of specific compounds of particular interest within Formula V consists of compounds and pharmaceutically-acceptable salts thereof as follows:

1-[2-(2,3-dimethylpyridin-5-yl)cyclopenten-1-yl]-4-(methylsulfonyl)benzene;
1-[2-(3-fluoro-2-methylpyridin-5-yl)cyclopenten-1-yl]-4-(methylsulfonyl)benzene;
1-[2-(3-chloro-2-methylpyridin-5-yl)cyclopenten-1-yl]-4-(methylsulfonyl)benzene;
1-[2-(3-trifluoromethyl-2-methylpyridin-5-yl)cyclopenten-1-yl]-4-(methylsulfonyl)benzene;
1-[2-(3-methoxy-2-methylpyridin-5-yl)cyclopenten-1-yl]-4-(methylsulfonyl)benzene;
1-[2-(2,3-difluoropyridin-5-yl)cyclopenten-1-yl]-4-(methylsulfonyl)benzene;
1-[2-(3-methyl-2-fluoropyridin-5-yl)cyclopenten-1-yl]-4-(methylsulfonyl)benzene;
1-[2-(3-chloro-2-fluoropyridin-5-yl)cyclopenten-1-yl]-4-(methylsulfonyl)benzene;
1-[2-(3-trifluoromethyl-2-fluoropyridin-5-yl)cyclopenten-1-yl]-4-(methylsulfonyl)benzene;
1-[2-(3-methoxy-2-fluoropyridin-5-yl)cyclopenten-1-yl]-4-(methylsulfonyl)benzene;
1-[2-(2,3-dichloropyridin-5-yl)cyclopenten-1-yl]-4-(methylsulfonyl)benzene;
1-[2-(3-methyl-2-chloropyridin-5-yl)cyclopenten-1-yl]-4-(methylsulfonyl)benzene;
1-[2-(3-fluoro-2-chloropyridin-5-yl)cyclopenten-1-yl]-4-(methylsulfonyl)benzene;
1-[2-(3-trifluoromethyl-2-chloropyridin-5-yl)cyclopenten-1-yl]-4-(methylsulfonyl)benzene;
1-[2-(3-methoxy-2-chloropyridin-5-yl)cyclopenten-1-yl]-4-(methylsulfonyl)benzene;
1-[2-(2,3-dimethoxypyridin-5-yl)cyclopenten-1-yl]-4-(methylsulfonyl)benzene;
1-[2-(3-methyl-2-methoxypyridin-5-yl)cyclopenten-1-yl]-4-(methylsulfonyl)benzene;
1-[2-(3-fluoro-2-methoxypyridin-5-yl)cyclopenten-1-yl]-4-(methylsulfonyl)benzene;
1-[2-(3-trifluoromethyl-2-methoxypyridin-5-yl)cyclopenten-1-yl]-4-(methylsulfonyl)benzene;
1-[2-(3-chloro-2-methoxypyridin-5-yl)cyclopenten-1-yl]-4-(methylsulfonyl)benzene;
1-[2-[2,3-di(trifluoromethyl)pyridin-5-yl]cyclopenten-1-yl]-4-(methylsulfonyl)benzene;
1-[2-(3-methyl-2-trifluoromethylpyridin-5-yl)cyclopenten-1-yl]-4-(methylsulfonyl)benzene;
1-[2-(3-fluoro-2-trifluoromethylpyridin-5-yl)cyclopenten-1-yl]-4-(methylsulfonyl)benzene;
1-[2-(3-methoxy-2-trifluoromethylpyridin-5-yl)cyclopenten-1-yl]-4-(methylsulfonyl)benzene;
1-[2-(3-chloro-2-trifluoromethylpyridin-5-yl)cyclopenten-1-yl]-4-(methylsulfonyl)benzene;
1-[2-(3-difluoromethyl-2-methylpyridin-5-yl)cyclopenten-1-yl]-4-(methylsulfonyl)benzene;
1-[2-(3-difluoromethyl-2-fluoropyridin-5-yl)cyclopenten-1-yl]-4-(methylsulfonyl)benzene;
1-[2-(3-difluoromethyl-2-chloropyridin-5-yl)cyclopenten-1-yl]-4-(methylsulfonyl)benzene;
1-[2-(3-difluoromethyl-2-methoxypyridin-5-yl)cyclopenten-1-yl]-4-(methylsulfonyl)benzene;
1-[2-[2,3-di(difluoromethyl) pyridin-5-yl]cyclopenten-1-yl]-4-(methylsulfonyl)benzene;
1-[2-(3-methyl-2-difluoromethylpyridin-5-yl)cyclopenten-1-yl]-4-(methylsulfonyl)benzene;
1-[2-(3-fluoro-2-difluoromethylpyridin-5-yl)cyclopenten-1-yl]-4-(methylsulfonyl)benzene;
1-[2-(3-methoxy-2-difluoromethylpyridin-5-yl)cyclopenten-1-yl]-4-(methylsulfonyl)benzene;
1-[2-(3-chloro-2-difluoromethylpyridin-5-yl)cyclopenten-1-yl]-4-(methylsulfonyl)benzene;

4-[2-(2,3-dimethylpyridin-5-yl)cyclopenten-1-yl]benzenesulfonamide;
4-[2-(3-fluoro-2-methylpyridin-5-yl)cyclopenten-1-yl]benzenesulfonamide;
4-[2-(3-chloro-2-methylpyridin-5-yl)cyclopenten-1-yl]benzenesulfonamide;
4-[2-(3-trifluoromethyl-2-methylpyridin-5-yl)cyclopenten-1-yl]benzenesulfonamide;
4-[2-(3-methoxy-2-methylpyridin-5-yl)cyclopenten-1-yl]benzenesulfonamide;
4-[2-(2,3-difluoropyridin-5-yl)cyclopenten-1-yl]benzenesulfonamide;
4-[2-(3-methyl-2-fluoropyridin-5-yl)cyclopenten-1-yl]benzenesulfonamide;
4-[2-(3-chloro-2-fluoropyridin-5-yl)cyclopenten-1-yl]benzenesulfonamide;
4-[2-(3-trifluoromethyl-2-fluoropyridin-5-yl)cyclopenten-1-yl]benzenesulfonamide;
4-[2-(3-methoxy-2-fluoropyridin-5-yl)cyclopenten-1-yl]benzenesulfonamide;
4-[2-(2,3-dichloropyridin-5-yl)cyclopenten-1-yl]benzenesulfonamide;
4-[2-(3-methyl-2-chloropyridin-5-yl)cyclopenten-1-yl]benzenesulfonamide;
4-[2-(3-fluoro-2-chloropyridin-5-yl)cyclopenten-1-yl]benzenesulfonamide;
4-[2-(3-trifluoromethyl-2-chloropyridin-5-yl)cyclopenten-1-yl]benzenesulfonamide;
4-[2-(3-methoxy-2-chloropyridin-5-yl)cyclopenten-1-yl]benzenesulfonamide;
4-[2-(2,3-dimethoxypyridin-5-yl)cyclopenten-1-yl]benzenesulfonamide;
4-[2-(3-methyl-2-methoxypyridin-5-yl)cyclopenten-1-yl]benzenesulfonamide;
4-[2-(3-fluoro-2-methoxypyridin-5-yl)cyclopenten-1-yl]benzenesulfonamide;
4-[2-(3-trifluoromethyl-2-methoxypyridin-5-yl)cyclopenten-1-yl]benzenesulfonamide;
4-[2-(3-chloro-2-methoxypyridin-5-yl)cyclopenten-1-yl]benzenesulfonamide;
4-[2-[2,3-di(trifluoromethyl)pyridin-5-yl]cyclopenten-1-yl]benzenesulfonamide;
4-[2-(3-methyl-2-trifluoromethylpyridin-5-yl)cyclopenten-1-yl]benzenesulfonamide;
4-[2-(3-fluoro-2-trifluoromethylpyridin-5-yl)cyclopenten-1-yl]benzenesulfonamide;
4-[2-(3-methoxy-2-trifluoromethylpyridin-5-yl)cyclopenten-1-yl]benzenesulfonamide;
4-[2-(3-chloro-2-trifluoromethylpyridin-5-yl)cyclopenten-1-yl]benzenesulfonamide;
4-[2-(3-difluoromethyl-2-methylpyridin-5-yl)cyclopenten-1-yl]benzenesulfonamide;
4-[2-(3-difluoromethyl-2-fluoropyridin-5-yl)cyclopenten-1-yl]benzenesulfonamide;
4-[2-(3-difluoromethyl-2-chloropyridin-5-yl)cyclopenten-1-yl]benzenesulfonamide;
4-[2-(3-difluoromethyl-2-methoxypyridin-5-yl)cyclopenten-1-yl]benzenesulfonamide;
4-[2-(3-di(difluoromethyl)pyridin-5-yl]cyclopenten-1-yl]benzenesulfonamide;
4-[2-(3-methyl-2-difluoromethylpyridin-5-yl)cyclopenten-1-yl]benzenesulfonamide;
4-[2-(3-fluoro-2-difluoromethylpyridin-5-yl)cyclopenten-1-yl]benzenesulfonamide;
4-[2-(3-methoxy-2-difluoromethylpyridin-5-yl)cyclopenten-1-yl]benzenesulfonamide;
4-[2-(3-chloro-2-difluoromethylpyridin-5-yl)cyclopenten-1-yl]benzenesulfonamide;

5-[2-[4-(methylsulfonyl)phenyl]cyclopenten-1-yl]pyridine;

2-fluoro-5-[2-[4-(methylsulfonyl)phenyl]cyclopenten-1-yl]pyridine;

2-chloro-5-[2-[4-(methylsulfonyl)phenyl]cyclopenten-1-yl]pyridine;

2-methyl-5-[2-[4-(methylsulfonyl)phenyl]cyclopenten-1-yl]pyridine;

2-cyano-5-[2-[4-(methylsulfonyl)phenyl]cyclopenten-1-yl]pyridine;

2-trifluoromethyl-5-[2-[4-(methylsulfonyl)phenyl]cyclopenten-1-yl]pyridine;

4-[2-(pyridin-5-yl)cyclopenten-1-yl]benzenesulfonamide;

4-[2-(2-fluoropyridin-5-yl)cyclopenten-1-yl]benzenesulfonamide;

4-[2-(2-chloropyridin-5-yl)cyclopenten-1-yl]benzenesulfonamide;

4-[2-(2-methylpyridin-5-yl)cyclopenten-1-yl]benzenesulfonamide;

4-[2-(2-cyanopyridin-5-yl)cyclopenten-1-yl]benzenesulfonamide;

4-[2-(2-trifluoromethylpyridin-5-yl)cyclopenten-1-yl]benzenesulfonamide;

2-fluoro-5-[2-[4-(methylsulfonyl)phenyl]-4-methylcyclopenten-1-yl]pyridine;

2-fluoro-5-[2-[4-(methylsulfonyl)phenyl]-4-ethylcyclopenten-1-yl]pyridine 2-fluoro-5-[2-[4-(methylsulfonyl)phenyl]-4-(hydroxymethyl)cyclopenten-1-yl]pyridine;

2-fluoro-5-[2-[4-(methylsulfonyl)phenyl]-4-carbomethoxycyclopenten-1-yl]pyridine;

2-fluoro-5-[2-[4-(methylsulfonyl)phenyl]-4-fluorocyclopenten-1-yl]pyridine;

2-fluoro-5-[2-[4-(methylsulfonyl)phenyl]-4-(trifluoromethyl)cyclopenten-1-yl]pyridine;

2-fluoro-5-[2-[4-(methylsulfonyl)phenyl]-4-carboxycyclopenten-1-yl]pyridine;

2-fluoro-5-[2-[4-(methylsulfonyl)phenyl]-4-(fluoromethyl)cyclopenten-1-yl]pyridine;

2-trifluoromethyl-5-[2-[4-(methylsulfonyl)phenyl]-4-methylcyclopenten-1-yl]pyridine;

2-trifluoromethyl-5-[2-[4-(methylsulfonyl)phenyl]-4-ethylcyclopenten-1-yl]pyridine;

2-trifluoromethyl-5-[2-[4-(methylsulfonyl)phenyl]-4-(hydroxymethyl)cyclopenten-1-yl]pyridine;

2-trifluoromethyl-5-[2-[4-(methylsulfonyl)phenyl]-4-carbomethoxycyclopenten-1-yl]pyridine;

2-trifluoromethyl-5-[2-[4-(methylsulfonyl)phenyl]-4-fluorocyclopenten-1-yl]pyridine;

2-trifluoromethyl-5-[2-[4-(methylsulfonyl)phenyl]-4-(trifluoromethyl)cyclopenten-1-yl]pyridine;

2-trifluoromethyl-5-[2-[4-(methylsulfonyl)phenyl]-4-carboxycyclopenten-1-yl]pyridine;

2-trifluoromethyl-5-[2-[4-(methylsulfonyl)phenyl]-4-(fluoromethyl)cyclopenten-1-yl]pyridine;

4-[2-(2-fluoropyridin-5-yl)-4-methylcyclopenten-1-yl]benzenesulfonamide;

4-[2-(2-fluoropyridin-5-yl)-4-ethylcyclopenten-1-yl]benzenesulfonamide;

4-[2-(2-fluoropyridin-5-yl)-4-(hydroxymethyl)cyclopenten-1-yl]benzenesulfonamide;

4-[2-(2-fluoropyridin-5-yl)-4-carbomethoxycyclopenten-1-yl]benzenesulfonamide;

4-[2-(2-fluoropyridin-5-yl)-4-fluorocyclopenten-1-yl]benzenesulfonamide;

4-[2-(2-fluoropyridin-5-yl)-4-(trifluoromethyl)cyclopenten-1-yl]benzenesulfonamide;

4-[2-(2-fluoropyridin-5-yl)-4-carboxycyclopenten-1-yl]benzenesulfonamide;

4-[2-(2-fluoropyridin-5-yl)-4-(fluoromethyl)cyclopenten-1-yl]benzenesulfonamide;

4-[2-(2-trifluoromethyl-5-[2-[4-(methylsulfonyl)phenyl]-4,4-dimethylcyclopenten-1-yl]pyridine;

4-[2-(2-trifluoromethyl-5-[2-[4-(methylsulfonyl)phenyl]-4,4-diethylcyclopenten-1-yl]pyridine;

4-[2-(2-trifluoromethyl-5-[2-[4-(methylsulfonyl)phenyl]-4,4-di(hydroxymethyl)cyclopenten-1-yl]pyridine;

4-[2-(2-trifluoromethyl-5-[2-[4-(methylsulfonyl)phenyl]-4,4-dicarbomethoxycyclopenten-1-yl]pyridine;

4-[2-(2-trifluoromethyl-5-[2-[4-(methylsulfonyl)phenyl]-4,4-difluorocyclopenten-1-yl]pyridine;

4-[2-(2-trifluoromethyl-5-[2-[4-(methylsulfonyl)phenyl]-4,4-di(trifluoromethyl)cyclopenten-1-yl]pyridine;

4-[2-(2-trifluoromethyl-5-[2-[4-(methylsulfonyl)phenyl]-4,4-dicarboxycyclopenten-1-yl]pyridine;

4-[2-(2-trifluoromethyl-5-[2-[4-(methylsulfonyl)phenyl]-4,4-difluoromethylcyclopenten-1-yl]pyridine;

2-fluoro-5-[2-[4-(methylsulfonyl)phenyl]-4,4-dimethylcyclopenten-1-yl]pyridine;

2-fluoro-5-[2-[4-(methylsulfonyl)phenyl]-4,4-diethylcyclopenten-1-yl]pyridine;

2-fluoro-5-[2-[4-(methylsulfonyl)phenyl]-4,4-di(hydroxymethyl)cyclopenten-1-yl]pyridine;

2-fluoro-5-[2-[4-(methylsulfonyl)phenyl]-4,4-dicarbomethoxycyclopenten-1-yl]pyridine;

2-fluoro-5-[2-[4-(methylsulfonyl)phenyl]-4,4-difluorocyclopenten-1-yl]pyridine;

2-fluoro-5-[2-[4-(methylsulfonyl)phenyl]-4,4-di(trifluoromethyl)cyclopenten-1-yl]pyridine;

2-fluoro-5-[2-[4-(methylsulfonyl)phenyl]-4,4-di(fluoromethyl)cyclopenten-1-yl]pyridine;

2-trifluoromethyl-5-[2-[4-(methylsulfonyl)phenyl]-4,4-dimethylcyclopenten-1-yl]pyridine;

2-trifluoromethyl-5-[2-[4-(methylsulfonyl)phenyl]-4,4-diethylcyclopenten-1-yl]pyridine;

2-trifluoromethyl-5-[2-[4-(methylsulfonyl)phenyl]-4,4-di(hydroxymethyl)cyclopenten-1-yl]pyridine;

2-trifluoromethyl-5-[2-[4-(methylsulfonyl)phenyl]-4,4-dicarbomethoxycyclopenten-1-yl]pyridine;

2-trifluoromethyl-5-[2-[4-(methylsulfonyl)phenyl]-4,4-difluorocyclopenten-1-yl]pyridine;

2-trifluoromethyl-5-[2-[4-(methylsulfonyl)phenyl]-4,4-di(trifluoromethyl)cyclopenten-1-yl]pyridine;

2-trifluoromethyl-5-[2-[4-(methylsulfonyl)phenyl]-4,4-di(fluoromethyl)cyclopenten-1-yl]pyridine;

4-[2-(2-fluoropyridin-5-yl)-4,4-dimethylcyclopenten-1-yl]benzenesulfonamide;

4-[2-(2-fluoropyridin-5-yl)-4,4-diethylcyclopenten-1-yl]benzenesulfonamide;

4-[2-(2-fluoropyridin-5-yl)-4,4-di(hydroxymethyl)cyclopenten-1-yl]benzenesulfonamide;

4-[2-(2-fluoropyridin-5-yl)-4,4-dicarbomethoxycyclopenten-1-yl]benzenesulfonamide;

4-[2-(2-fluoropyridin-5-yl)-4,4-difluorocyclopenten-1-yl]benzenesulfonamide;

4-[2-(2-fluoropyridin-5-yl)-4,4-di(trifluoromethyl)cyclopenten-1-1]benzene sulfonamide;

4-[2-(2-fluoropyridin-5-yl)-4,4-di(fluoromethyl)cyclopenten-1-yl]benzenesulfonamide;

4-[2-(2-trifluoromethylpyridin-5-yl)-4,4-dimethylcyclopenten-1-yl]benzenesulfonamide;

4-[2-(2-trifluoromethylpyridin-5-yl)-4,4-diethylcyclopenten-1-yl]benzenesulfonamide;

4-[2-(2-trifluoromethylpyridin-5-yl)-4,4-di(hydroxymethyl)cyclopenten-1-yl]benzenesulfonamide;

4-[2-(2-trifluoromethylpyridin-5-yl)-4,4-dicarbomethoxycyclopenten-1-yl]benzenesulfonamide;

4-[2-(2-trifluoromethylpyridin-5-yl)-4,4-difluorocyclopenten-1-yl]benzenesulfonamide;

4-[2-(2-trifluoromethylpyridin-5-yl)-4,4-di(trifluoromethyl)cyclopenten-1-1]benzenesulfonamide;

4-[2-(2-trifluoromethylpyridin-5-yl)-4,4-di(fluoromethyl)cyclopenten-1-yl]benzenesulfonamide;

5-(2-phenylcyclopenten-1-yl)-2-(methylsulfonyl)pyridine;

5-[2-(4-fluorophenyl)cyclopenten-1-yl]-2-(methylsulfonyl)pyridine;

5-[2-(4-chlorophenyl)cyclopenten-1-yl]-2-(methylsulfonyl)pyridine;

5-[2-(4-methylphenyl)cyclopenten-1-yl]-2-(methylsulfonyl)pyridine;

5-[2-(4-cyanophenyl)cyclopenten-1-yl]-2-(methylsulfonyl)pyridine;

5-[2-(4-trifluoromethylphenyl)cyclopenten-1-yl]-2-(methylsulfonyl)pyridine;

5-(2-phenylcyclopenten-1-yl)pyridine-2-sulfonamide;

5-[2-(4-fluorophenyl)cyclopenten-1-yl]pyridine-2-sulfonamide;

5-[2-(4-chlorophenyl)cyclopenten-1-yl]pyridine-2-sulfonamide;

5-[2-(4-methylphenyl)cyclopenten-1-yl]pyridine-2-sulfonamide;

5-[2-(4-cyanophenyl)cyclopenten-1-yl]pyridine-2-sulfonamide;

5-[2-(4-trifluoromethylphenyl)cyclopenten-1-yl]pyridine-2-sulfonamide;

5-[2-(4-fluorophenyl)-4-methylcyclopenten-1-yl]-2-(methylsulfonyl)pyridine;

5-[2-(4-fluorophenyl)-4-ethylcyclopenten-1-yl]-2-(methylsulfonyl)pyridine;

5-[2-(4-fluorophenyl)-4-(hydroxymethyl)cyclopenten-1-yl]-2-(methylsulfonyl)pyridine;

5-[2-(4-fluorophenyl)-4-carbomethoxycyclopenten-1-yl]-2-(methylsulfonyl)pyridine;

5-[2-(4-fluorophenyl)-4-fluorocyclopenten-1-yl]-2-(methylsulfonyl)pyridine;

5-[2-(4-fluorophenyl)-4-(trifluoromethyl)cyclopenten-1-yl]-2-(methylsulfonyl)pyridine;

5-[2-(4-fluorophenyl)-4-carboxycyclopenten-1-yl]-2-(methylsulfonyl)pyridine;

5-[2-(4-fluorophenyl)-4-(fluoromethyl)cyclopenten-1-yl]-2-(methylsulfonyl)pyridine;

5-[2-(4-trifluoromethylphenyl)-4-methylcyclopenten-1-yl]-2-(methylsulfonyl)pyridine;

5-[2-(4-trifluoromethylphenyl)-4-ethylcyclopenten-1-yl]-2-(methylsulfonyl)pyridine;

5-[2-(4-trifluoromethylphenyl)-4-(hydroxymethyl)cyclopenten-1-yl]-2-(methylsulfonyl)pyridine;

5-[2-(4-trifluoromethylphenyl)-4-carbomethoxycyclopenten-1-yl]-2-(methylsulfonyl)pyridine;

5-[2-(4-trifluoromethylphenyl)-4-fluorocyclopenten-1-yl]-2-(methylsulfonyl)pyridine;

5-[2-(4-trifluoromethylphenyl)-4-(trifluoromethyl)cyclopenten-1-yl]-2-(methylsulfonyl)pyridine;

5-[2-(4-trifluoromethylphenyl)-4-carboxycyclopenten-1-yl]-2-(methylsulfonyl)pyridine;

5-[2-(4-trifluoromethylphenyl)-4-(fluoromethyl)cyclopenten-1-yl]-2-(methylsulfonyl)pyridine;

5-[2-(4-fluorophenyl)-4-methylcyclopenten-1-yl]pyridine-2-sulfonamide;

5-[2-(4-fluorophenyl)-4-ethylcyclopenten-1-yl]pyridine-2-sulfonamide;

5-[2-(4-fluorophenyl)-4-(hydroxymethyl)cyclopenten-1-yl]pyridine-2-sulfonamide;

5-[2-(4-fluorophenyl)-4-carbomethoxycyclopenten-1-yl]pyridine-2-sulfonamide;

5-[2-(4-fluorophenyl)-4-fluorocyclopenten-1-yl]pyridine-2-sulfonamide;

5-[2-(4-fluorophenyl)-4-(trifluoromethyl)cyclopenten-1-yl]pyridine-2-sulfonamide;

5-[2-(4-fluorophenyl)-4-carboxycyclopenten-1-yl]pyridine-2-sulfonamide;

5-[2-(4-fluorophenyl)-4-(fluoromethyl)cyclopenten-1-yl]pyridine-2-sulfonamide;

5-[2-(4-trifluoromethylphenyl)-4-methylcyclopenten-1-yl]pyridine-2-sulfonamide;

5-[2-(4-trifluoromethylphenyl)-4-ethylcyclopenten-1-yl]pyridine-2-sulfonamide;

5-[2-(4-trifluoromethylphenyl)-4-(hydroxymethyl)cyclopenten-1-yl]pyridine-2-sulfonamide;

5-[2-(4-trifluoromethylphenyl)-4-carbomethoxycyclopenten-1-yl]pyridine-2-sulfonamide;

5-[2-(4-trifluoromethylphenyl)-4-fluorocyclopenten-1-yl]pyridine-2-sulfonamide;

5-[2-(4-trifluoromethylphenyl)-4-(trifluoromethyl)cyclopenten-1-yl]pyridine-2-sulfonamide;

5-[2-(4-trifluoromethylphenyl)-4-carboxycyclopenten-1-yl]pyridine-2-sulfonamide;

5-[2-(4-trifluoromethylphenyl)-4-(fluoromethyl)cyclopenten-1-yl]pyridine-2-sulfonamide;

5-[2-(4-fluorophenyl)-4,4-dimethylcyclopenten-1-yl]-2-(methylsulfonyl)pyridine;

5-[2-(4-fluorophenyl)-4,4-diethylcyclopenten-1-yl]-2-(methylsulfonyl)pyridine;

5-[2-(4-fluorophenyl)-4,4-di(hydroxymethyl)cyclopenten-1-yl]-2-(methylsulfonyl)pyridine;

5-[2-(4-fluorophenyl)-4,4-dicarbomethoxycyclopenten-1-yl]-2-(methylsulfonyl)pyridine;

5-[2-(4-fluorophenyl)-4,4-difluorocyclopenten-1-yl]-2-(methylsulfonyl)pyridine;

5-[2-(4-fluorophenyl)-4,4-di(trifluoromethyl)cyclopenten-1-yl]-2-(methylsulfonyl)pyridine;

5-[2-(4-fluorophenyl)-4,4-di(fluoromethyl)cyclopenten-1-yl]-2-(methylsulfonyl)pyridine;

5-[2-(4-trifluoromethylphenyl)-4,4-dimethylcyclopenten-1-yl]-2-(methylsulfonyl)pyridine;

5-[2-(4-trifluoromethylphenyl)-4,4-diethylcyclopenten-1-yl]-2-(methylsulfonyl)pyridine;

5-[2-(4-trifluoromethylphenyl)-4,4-di(hydroxymethyl)cyclopenten-1-yl]-2-(methylsulfonyl)pyridine;

5-[2-(4-trifluoromethylphenyl)-4,4-dicarbomethoxycyclopenten-1-yl]-2-(methylsulfonyl)pyridine;

5-[2-(4-trifluoromethylphenyl)-4,4-difluorocyclopenten-1-yl]-2-(methylsulfonyl)pyridine;

5-[2-(4-trifluoromethylphenyl)-4,4-di(trifluoromethyl)cyclopenten-1-yl]-2-(methylsulfonyl)pyridine;

5-[2-(4-trifluoromethylphenyl)-4,4-di(fluoromethyl)cyclopenten-1-yl]-2-(methylsulfonyl)pyridine;

5-[2-(4-fluorophenyl)-4,4-dimethylcyclopenten-1-yl]pyridine-2-sulfonamide;

5-[2-(4-fluorophenyl)-4,4-diethylcyclopenten-1-yl]pyridine-2-sulfonamide;

5-[2-(4-fluorophenyl)-4,4-di(hydroxymethyl)cyclopenten-1-yl]pyridine-2-sulfonamide;

5-[2-(4-fluorophenyl)-4,4-dicarbomethoxycyclopenten-1-yl]pyridine-2-sulfonamide;

5-[2-(4-fluorophenyl)-4,4-difluorocyclopenten-1-yl]pyridine-2-sulfonamide;

5-[2-(4-fluorophenyl)-4,4-di(trifluoromethyl)cyclopenten-1-yl]pyridine-2-sulfonamide;

5-[2-(4-fluorophenyl)-4,4-di(fluoromethyl)cyclopenten-1-yl]pyridine-2-sulfonamide;

5-[2-(4-trifluoromethylphenyl)-4,4-dimethylcyclopenten-1-yl]pyridine-2-sulfonamide;

5-[2-(4-trifluoromethylphenyl)-4,4-diethylcyclopenten-1-yl]pyridine-2-sulfonamide;

5-[2-(4-trifluoromethylphenyl)-4,4-di(hydroxymethyl)cyclopenten-1-yl]pyridine-2-sulfonamide;

5-[2-(4-trifluoromethylphenyl)-4,4-dicarbomethoxycyclopenten-1-yl]pyridine-2-sulfonamide;

5-[2-(4-trifluoromethylphenyl)-4,4-difluorocyclopenten-1-yl]pyridine-2-sulfonamide;

5-[2-(4-trifluoromethylphenyl)-4,4-di(trifluoromethyl)cyclopenten-1-yl]pyridine-2-sulfonamide; and 5-[2-(4-trifluoromethylphenyl)-4,4-di(fluoromethyl)cyclopenten-1-yl]pyridine-2-sulfonamide.

Within Formula I there is a fifth subclass of compounds of high interest represented by Formula VI:

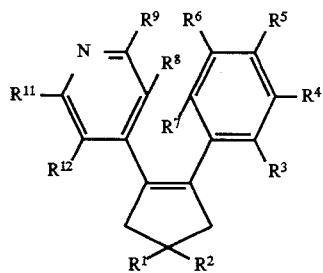

wherein each of $R^1$ and $R^2$ is independently selected from alkyl, hydrido, hydroxyalkyl, halo, haloalkyl, alkoxycarbonyl and carboxyl;

wherein $R^5$ is selected from alkylsulfonyl, haloalkylsulfonyl and sulfamyl; and wherein each of $R^3$, $R^4$, $R^6$, $R^7$, $R^8$, $R^9$, $R^{11}$ and $R^{12}$ is independently selected from hydrido, halo, alkyl, alkylthio, cyano, haloalkyl, alkoxy, haloalkoxy, hydroxyalkyl and alkoxyalkyl; or a pharmaceutically-acceptable salt thereof.

A preferred class of compounds consists of those compounds of Formula VI wherein each of $R^1$ and $R^2$ is independently selected from lower alkyl, hydrido, lower hydroxyalkyl, halo, lower haloalkyl, lower alkoxycarbonyl and carboxyl; wherein $R^5$ is selected from lower alkylsulfonyl, lower haloalkylsulfonyl and sulfamyl; and wherein each of $R^3$, $R^4$, $R^6$, $R^7$, $R^8$, $R^9$, $R^{11}$ and $R^{12}$ is independently selected from hydrido, halo, lower alkyl, lower alkylthio, cyano, lower haloalkyl, lower alkoxy, lower haloalkoxy, lower hydroxyalkyl and lower alkoxyalkyl.

A class of compounds of particular interest consists of those compounds of Formula VI wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; wherein $R^5$ is selected from methylsulfonyl, ethylsulfonyl, trifluoromethylsulfonyl and sulfamyl; and wherein each of $R^3$, $R^4$, $R^6$, $R^7$, $R^8$, $R^9$, $R^{11}$ and $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, trifluoromethylsulfonyl and sulfamyl.

A family of specific compounds of particular interest within Formula VI consists of compounds and pharmaceutically-acceptable salts thereof as follows:

4-[2-[4-(methylsulfonyl)phenyl]cyclopenten-1-yl]pyridine;
4-[2-(4-pyridinyl)cyclopenten-1-yl]benzenesulfonamide;
4-[2-[4-(methylsulfonyl)phenyl]-4,4-dimethylcyclopenten-1-yl]pyridine;
4-[2-[4-(methylsulfonyl)phenyl]-4,4-diethylcyclopenten-1-yl]pyridine;
4-[2-[4-(methylsulfonyl)phenyl]-4,4-di(hydroxymethyl)cyclopenten-1-yl]pyridine;
4-[2-[4-(methylsulfonyl)phenyl]-4,4-dicarbomethoxycyclopenten-1-yl]pyridine;
4-[2-[4-(methylsulfonyl)phenyl]-4,4-difluorocyclopenten-1-yl]pyridine;
4-[2-[4-(methylsulfonyl)phenyl]-4,4-di(trifluoromethyl)cyclopenten-1-yl]pyridine;
4-[2-[4-(methylsulfonyl)phenyl]-4,4-di(fluoromethyl)cyclopenten-1-yl]pyridine;
4-[2-[4-(pyridinyl)phenyl]-4,4-dimethylcyclopenten-1-yl]benzenesulfonamide;
4-[2-[4-(pyridinyl)phenyl]-4,4-diethylcyclopenten-1-yl]benzenesulfonamide;
4-[2-[4-(pyridinyl)phenyl]-4,4-di(hydroxymethyl)cyclopenten-1-yl]benzenesulfonamide;
4-[2-[4-(pyridinyl)phenyl]-4,4-dicarbomethoxycyclopenten-1-yl]benzenesulfonamide;
4-[2-[4-(pyridinyl)phenyl]-4,4-difluorocyclopenten-1-yl]benzenesulfonamide;
4-[2-[4-(pyridinyl)phenyl]-4,4-di(trifluoromethyl)cyclopenten-1-yl]benzenesulfonamide; and
4-[2-[4-(pyridinyl)phenyl]-4,4-di(fluoromethyl)cyclopenten-1-yl]benzenesulfonamide.

Where used, either alone or within other terms such as "haloalkyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. Examples of such radicals include methyl, ethyl, n-propyl, isopropyl, n-butyl, isobutyl, sec-butyl, tert-butyl, pentyl, iso-amyl, hexyl, octyl and the like. The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either a bromo, chloro or a fluoro atom within the radical. Dihalo and polyhaloalkyl radicals may have two or more of the same halo atoms or a combination of different halo radicals. More preferred haloalkyl radicals are "lower haloalkyl" radicals having one to six carbon atoms. Examples of such lower haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms. Examples of such lower hhydroxyalkyl radicals include hydroxymethyl, 2-hydroxyethyl, 4-hydroxybutyl and 6-hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such lower alkoxy radicals include methoxy, ethoxy, propoxy, butoxy, isopropoxy, tert-butoxy and methylenedioxy. The term "alkoxyalkyl" also embraces alkyl radicals having two or more alkoxy radicals attached to the alkyl radical, that is, to form monoalkoxyalkyl and dialkoxyalkyl radicals. More preferred alkoxyalkyl radicals are "lower alkoxyalkyl" radicals having alkyl radicals of one to six carbon atoms. Examples of such lower alkoxyalkyl radicals include methoxymethyl, methoxyethyl and the like. The "alkoxy" or "alkoxyalkyl" radicals may be further substituted with one or more halo atoms, such as fluoro, chloro or bromo, to provide haloalkoxy or haloalkoxyalkyl radicals. The term "alkylthio" embraces radicals containing a linear or branched alkyl radical, of one to about ten carbon atoms attached to a divalent sulfur atom, such as a methythio radical. More preferred alkylthio radicals are "lower alkylthio" radicals having alkyl radicals of one to six carbon atoms. Examples of such lower alkylthio radicals include methylthio, ethylthio, propylthio, butylthio and hexylthio. The term "aryl" embraces aromatic radicals such as phenyl, naphthyl and biphenyl. Preferred aryl radicals are those consisting of one, two, or three benzene rings. The term "sulfonyl", whether used alone or linked to other terms such as alkylsulfonyl, denotes respectively divalent radicals —SO$_2$—. "Alkylsulfonyl" embraces alkyl radicals attached to a sulfonyl radical, where alkyl is defined as above. More preferred alkylsulfonyl radicals are "lower alkylsulfonyl" radicals having alkyl radicals of one to six carbon atoms. Examples of such lower alkylsulfonyl radicals include methylsulfonyl and ethylsulfonyl. The term "haloalkylsulfonyl" embraces haloalkyl radicals attached to a sulfonyl radical, where haloalkyl and alkyl are defined as above. More preferred haloalkylsulfonyl radicals are "lower haloalkylsulfonyl" radicals having lower haloalkyl radicals as described above. Examples of such lower haloalkylsulfonyl radicals include fluoromethylsulfonyl and trifluoromethylsulfonyl. The terms "sulfamyl" or "sulfonamidyl" denotes a sulfonyl radical substituted with an amine radical, forming a sulfonamide (—SO$_2$NH$_2$). The term "carboxyl", whether used alone or with other terms, denotes —CO$_2$H. The term "alkoxycarbonyl" means a radical containing an alkoxy radical, as defined above, attached via a carbon atom to a "carbonyl" radical (C=O). More preferred alkoxycarbonyl radicals are "lower alkoxycarbonyl" radicals having lower alkoxy radicals as described above. Examples of such "lower alkoxycarbonyl" radicals include methoxycarbonyl, ethoxycarbonyl, isopropoxycarbonyl, tertbutoxycarbonyl, propoxycarbonyl, butoxycarbonyl, isobutoxycarbonyl, pentoxycarbonyl and tert-butoxycarbonyl ((CH$_3$)$_3$CO$_2$C—).

The present invention comprises a pharmaceutical composition for the treatment of inflammation and inflammation-associated disorders, such as arthritis, comprising a therapeutically-effective amount of a compound of Formula I in association with at least one pharmaceutically-acceptable carrier, adjuvant or diluent.

The present invention also comprises a therapeutic method of treating inflammation or inflammation-associated disorders in a subject, the method comprising administering to a subject having such inflammation or disorder a therapeutically-effective amount of a compound of Formula I.

Also included in the family of compounds of Formula I are isomeric forms including diastereoisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I–XXII, wherein the R$^1$–R$^{12}$ substituents are as defined for Formula I, above, except where further noted.

Scheme I

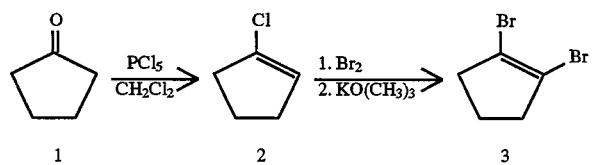

Synthetic Scheme I shows the preparation of 1,2-dibromocyclopentene (3) in two steps from commercially available cyclopentanone (1) using a procedure similar to the one developed by Montgomery, et al., [*J. Am. Chem. Soc.*, 87, 1917 (1965)]. In step one, chlorination with phosphorus pentachloride gives 1-chlorocyclopentene (2). In step two, bromination of 2, followed by the elimination of hydrogen chloride on treatment with potassium tert-butoxide, provides 3.

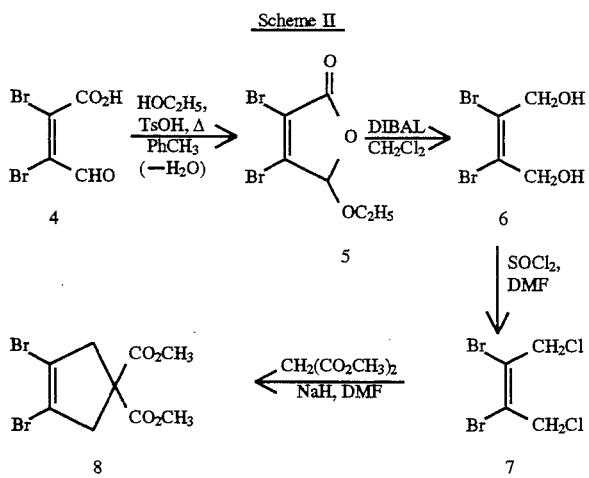

Synthetic Scheme II shows the preparation of 1,2-dibromo-4,4-dicarbomethoxycyclopentene (8) in four steps from commercially available mucobromic acid (4) using a procedure similar to the one developed by Lerstrub, et al., [*Syn. Metals*, 19, 647 (1987)]. In step one, mucobromic acid is converted to its ethyl ester 5 on treatment with ethanol in toluene at reflux in the presence of p-toluenesulfonic acid (TsOH). In step two, reduction of 5 with diisobutylaluminum hydride (DIBAL) in methylene chloride gives the diol 6. In step three, the diol 6 is reacted with thionyl chloride in dimethylformamide (DMF) to give the corresponding dichloride 7. In step four, the dichloride 7 is dialkylated with the dianion of methyl malonate to give 8.

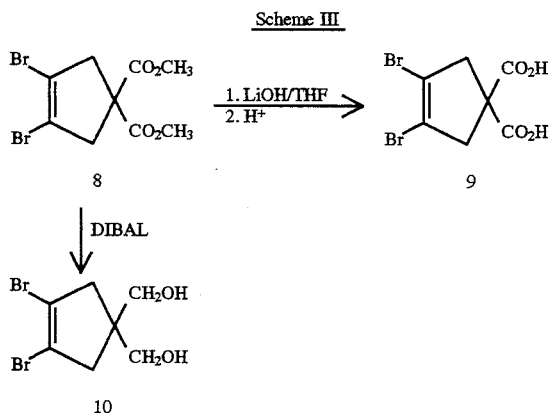

Synthetic Scheme III shows the preparation of 1,2-dibromo-4,4-dicarboxycyclopentene (9) and 1,2-bromo-4,4-di(hydroxymethyl)cyclopentene (10) from synthetic intermediate 8 (prepared in Synthetic Scheme II). Reaction of 8 with lithium hydroxide in tetrahydrofuran (THF) followed by careful acidification at 0° C. gives the diacid 9; treatment with DIBAL gives the corresponding diol 10.

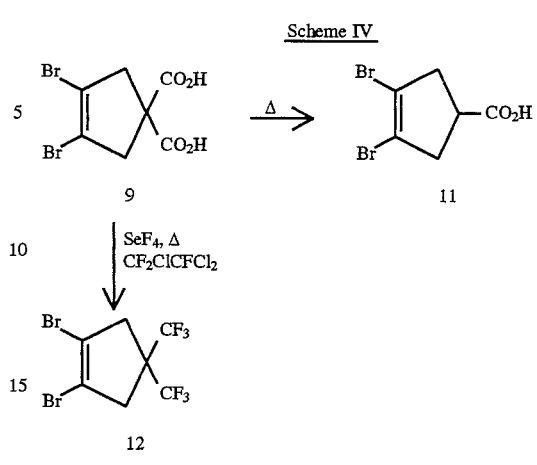

Synthetic Scheme IV shows the preparation of 1,2-dibromo-4-carboxycyclopentene (11) and 1,2-dibromo-4,4-bis(trifluoromethyl)cyclopentene (12) from synthetic intermediate 9 (prepared in Synthetic Scheme III). On heating, the diacid 9 is converted to the monoacid 11; treatment with selenium tetrafluoride in 1,1,2-trichlorotrifluoroethane at reflux gives the bistrifluoromethyl analog 12.

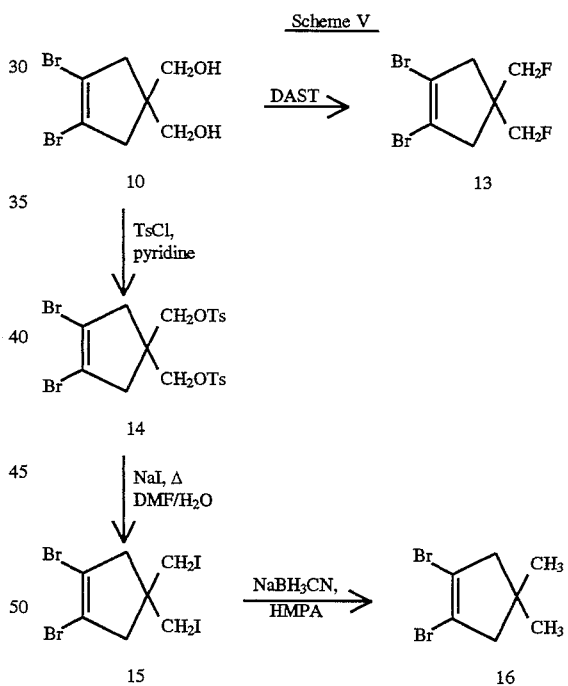

Synthetic Scheme V shows the preparation of 1,2-dibromo-4,4-di(fluoromethyl)cyclopentene (13) and 1,2-dibromo-4,4-dimethylcyclopentene (16) from synthetic intermediate 10 (prepared in Synthetic Scheme III). Treatment of the diol 10 with diethylaminosulfurtrifluoride (DAST) in methylene chloride gives the corresponding fluoromethyl analog 13. Reaction of 10 with p-toluenesulfonyl chloride (TsCl) in the presence of pyridine gives the ditosylate 14. Reaction of 14 with sodium iodide in DMF/water (3:1) at 150° C. gives the di(iodomethyl) analog 15 which is subsequently reduced with sodium cyanoborohydride to give the dimethyl analog 16.

Scheme VI

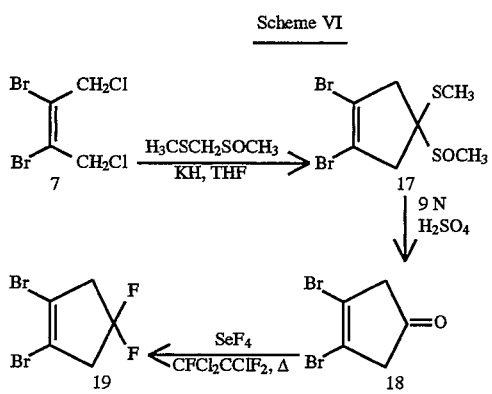

Synthetic Scheme VI shows the preparation of 1,2-dibromo-4,4-difluorocyclopentene (19) from synthetic intermediate 7 (prepared in Synthetic Scheme II). Using a procedure similar to the one developed by Ogura, et al., [*Tetrahedron Lett.*, 32, 2767 (1975)], the dianion of methyl methylthiomethyl sulfoxide (generated by potassium hydride in THF) is reacted with 7 to give the dimethyl dithioacetal S-oxide 17. Subsequent hydrolysis with 9N sulfuric acid gives the corresponding ketone 18. Reaction of with selenium tetrafluoride in 1,1,2-trichlorotrifluoroethane at reflux gives the 4,4-difluoro analog 19.

Scheme VII

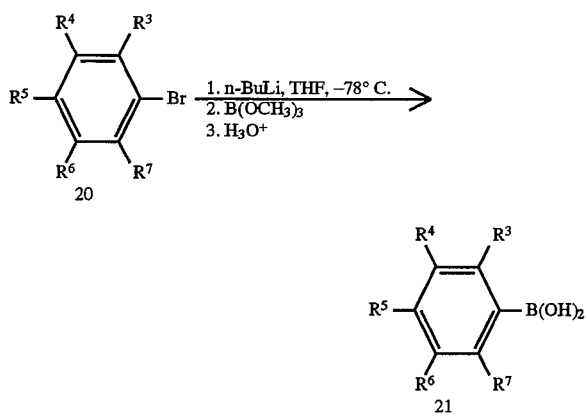

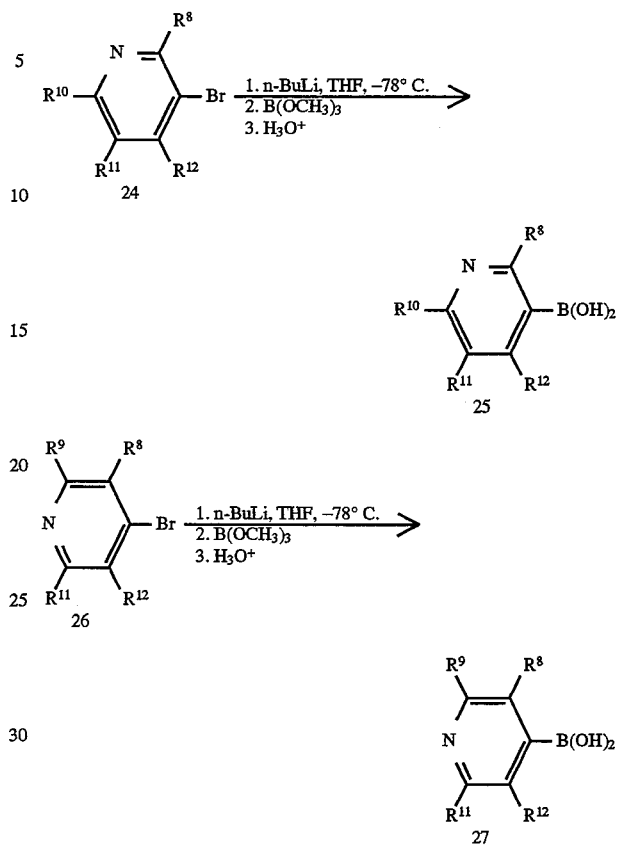

Synthetic Scheme VII shows the preparation of the prerequisite substituted phenylboronic acids 21 and substituted pyridinylboronic acids 23, 25, and 27 from the available bromides 20, 22, 24, and 26 respectively. Halogen-metal interchange in THF at −78° C. generates the corresponding organolithium reagents which are reacted with trimethyl borate. Hydrolysis with 3N hydrochloric acid provides the substituted phenylboronic acids 21 and the substituted pyridinylboronic acids 23, 25, and 27, respectively.

Scheme VIII

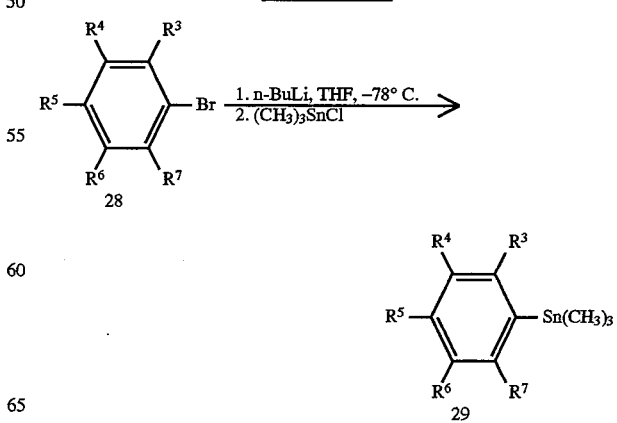

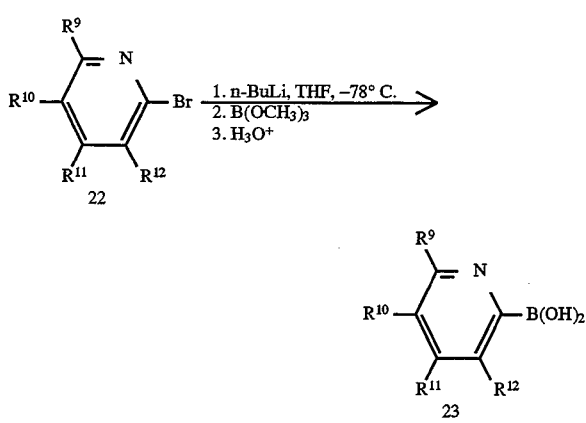

-continued
Scheme VIII

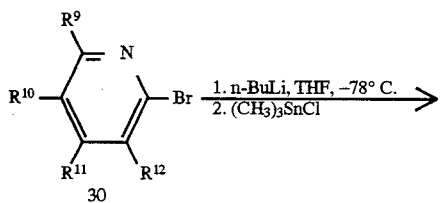

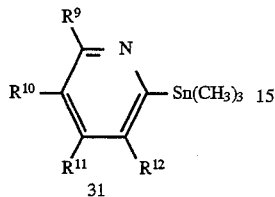

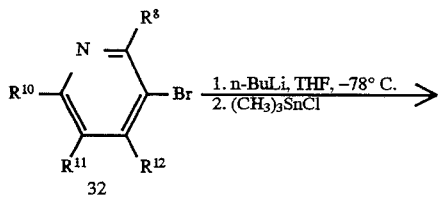

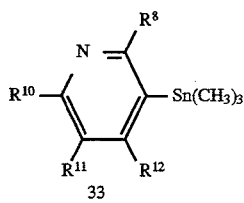

-continued
Scheme VIII

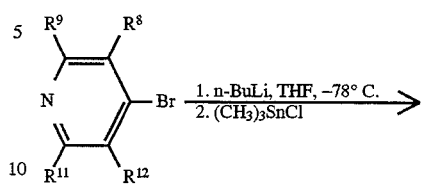

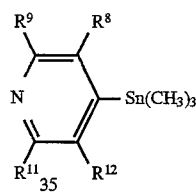

Synthetic Scheme VIII shows the preparation of the prerequisite substitutedphenyltrimethyltin analogs 29 and substitutedpyridinyltrimethyltin analogs 31, 33, and 35 from the available bromides 28, 30, 32, and 34, respectively. Halogen-metal interchange in THF at −78° C. generates the organolithium reagents which are reacted with trimethyltin chloride. Purification provides the substitutedphenyltrimethyltin analogs 29 and the substitutedpyridinyltrimethyltin analogs 31, 33, and 35, respectively.

Scheme IX

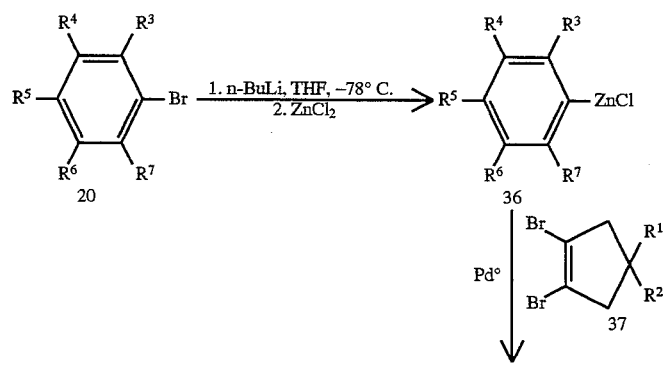

-continued
Scheme IX

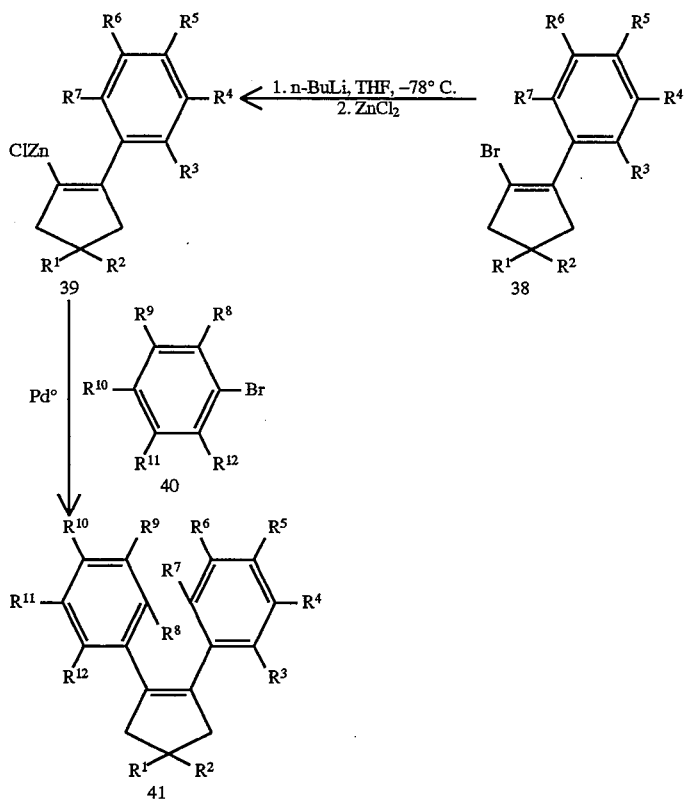

Synthetic Scheme IX shows the four step procedure for the preparation of 1,2-diaryl-4,4-disubstitutedcyclopentene anti-inflammatory agents 41 from the available bromides 20 using a sequential coupling procedure which is similar to the coupling procedure developed by Negishi, et al., [*J. Org. Chem.*, 42, 1821 (1977)]. In step one, halogen-metal interchange of 20 with n-butyllithium in THF at −78° C. gives the corresponding organolithium reagents which subsequently react with zinc chloride to give the organozinc reagents 36. In step two, the organozinc reagents 36 are coupled with the 1,2-dibromo-4,4-disubstitutedcyclopentenes 37 (prepared in Synthetic Schemes I–IV) in the presence of a Pd° catalyst, e.g., tetrakis(triphenylphosphine)palladium (0), to give the monocoupled bromides 38 (after separation from the bis-coupled by-product). In step three, the bromides 38 are treated as above to give the organozinc reagents 39. In step four, the monocoupled organozinc reagents 39 are coupled with the arylbromides 40 (which can be identical with 20 when $R^3=R^8$, $R^4=R^9$, $R^5=R^{10}$, $R^6=R^{11}$, and $R^7=R^{12}$) to give the 1,2-diaryl-4,4-disubstitutedcyclopentene anti-inflammatory agents 41 of this invention.

Scheme X

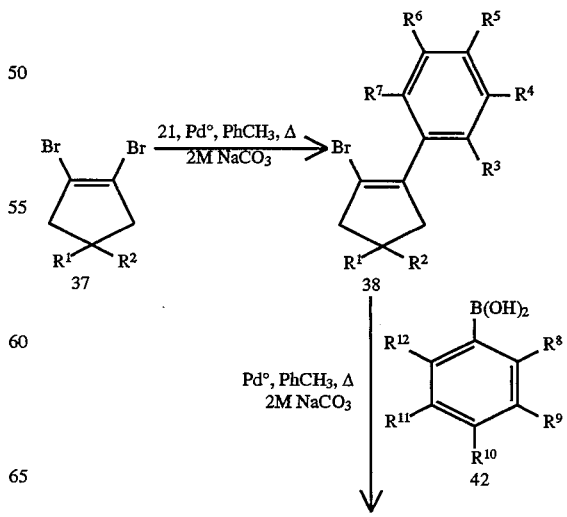

37
-continued
Scheme X

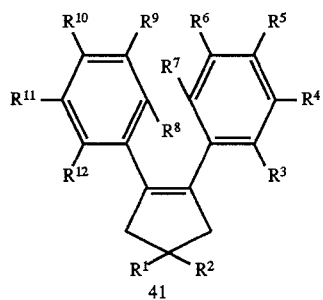

41

38
-continued
Scheme XI

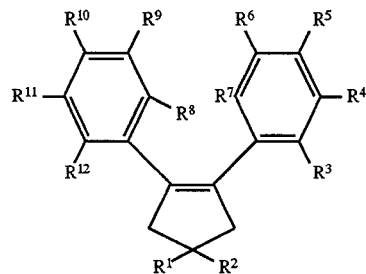

41

Synthetic Scheme X shows the two step procedure for the preparation of 1,2-diaryl-4,4-disubstitutedcyclopentene anti-inflammatory agents 41 from 1,2-dibromo-4,4-disubstitutedcyclopentenes 37 (prepared in Synthetic Scheme I–VI) and substituted phenylboronic acids 21 and 42 (prepared in Synthetic Scheme VII) using a sequential coupling procedure which is similar to the coupling procedure developed by Suzuki, et al., [*Syn. Commun.*, 11, 513 (1981)]. In step one, the dibromides 37 are treated with the boronic acids 21 in toluene at reflux in the presence of Pd° catalyst, e.g., tetrakis(triphenylphosphine)palladium (0), and 2M sodium carbonate to give the monocoupled bromides 38 (after separation from the biscoupled by-product). In step two, the monocoupled bromides 38 are coupled as above with the boronic acids 42 (which can be identical with 21 when $R^3=R^8$, $R^4=R^9$, $R^5=R^{10}$, $R^6=R^{11}$, and $R^7=R^{12}$) give the 1,2-diaryl-4,4-disubstitutedcyclopentene anti-inflammatory agents 41 of this invention.

Synthetic Scheme XI shows the two step procedure for the preparation of 1,2-diaryl-4,4-disubstitutedcyclopentene anti-inflammatory agents 41 from 1,2-dibromo-4,4-disubstitutedcyclopentenes 37 (prepared in Synthetic Scheme I–IV) and substitutedphenyltrimethyltin analogs 29 and 43 (prepared in Synthetic Scheme VII) using a sequential coupling procedure which is similar to the coupling procedure developed by Stille, et al., [*J. Am. Chem. Soc.*, 101, 4992 (1979))]. In step one, the dibromides 37 are treated with the trimethyltin analogs 29 in toluene at reflux in the presence of a Pd° catalyst, e.g., tetrakis(triphenylphosphine)palladium (0), to give the monocoupled bromides 38 (after separation from the biscoupled by-product). In step two, the monocoupled bromides 38 are coupled as above with the trimethyltin analogs 43 (which can be identical with 29 when $R^3=R^8$, $R^4=R^9$, $R^5=R^{10}$, $R^6=R^{11}$, and $R^7=R^{12}$) to give the 1,2-diaryl-4,4-disubstitutedcyclopentene anti-inflammatory agents 41 of this invention.

Scheme XI

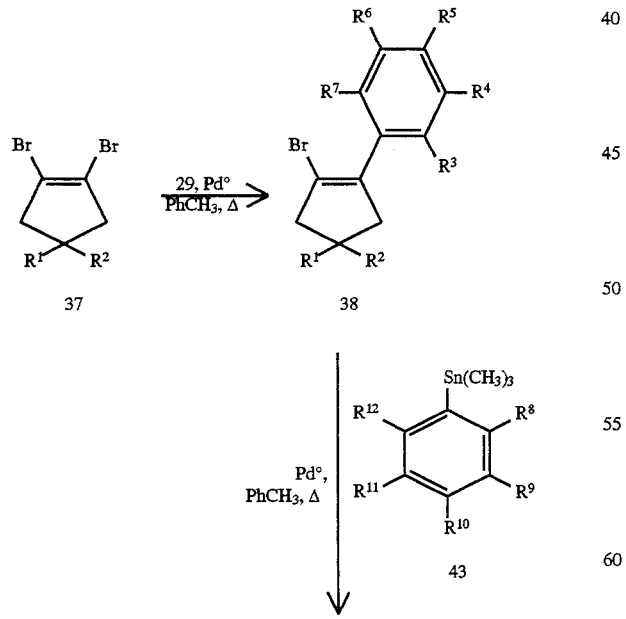

Scheme XII

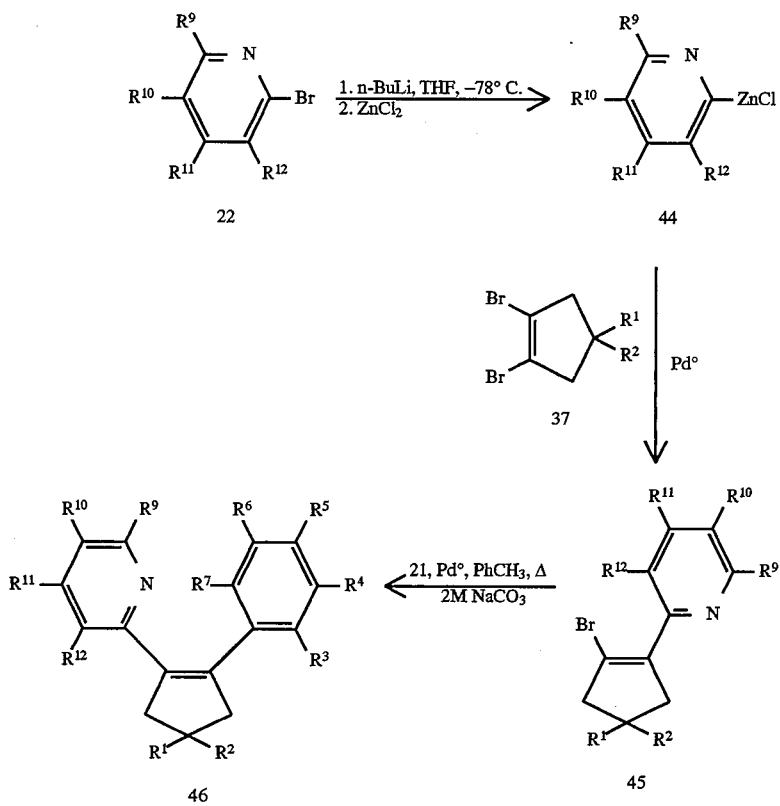

Synthetic Scheme XII shows the three step preparation of 1-aryl-2-(2-pyridinyl)-4,4-disubstitutedcyclopentene anti-inflammatory agents 46 from 1,2-dibromo-4,4-disubstitutedcyclopentenes 37 (prepared in Synthetic Scheme I–IV) and the available 2-bromopyridines 22. In step one, halogen-metal interchange of 22 with n-butyllithium in THF at −78° C. gives the 2-lithiopyridines which subsequently react with zinc chloride to give the corresponding 2-pyridinylzinc reagents 44. In step two, a Negishi coupling (see Synthetic Scheme IX) of the 2-pyridinylzinc reagents 44 with 37 gives the monocoupled 2-pyridinyl bromides 45 (after separation from the bis-coupled by-product). In step three, a Suzuki coupling (see Synthetic Scheme X) of the monocoupled 2-pyridinyl bromides 45 with substituted phenylboronic acids 21 (prepared in Synthetic Scheme VII) gives the 1-aryl-2-(2-pyridinyl)-4,4-disubstitutedcyclopentene anti-inflammatory agents 46 of this invention.

Scheme XIII

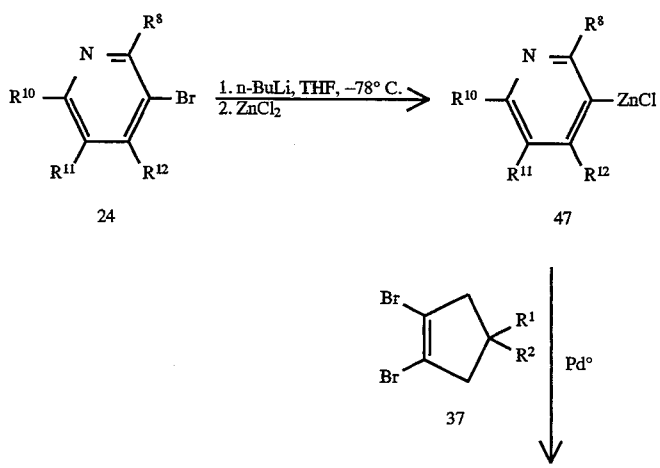

-continued
Scheme XIII

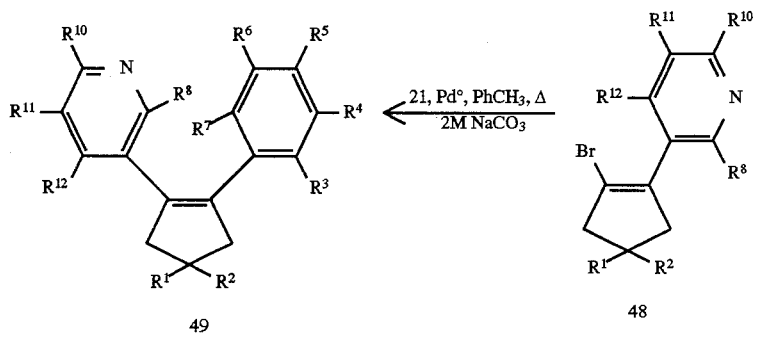

Synthetic Scheme XIII shows the three step preparation of 1-aryl-2-(3-pyridinyl)4,4-disubstitutedcyclopentene anti-inflammatory agents 49 from 1,2-dibromo-4,4-disubstitutedcyclopentenes 37 (prepared in Synthetic Scheme I–IV) and the available 3-bromopyridines 24. In step one, halogen-metal interchange of 24 with n-butyllithium in THF at −78° C. gives the 3-lithiopyridines which subsequently react with zinc chloride to give the corresponding 3-pyridinylzinc reagents 47. In step two, a Negishi coupling (see Synthetic Scheme IX) of the 3-pyridinylzinc reagents 47 with 37 gives the monocoupled 3-pyridinyl bromides 48 (after separation from the bis-coupled by-product). In step three, a Suzuki coupling (see Synthetic Scheme X) of the monocoupled 3-pyridinyl bromides 48 with substituted phenylboronic acid 21 (prepared in Synthetic Scheme VII) gives the 1-aryl-2-(3-pyridinyl)-4,4-disubstitutedcyclopentene anti-inflammatory agents 49 of this invention.

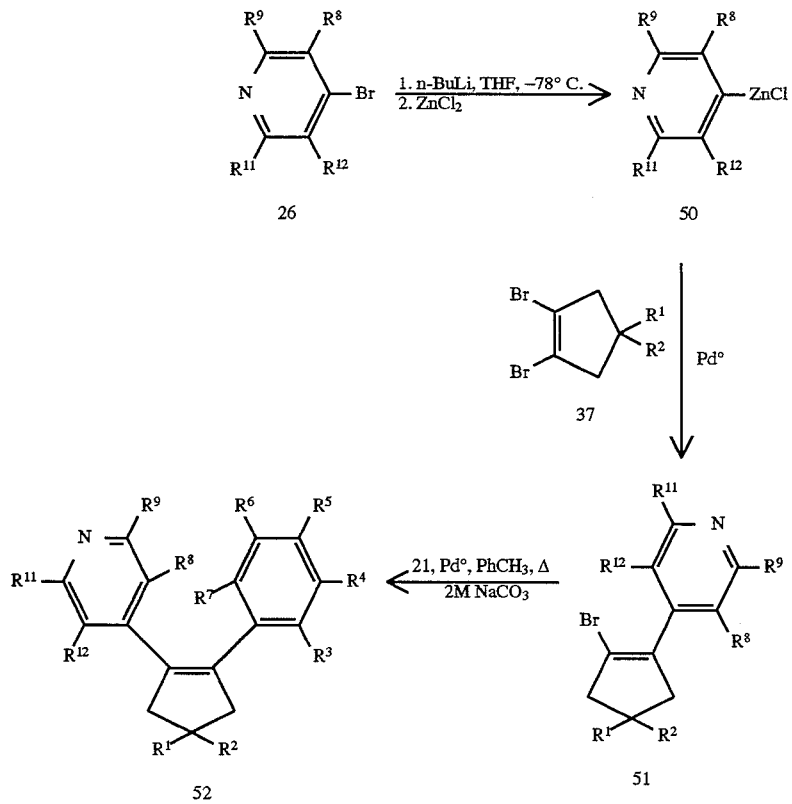

Synthetic Scheme XIV shows the three step preparation of 1-aryl-2-(4-pyridinyl)-4,4-disubstitutedcyclopentene anti-inflammatory agents 52 from 1,2-dibromo-4,4-disubstitutedcyclopentenes 37 (prepared in Synthetic Scheme I–IV) and the available 4-bromopyridines 26. In step one, halogen-metal interchange of 26 with n-butyllithium in THF at −78° C. gives the 4-lithiopyridines which subsequently react with zinc chloride to give the corresponding 4-pyridinylzinc reagents 50. In step two, a Negishi coupling (see Synthetic Scheme IX) of the 4-pyridinylzinc reagents 50 with 37 gives the monocoupled 4-pyridinyl bromides 51 (after separation from the bis-coupled by-product). In step three, a Suzuki coupling (see Synthetic X) of the monocoupled 4-pyridinyl bromides 51 with substituted phenylboronic acids 21 (prepared in Synthetic Scheme VII) gives the 1-aryl-2-(4-pyridinyl)-4,4-disubstitutedcyclopentene anti-inflammatory agents 52 of this invention.

sodium iodide to give the corresponding phenyl silyl enol ethers. 56.

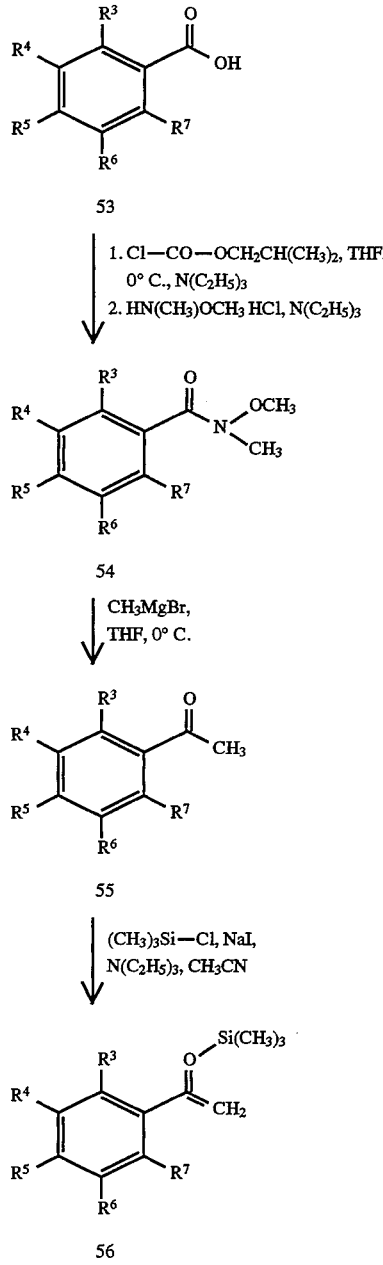

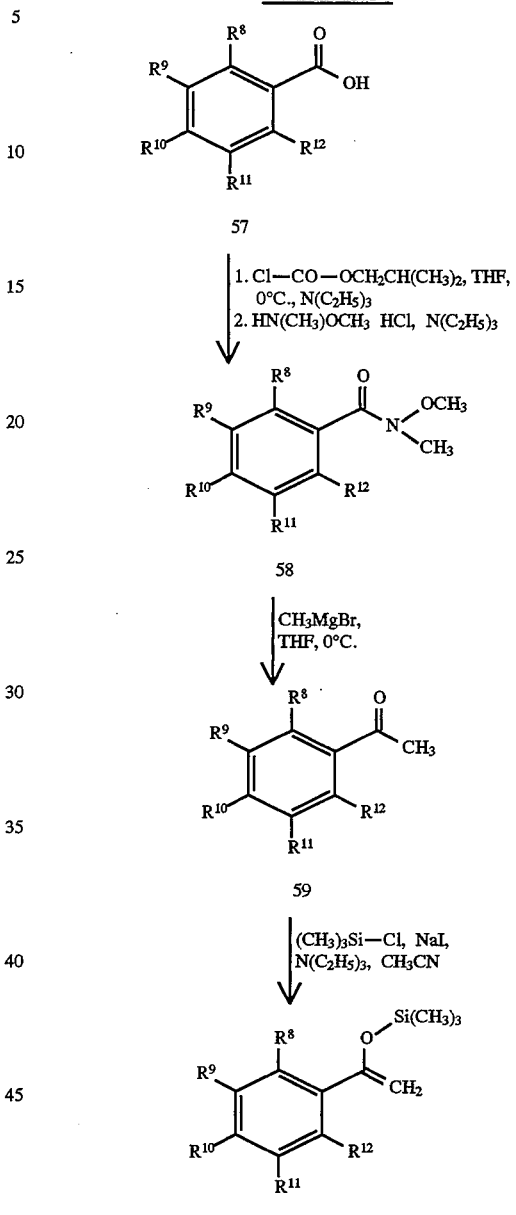

Synthetic Scheme XV shows the three step procedure used to prepare the phenyl silyl enol ethers 56 from commercially available benzoic acids 53. In step one, a THF solution at 0° C. of the benzoic acids 53 and two equivalents of triethylamine are sequentially treated with isobutyl chloroformate and N-hydroxymethyl-N-methylamine hydrochloride to give the Weinreb amides 54 [see: S. Nahm and S. M. Weinreb, *Tetrahedron Lett.*, 21, 3815 (1981)]. In step two, the amides 54 are reacted with methylmagnesium bromide to give the corresponding acetophenones 55. In step three, the acetophenones 55 are treated with chlorotrimethylsilane in acetonitrile in the presence of triethylamine and Synthetic Scheme XVI shows the three step procedure used to prepare the phenyl silyl enol ethers 60 from commercially available benzoic acids 57. In step one, a THF solution at 0° C. of the benzoic acids 57 and two equivalents of triethylamine are sequentially treated with isobutyl chloroformate and N-hydroxymethyl-N-methylamine hydrochloride to give the Weinreb amides 58. In step two, the amides 58 are reacted with methylmagnesiumbromide to give the corresponding acetophenones 59. In step three, the acetophenones 59 are treated with chlorotrimethylsilane in acetonitrile in the presence of triethylamine and sodium iodide to give the corresponding phenyl silyl enol ethers 60.

Scheme XVII

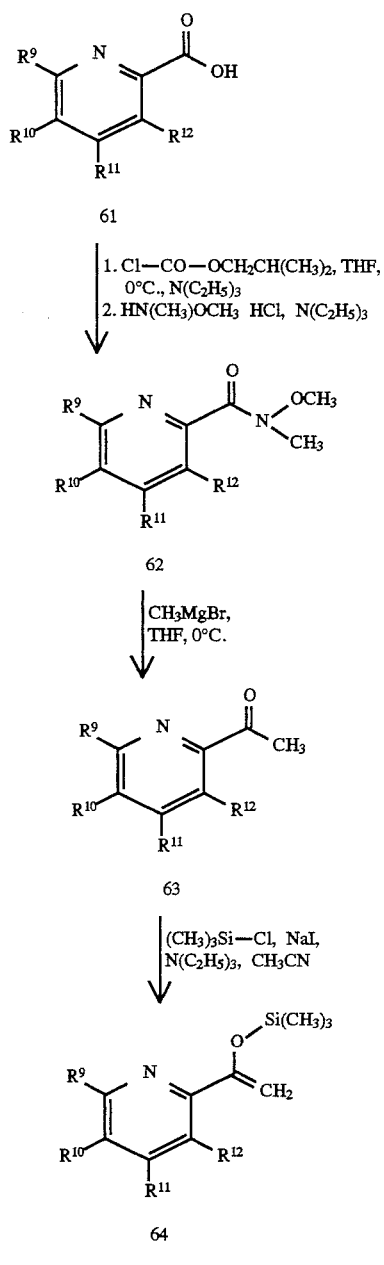

Scheme XVIII

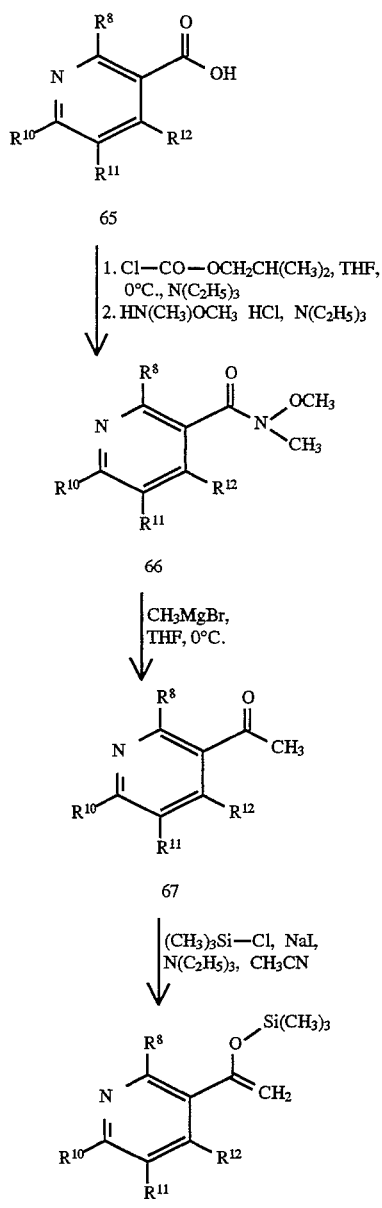

Synthetic Scheme XVII shows the three step procedure used to prepare the 2-pyridinyl silyl enol ethers 64 from commercially available picolinic acids 61. In step one, a THF solution at 0° C. of the picolinic acids 61 and two equivalents of triethylamine are sequentially treated with isobutyl chloroformate and N-hydroxymethyl-N-methylamine hydrochloride to give the Weinreb amides 62. In step two, the amides 62 are reacted with methylmagnesium bromide to give the corresponding 2-acetylpyridines 63. In step three, the 2-acetylpyridines 63 are treated with chlorotrimethylsilane in acetonitrile in the presence of triethylamine and sodium iodide to give the corresponding 2-pyridinyl silyl enol ethers 64.

Synthetic Scheme XVIII shows the three step procedure used to prepare the 3-pyridinyl silyl enol ethers 68 from commercially available nicotinic acids 65. In step one, a THF solution at 0° C. of the nicotinic acids 65 and two equivalents of triethylamine are sequentially treated with isobutyl chloroformate and N-hydroxymethyl-N-methylamine hydrochloride to give the Weinreb amides 66. In step two, the amides 66 are reacted with methylmagnesium bromide to give the corresponding 3-acetylpyridines 67. In step three, the 3-acetylpyridines 67 are treated with chlorotrimethylsilane in acetonitrile in the presence of triethylamine and sodium iodide to give the corresponding 3-pyridinyl silyl enol ethers 68.

Scheme XIX

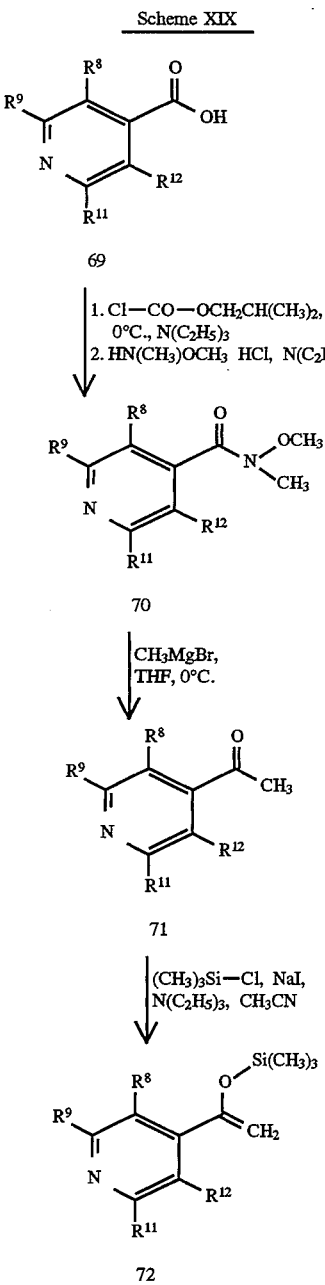

Scheme XX

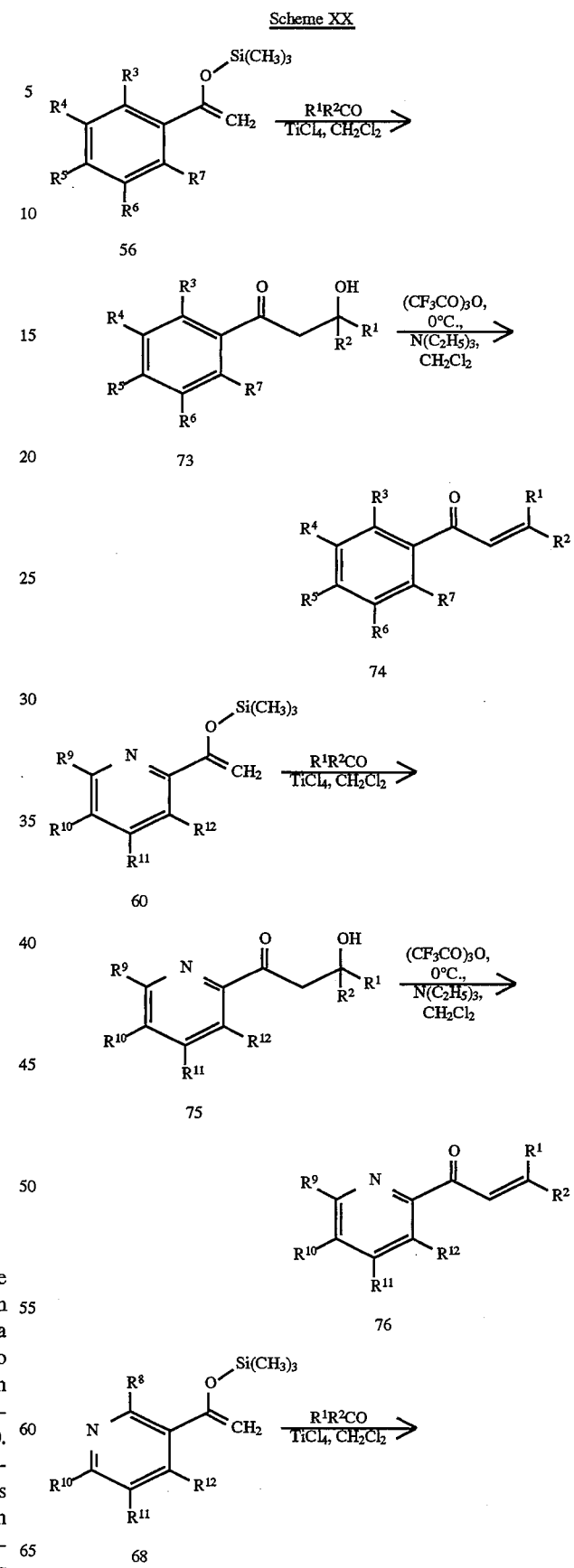

Synthetic Scheme XIX shows the three step procedure used to prepare the 4-pyridinyl silyl enol ethers 72 from commercially available isonicotinic acids 69. In step one, a THF solution at 0° C. of the isonicotinic acids 69 and two equivalents of triethylamine are sequentially treated with isobutyl chloroformate and N-hydroxymethyl-N-methylamine hydrochloride to give the Weinreb amides 70. In step two, the amides 70 are reacted with methylmagnesium bromide to give the corresponding 4-acetylpyridines 71. In step three, the 4-acetylpyridines 71 are treated with chlorotrimethylsilane in acetonitrile in the presence of triethylamine and sodium iodide to give the corresponding 4-pyridinyl silyl enol ethers 72.

Scheme XX -continued

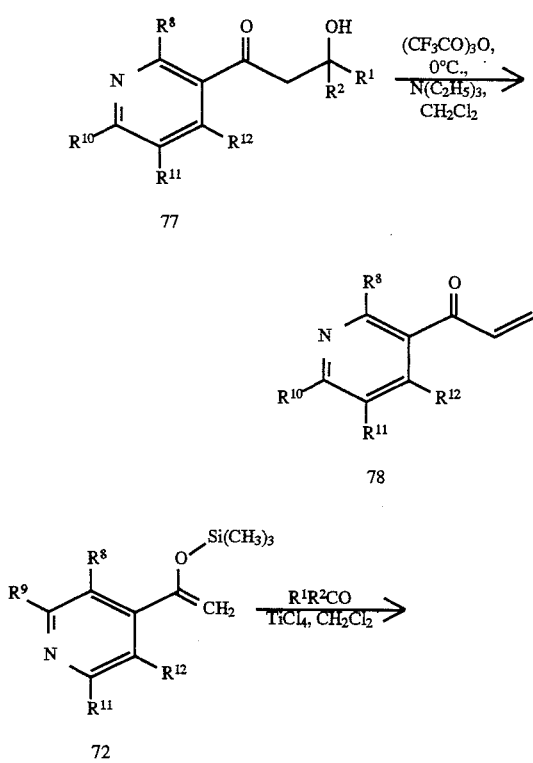

Scheme XXI

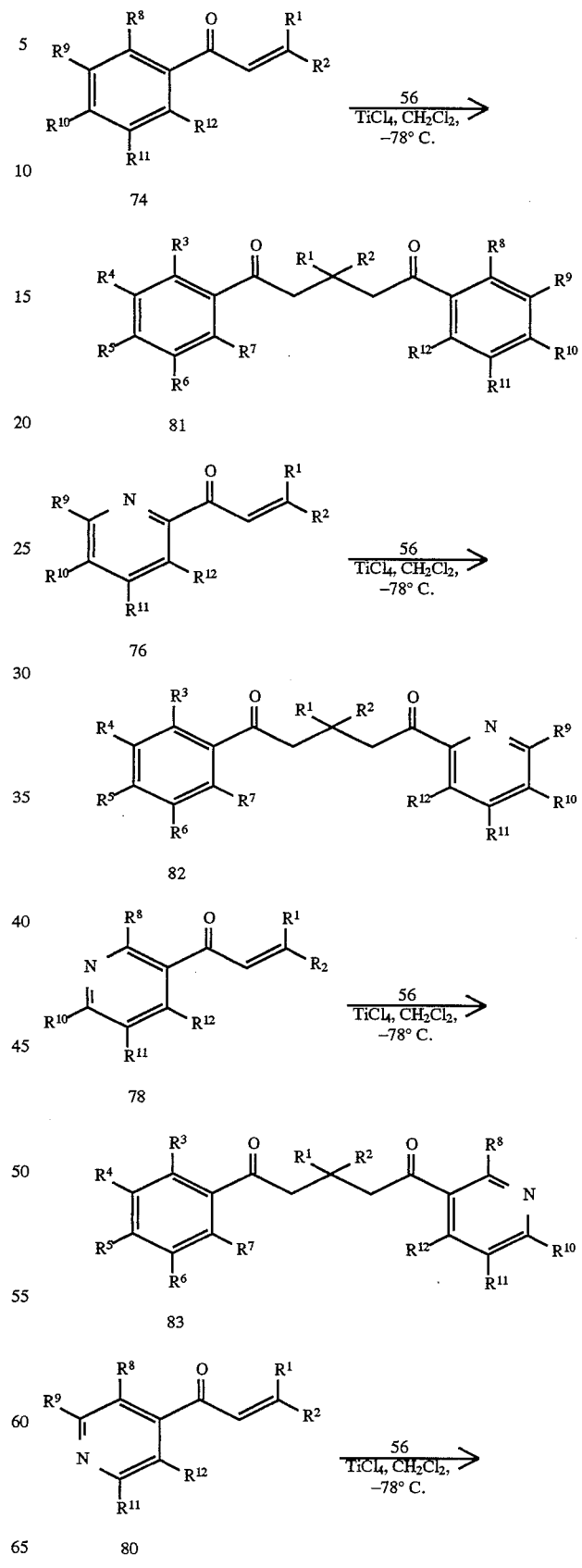

Synthetic Scheme XX shows the two step procedures used to prepare the enones 74, 76, 78, and 80 from the phenyl silyl enol ethers 56, 60, 68, and 72, respectively (prepared in Synthetic Schemes XVI–XIX). In step one, the silyl enol ethers 56, 60, 68, and 72 are reacted with the appropriate ketones in methylene chloride in the presence of titanium (IV) chloride to give the corresponding 3-hydroxyketones 73, 75, 77, and 79, respectively. In step two, the 3-hydroxyketones 73, 75, 77, and 79 are dehydrated with trifluoroacetic anhydride and triethylamine in methylene chloride at 0° C. to give the corresponding enones 74, 76, 78, and 80, respectively.

-continued
Scheme XXI

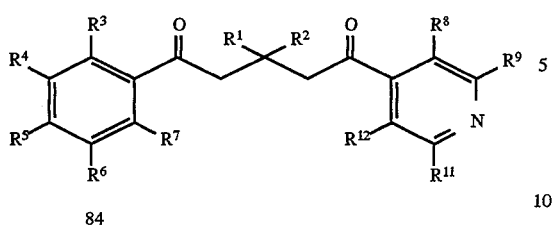

84

(prepared in Synthetic Scheme XV) in the presence of titanium (IV) chloride to give the corresponding 1,5-diketones 81, 82, 83, and 84, respectively.

Synthetic Scheme XXI shows the procedures used to prepare the 1,5-diketones 81, 82, 83, and 84 from the enones 74, 76, 78, and 80, respectively (prepared in Synthetic Scheme XX). Methylene chloride solutions of the enones 74, 76, 78, and 80 are reacted with the silyl enol ethers 56

Scheme XXII

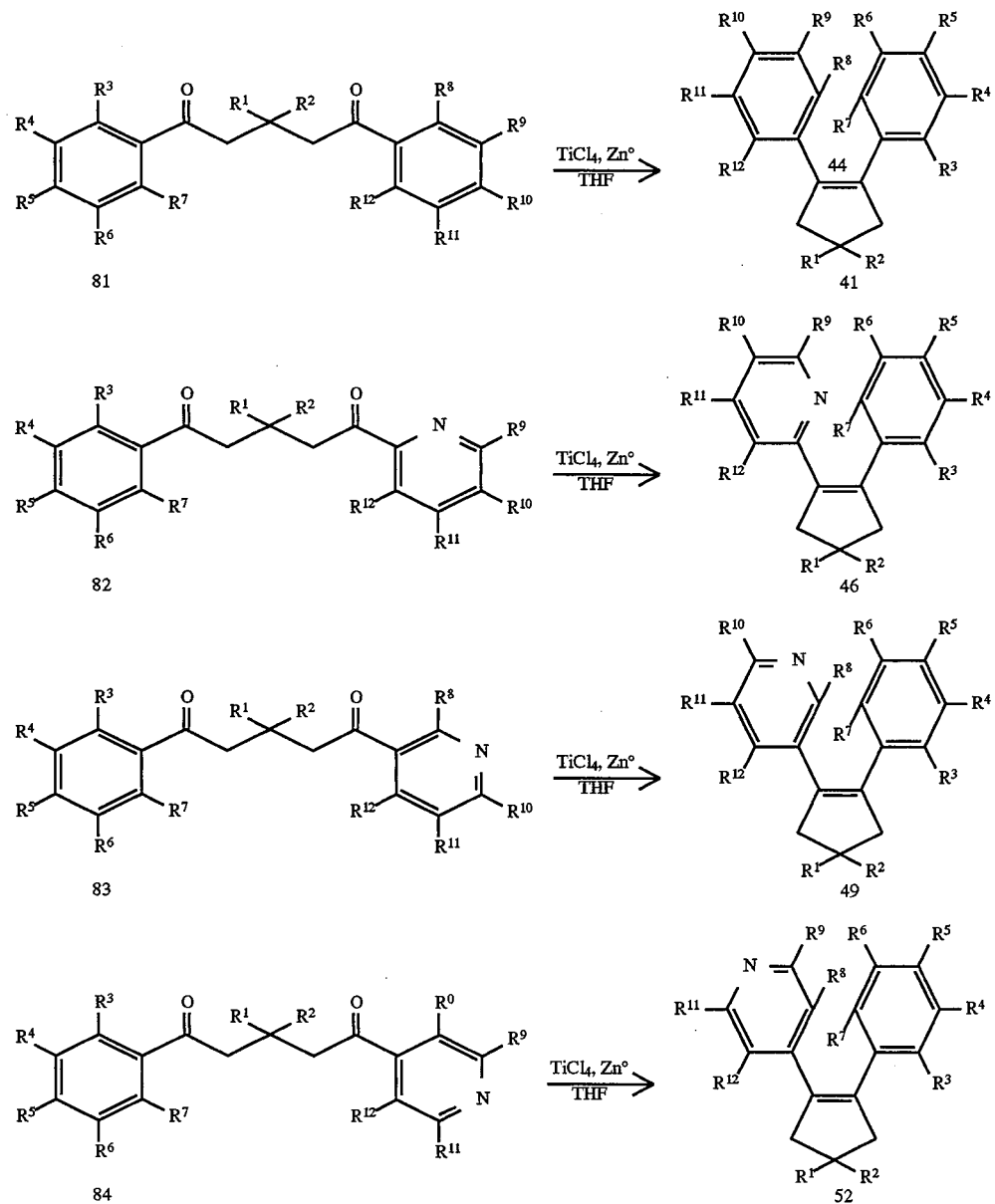

Synthetic Scheme XXII shows alternative procedures which may be used to prepare 1,2-diaryl-4,4-disubstitutedcyclopentenes 41, 1-aryl-2-(2-pyridinyl)-4,4-disubstitutedcyclopentenes 46, 1-aryl-2-(3-pyridinyl)-4,4-disubstitutedcyclopentenes 49, and 1-aryl-2-(4-pyridinyl)-4,4-disubstitutedcyclopentenes 52 from the 1,5-diketones 81, 82, 83 and 84, respectively (prepared in Synthetic Scheme XXI). Tetrahydrofuran solutions of 1,5-diketones 81, 82, 83 and 84 are treated with metallic zinc and titanium IV chloride to give the reduced cyclized 1,2-diaryl-4,4-disubstitutedcyclopentene antiinflammatory agents 41, 1-aryl-2-(2-pyridinyl)-4,4-disubstitutedcyclopentene antiinflammatory agents 46, 1-aryl-2-(3-pyridinyl)-4,4-disubstituted cyclopentene antiinflammatory agents 49, and 1-aryl-2-(4-pyridinyl)-4,4-disubstitutedcyclopentene antiinflammatory agents 52, respectively, of this invention.

Scheme XXIII

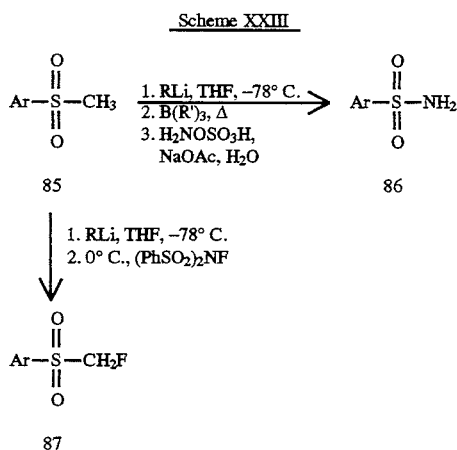

Synthetic Scheme XXIII shows the three step procedure used to prepare sulfonamide antiinflammatory agents 86 and the two step procedure used to prepare fluoromethylsulfone antiinflammatory agents 87 from their corresponding methylsulfones 85. In step one, THF solutions of the methylsulfones 85 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior at stirring at reflux. In step three, an aqueous solution of sodium acetate and hydroxyamine-O-sulfonic acid is added to provide the corresponding sulfonamide antiinflammatory agents 86 of this invention. Alternatively, the anion solutions generated in step one may be warmed to 0° C. and treated with N-fluorodibenzenesulfonamide to provide the corresponding fluoromethylsulfone antiinflammatory agents 87 of this invention.

The following examples contain detailed descriptions of the methods of preparation of compounds of Formula I–VI. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated.

EXAMPLE 1

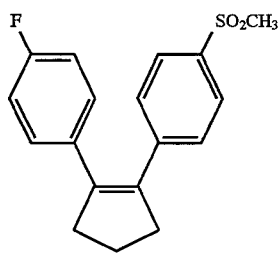

1-[2-(4-Fluorophenyl)cyclopenten-1-yl]-4-(methylsulfonyl)benzene

Step 1: Preparation of 4-methylthiophenylboronic acid.

Under nitrogen, a stirred solution of 30 g (150 mmol of 4-bromothioanisole (Aldrich) in 1500 mL of anhydrous THF at −78° C. was treated with 180 mmol of n-butyllithium in hexane. After 30 minutes, 51 mL (450 mmol) of trimethylborate was added neat and the reaction was allowed to warm to ambient temperature overnight. A solution of 300 mL of 10% NaOH was added and the mixture stirred vigorously for 1 hour. The solvent was removed in vacuo, the pH adjusted to 4–5, and the product collected by filtration. Repeated washings with hexane and water provided 21 g (83%) of 4-methylthiophenylboronic acid (21 in Synthetic Scheme VII when $R^5=SCH_3$ and $R^3$, $R^4$, $R^6$, and $R^7=H$) as a colorless solid: NMR (DHSO-$d_6$) δ 2.47 (s, 3H), 7.20 (d, J=8 Hz, 2H), 7.71 (d, J=8 Hz, 2H), 7.96 (br s, 2H).

Step 2: Preparation of 1-(2-bromocyclopenten-1-yl)-4-(methylthio)benzene.

Under nitrogen, 36.4 g (161 mmol) of 1,2-dibromocyclopentene (Aldrich) was reacted with 18.0 g (107 mmol) of 4-methylthiophenylboronic acid (Step 1) in 550 mL of toluene, 365 mL of ethanol, and 235 mL of 2M $Na_2CO_3$ in the presence of 6.0 g (5 mol %) of $Pd(PPh_3)_4$. The reaction was vigorously stirred at reflux overnight and concentrated in vacuo. The residue was dissolved in ethyl acetate and washed with water, dried ($MgSO_4$), and reconcentrated. Purification by silica gel chromatography (Waters Prep-500) with hexane gave 9.39 g (22%) of 1-(2-bromocyclopenten-1-yl)-4-(methylthio)benzene (38 in Synthetic Scheme X when $R^5=SCH_3$ and $R^1$, $R^2$, $R^3$, $R^4$, $R^6$, and $R^7=H$) as a solid: mp 52°–54° C.; NMR (CDCl$_3$) δ 1.98–2.09 (m, 2H), 2.50 (s, 3H), 2.70–2.78 (m, 2H), 2.80–2.89 (m, 2H), 7.24 (d, J=8 Hz, 2H), 7.55 (d, J=8 Hz, 2H).

Step 3: Preparation of 1-[2-(4-fluorophenyl)cyclopenten-1-yl]-4-(methylthio)benzene.

Under nitrogen, 1.5 g (5.6 mmol) of 1-(2-bromocyclopenten-1-yl)-4-(methylthio)benzene (Step 2) was reacted with 1.5 g (11 mmol) of 4-fluorophenylboronic acid (Lancaster) in 30 mL of toluene, 20 mL of ethanol, and 25 mL of 2M $Na_2CO_3$ in the presence of 250 mg of $Pd(PPh_3)_4$. The reaction was vigorously stirred at reflux overnight and concentrated in vacuo. The residue was dissolved in ethyl acetate and washed with water, dried ($MgSO_4$), and reconcentrated. Purification by silica gel chromatography with hexane gave 1-[2-(4-fluorophenyl)cyclopenten-1-yl]-4-(methylthio)benzene (41 in Synthetic Scheme X when $R^5=SCH_3$, $R^{10}=F$, and $R^1$, $R^2$, $R^3$, $R^4$, $R^6$, $R^7$, $R^8$, $R^9$, $R^{11}$, and $R^{12}=H$) as a colorless solid: mp 46°–47° C.; NMR (CDCl$_3$) δ 2.04 (m, J=7 Hz, 2H), 2.45 (s, 3H), 2.86, (t, J=7 Hz, 4H), 6.86–6.94 (m, 2H), 7.08 (br s, 4H), 7.10–7.18 (m, 2H).

Step 4: Preparation of 1-[2-(4-fluorophenyl)cyclopenten-1-yl]-4-(methylsulfonyl)benzene.

A solution of 1.5 g (5 mmol) of 1-[2-(4-fluorophenyl) cyclopenten-1-yl]-4-(methylthio)benzene (Step 3) in 46 mL of methanol/THF (1:1) was slowly treated with 5.2 g (8.4 mmol) of Oxone® [2 KHSO$_5$.KHSO$_4$.K$_2$SO$_4$] in 23 mL of water. After stirring for 4 hours, the solvent was removed in vacuo. The residue was dissolved in ethyl acetate and washed with water and brine, dried (MgSO$_4$), and reconcentrated. Recrystallization from ethyl acetate/hexane provided 960 mg (54%) of 1-[2-(4-fluorophenyl)cyclopenten-1-yl]-4-(methylsulfonyl)benzene (41 in Synthetic Scheme X when $R^5$=SO$_2$CH$_3$, $R^{10}$=F, and $R^1$, $R^2$, $R^3$, $R^4$, $R^6$, $R^7$, $R^8$, $R^9$, $R^{11}$, and $R^{12}$=H) as a colorless solid: mp 138°–139° C.; NMR (CDCl$_3$) δ 2.09 (m, J=7 Hz, 2H), 2.91 (t, J=7 Hz, 4H), 3.04 (s, 3H), 6.88–6.96 (m, 2H), 7.06–7.14 (m, 2H), 7.32 (d, J=8 Hz, 2H), 7.76 (d, J=8 Hz, 2H). MS (EI) m/e (rel intensity) 316 (100), 237 (41), 161 (13); HRMS. Calc'd for C$_{18}$H$_{17}$FO$_2$S: 316.0933. Found: 316.0943. Anal. Calc'd for C$_{18}$H$_{17}$FO$_2$S: C, 68.33; H, 5.42; F, 6.00; S, 10.13. Found: C, 68.08; H, 5.45; F, 6.42; S, 9.98.

EXAMPLE 2

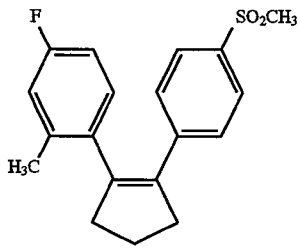

1-[2-(4-Fluoro-2-methylphenyl)cyclopenten-1-yl]-4-(methylsulfonyl)benzene

Step 1: Preparation of 4-fluoro-2-methylphenylboronic acid.

Following the synthetic procedure outlined in Step 1 of Example 1, 2-bromo-5-fluorotoluene (Aldrich) was converted to 4-fluoro-2-methylphenylboronic acid: NMR (DMSO-d$_6$) δ 2.40 (s, 3H), 6.85–6.99 (m, 2H), 7.46 (d, J=7 Hz, 1H).

Step 2: Preparation of 1-[2-(4-fluoro-2-methylphenyl)cyclopenten-1-yl]-4-(methylthio)benzene.

Following the synthetic procedure outlined in Step 3 of Example 1, 500 mg (1.9 mmol) of 1-(2-bromocyclopenten-1-yl)-4-(methylthio)benzene (Example 1, Step 2) was reacted with 590 mg (3.8 mmol) of 4-fluoro-2-methylphenylboronic acid (Step 1). Purification by silica gel chromatography (MPLC) with hexane gave 500 mg (95%) of 1-[2-(4-fluoro-2-methylphenyl)cyclopenten-1-yl]-4-(methylthio)benzene as a colorless solid: mp 67°–68° C.; NMR (CDCl$_3$) δ 2.00–2.11 (m, 2H), 2.05 (s, 3H), 2.41 (s, 3H), 2.69–2.77 (m, 2H), 2.86–2.95 (m, 2H), 6.80–7.07 (m, 7H).

Step 3: Preparation of 1-[2-(4-fluoro-2-methylphenyl) cyclopenten-1-yl]-4-(methylsulfonyl)benzene.

Following the synthetic procedure outlined in Step 4 of Example 1, 470 mg (1.6 mmol) of 1-[2-(4-fluoro-2-methylphenyl)cyclopenten-1-yl]-4-(methylthio)benzene (Step 2) was oxidized. Purification by silica gel chromatography with hexane/ethyl acetate (1:4) and subsequent recrystallization from ethyl acetate/hexane gave 1-[2-(4-fluoro-2-methylphenyl)cyclopenten-1-yl]-4-(methylsulfonyl) benzene as a colorless solid: mp 112.5°–113.5° C.; NMR (CDCl$_3$) δ 2.03–2.16 (m, 2H), 2.05 (s, 3H), 2.74–2.82 (m, 2H), 2.91–3.01 (m, 2H), 2.98 (s, 3H), 6.83–6.93 (m, 2H); 6.97–7.04 (m, 1H), 7.19 (d, J=8 Hz, 2H), 7.68 (d, J=8 Hz, 2H); MS (FAB) m/e (rel intensity) 337 (100), 331 (46); HRMS. Calc'd for C$_{19}$H$_{19}$FO$_2$S: 330.1090. Found: 330.1096. Anal. Calc'd for C$_{19}$H$_{19}$FO$_2$S: C, 69.07; H, 5.80; F, 5.75; S, 9.70. Found: C, 69.37; H, 5.81; F, 5.40; S, 9.78.

EXAMPLE 3

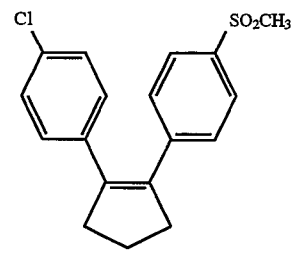

1-[2-(4-Chlorophenyl)cyclopenten-1-yl]-4-(methylsulfonyl)benzene

Step 1: Preparation of 1-[2-(4-chlorophenyl)cyclopenten-1-yl]-4-(methylthio)benzene.

Following the synthetic procedure outlined in Step 3 of Example 1, 250 mg (0.93 mmol) of 1-(2-bromocyclopenten-1-yl)-4-(methylthio)benzene (Example 1, Step 2) was reacted with 300 mg (1.9 mmol) of 4-chlorophenylboronic acid (Lancaster). Purification by silica gel chromatography (MPLC) with hexane gave 290 mg of 1-[2-(4-chlorophenyl) cyclopenten-1-yl]-4-(methylthio)benzene as a colorless solid: mp 72°–74° C.; NMR (CDCl$_3$) δ 2.04 (m, J=7 Hz, 2H), 2.46 (s, 3H), 2.86 (t, J=7 Hz, 4H), 7.07–7.21 (m, 8H).

Step 2: Preparation of 1-[2-(4-chlorophenyl)cyclopenten-1-yl]-4-(methylsulfonyl)benzene.

Following the synthetic procedure outlined in Step 4 of Example 1, 280 mg (0.93 mmol) of 1-[2-(4-chlorophenyl) cyclopenten-1-yl]-4-(methylthio)benzene (Step 1) was oxidized. Purification by silica gel chromatography (MPLC) with hexane and subsequent recrystallization from ethyl acetate/hexane gave 192 mg (62%) of 1-[2-(4-chlorophenyl) cyclopenten-1-yl]-4-(methylsulfonyl)benzene as a colorless solid: mp 127.5°–128.5° C.; NMR (CDCl$_3$) δ 2.09 (m, J=7 Hz, 2H), 2.91 (t, J=7 Hz, 4H), 3.04 (s, 3H), 7.06, (d, J=8 Hz, 2H), 7.21 (d, J=8 Hz, 2H), 7.32 (d, J=8 Hz, 2H), 7.77 (d, J=8 Hz, 2H); MS (EI) m/e (rel intensity) 332 (100), 297 (6), 218 (30); HRMS. Calc'd for C$_{18}$H$_{17}$ClO$_2$S: 332.0638. Found: 332.0628. Anal. Calc'd for C$_{18}$H$_{17}$ClO$_2$S: C, 64.95; H, 5.15; Cl, 10.65; S, 9.63. Found: C, 64.97; H, 5.15; Cl, 10.50; S, 9.58.

EXAMPLE 4

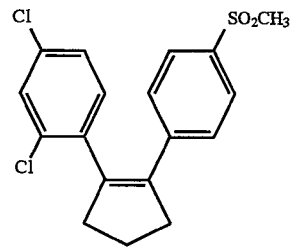

1-[2-(2,4-Dichlorophenyl)cyclopenten-1-yl]-4-(methylsulfonyl)benzene

Step 1: Preparation of 1-[2-(2,4-dichlorophenyl) cyclopenten-1-yl]-4-(methylthio)benzene.

Following the synthetic procedure outlined in Step 3 of Example 1, 280 mg (0.93 mmol) of 1-(2-bromocyclopenten-1-yl)-4-(methythio)benzene (Example 1, Step 2) was reacted with 350 mg (1.9 mmol) of 2,4-dichlorophenylboronic acid (Lancaster). Purification by silica gel chromatography (MPLC) with hexane gave 280 mg of 1-[2-(2,4-dichlorophenyl)cyclopenten-1-yl]-4-(methylthio)benzene as an oil: NMR (CDCl$_3$) δ 2.10 (m, J=7 Hz, 2H), 2.41 (s, 3H), 2.81 (t, J=8 Hz, 4H), 2.92 (m, J=8 Hz, 2H), 6.95–7.21 (m, 6H), 7.40 (s, 1H).

Step 2: Preparation of 1-[2-(2,4-dichlorophenyl)cyclopenten-1-yl]-4-(methylsulfonyl)benzene.

Following the synthetic procedure outlined in Step 4 of Example 1, 280 mg (0.85 mmol) of 1-[2-(4-chlorophenyl)cyclopenten-1-yl]-4-(methylthio)benzene (Step 1) was oxidized. Purification by silica gel chromatography (MPLC) with hexane and subsequent lyophilization from acetonitrile/water (1:1) gave 158 mg (51%) of 1-[2-(2,4-dichlorophenyl)cyclopenten-1-yl]-4-(methylsulfonyl)benzene as a solid: NMR (CDCl$_3$) δ 2.13 (m, J=8 Hz, 2H), 2.84 (t, J=8 Hz, 2H), 2.96 (t, J=8 Hz, 2H), 3.00 (s, 3H), 6.97, (d, J=8 Hz, 1H), 7.14–7.23 (m, 4H), 7.42 (d, J=2 Hz, 1H), 7.71 (d, J=9 Hz, 2H); MS (EI) m/e (rel intensity) 368 (61), 366 (91), 252 (100) 215 (64), 128 (47); HRMS. Calc'd for C$_{18}$H$_{16}$Cl$_2$O$_2$S: 366.0242. Found: 332.0249. Anal. Calc'd for C$_{18}$H$_{16}$Cl$_2$O$_2$S: C, 58.86; H, 4.39; Cl, 19.37; S, 8.73. Found: C, 58.43; H, 4.47; Cl, 19.45; S, 8.82.

EXAMPLE 5

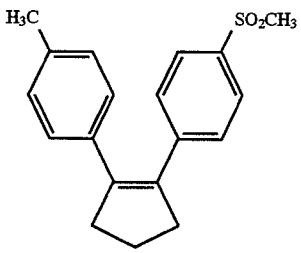

1-[2-(4-Methylphenyl)cyclopenten-1-yl]-4-(methylsulfonyl)benzene

Step 1: Preparation of 1-[2-(4-methylphenyl)cyclopenten-1-yl]-4-(methylthio)benzene.

Following the synthetic procedure outlined in Step 3 of Example 1, 250 mg (0.93 mmol) of 1-(2-bromocyclopenten-1-yl)-4-(methylthio)benzene (Example 1, Step 2) was reacted with 260 mg (1.9 mmol) of 4-methylphenylboronic acid (Lancaster). Purification by silica gel chromatography (MPLC) with hexane gave 240 mg (92%) of 1-[2-(4-methyl phenyl)cyclopenten-1-yl]-4-(methylthio)benzene as a colorless solid: mp 64.5°–66.5° C.; NMR (CDCl$_3$) δ 2.03 (m, J=7 Hz, 2H), 2.30 (s, 3H), 2.45 (s, 3H), 2.86 (t, J=7 Hz, 4H), 6.99–7.15 (m, 8H).

Step 2: Preparation of 1-[2-(4-methylphenyl)cyclopenten-1-yl]-4-(methylsulfonyl)benzene.

Following the synthetic procedure outlined in Step 4 of Example 1, 210 mg (0.75 mmol) of 1-[2-(4-methylphenyl)cyclopenten-1-yl]-4-(methylthio)benzene (Step 1) was oxidized. Purification by silica gel chromatography (MPLC) with ethyl acetate/hexane (1:4) and subsequent recrystallization gave 140 mg (60%) of 1-[2-(4-methylphenyl)cyclopenten-1-yl]-4 (methylsulfonyl)benzene as a colorless solid: mp 118.0°–118.5° C.; NMR (CDCl$_3$) δ2.07 (m, J=7 Hz, 2H), 2.32 (s, 3H), 2.90 (t, J=7 Hz, 4H), 3.03 (s, 3H), 6.99–7.08 (m, 4H), 7.34 (d, J=8 Hz, 2H), 7.74 (d, J=8 Hz, 2H); MS (EI) m/e (rel intensity) 312 (100), 297 (10), 233 (11) 218 (22); HRMS. Calc'd for C$_{19}$H$_{20}$O$_2$S: 312.1184. Found: 312.1194. Anal. Calc'd for C$_{19}$H$_{20}$O$_2$S: C, 73.04; H, 6.85; S, 10.26. Found: C, 73.22; H, 6.65; S, 10.24.

EXAMPLE 6

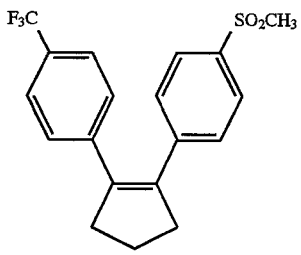

1-[2-(4-Trifluoromethylphenyl)cyclopenten-1-yl]-4-(methylsulfonyl)benzene

Step 1: Preparation of 4-Trifluoromethylphenylboronic acid

Following the synthetic procedure outlined in Step 1 of Example 1, 4-bromobenzotrifluoride (Aldrich) was converted to 4-trifluoromethyl phenylboronic acid: NMR (DMSO-d$_6$) δ7.68 (d, J=8 Hz, 2H), 7.98 (d, J=8 Hz, 2H).

Step 2: Preparation of 1-[2-(4-Trifluoromethylphenyl)cyclopenten-1-yl]-4-(methylthio)benzene Following the synthetic procedure outlined in Step 3 of Example 1, 240 mg (0.89 mmol) of 1-(2-bromocyclopenten-1-yl)-4-(methylthio)benzene (Example 1, Step 2) was reacted with 360 mg (1.8 mmol) of 4-trifluoromethylphenylboronic acid (Step 1). Purification by silica gel chromatography (MPLC) with hexane gave 240 mg (81%) of 1-[2-(4-trifluoromethylphenyl)cyclopenten-1-yl]-4-(methylthio)benzene as a colorless solid: mp 60.0°–61.5° C.; NMR (CDCl$_3$) δ2.06 (m, J=7 Hz, 2H), 2.46 (s, 3H), 2.89 (t, J=7 Hz, 4H), 7.06 (d, J=6 Hz, 2H), 7.10 (d, J=6 Hz, 2H), 7.27 (d, J=8 Hz, 2H), 7.46 (d, J=8 Hz, 2H).

Step 3: Preparation of 1-[2-(4-trifluoromethylphenyl)cyclopenten-1-yl]-4-(methylsulfonyl)benzene Following the synthetic procedure outlined in Step 4 of Example 1, 215 mg (0.75 mmol) of 1-[2-(4-trifluoromethylphenyl)cyclopenten-1-yl]-4-(methylthio) benzene (Step 2) was oxidized. Purification by silica gel chromatography (MPLC) with ethyl acetate/hexane (1:4) and subsequent recrystallization gave 163 mg (69%) of 1-[2-(4-trifluoromethylphenyl)cyclopenten-1-yl]-4-(methylsulfonyl)benzene as a colorless solid: mp 134.5°–135.0° C.; NMR (CDCl$_3$) δ2.12 (m, J=7 Hz, 2H), 2.95 (t, J=7 Hz, 4H), 3.05 (s, 3H), 7.24 (d, J=8 Hz, 2H), 7.31 (d, J=8 Hz, 2H), 7.49 (d, J=8 Hz, 2H), 7.78 (d, J=8 Hz, 2H); MS (EI) m/e (rel intensity) 312 (100), 297 (10), 233 (11) 218 (22); HRMS. Calc'd for C$_{19}$H$_{20}$O$_2$S: 312.1184. Found: 312.1194. Anal. Calc'd for C$_{19}$H$_{20}$O$_2$S: C, 73.04; H, 6.45; S, 10.26. Found: C, 73.22; H, 6.65; S. 10.24.

EXAMPLE 7

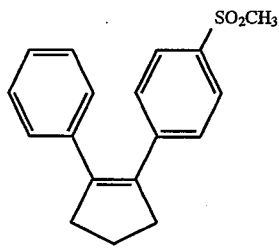

1-(2-Phenylcyclopenten-1-yl)-4-(methylsulfonyl) benzene

Step 1: Preparation of 1-bromo-2-phenylcyclopentene

Following a synthetic procedure which was similar to the one outlined in Step 2 of Example 1, 4.40 g (19.4 mmol) of 1,2-dibromocyclopentene was reacted with 2.0 g (17.7 mmol) of phenylboronic acid (Aldrich). Purification by silica gel chromatography (Waters Prep-500) with hexane gave 1.61 g (42%) of 1-bromo-2-phenylcyclopentene as an oil: NMR (CDCl$_3$) δ2.01–2.10 (m, 2H), 2.74–2.82 (m, 2H), 2.82–2.90 (m, 2H), 7.27–7.33 (m, 1H), 7.33–7.41 (m, 2H), 7.57–7.63 (m, 2H).

Step 2: Preparation of 1-(2-(phenylcyclopenten-3-yl)-4-(methylthio)benzene

Following a synthetic procedure which was similar to the one outlined in Step 3 of Example 1, 750 mg (3.4 mmol) of 1-bromo-2-phenylcyclopentene (Step 1) was reacted with 1.2 g (6.8 mmol) of 4-methylthiophenylboronic acid (Example 1, Step 1). Purification by silica gel chromatography (MPLC) with hexane gave 800 mg (89%) of 1-(2-phenylcyclopenten-1-yl)-4-(methylthio)benzene as an oil: NMR (CDCl$_3$) δ 2.00–2.17 (m, 2H), 2.46 (s, 3H), 2.86–3.01 (m, 4H), 7.08–7.19 (m, 4H), 7.19–7.32 (m, 5H).

Step 3: Preparation of 1-(2-(phenylcyclopenten-1-yl)-4-(methylsulfonyl)benzene

Following the synthetic procedure outlined in Step 4 of Example 1, 800 mg (3.0 mmol) of 1-(2-phenylcyclopenten-1-yl)-4-(methylthio) benzene (Step 2) was oxidized. Purification by silica gel chromatography (MPLC) with hexane gave 300 mg (30%) of 1-(2-phenylcyclopenten-1-yl)-4-(methylsulfonyl) benzene as a colorless solid: mp 135.5°–137.0° C.; NMR (DMSO-d$_6$) δ2.01 (m, J=7 Hz, 2H), 2.91 (t, J=7 Hz, 4H), 3.18 (s, 3H), 7.12–7.18 (m, 2H), 7.18–7.31 (m, 3H), 7.37 (d, J=8 Hz, 2H), 7.76 (d, J=8 Hz, 2H); MS (EI) m/e (rel intensity) 298 (100), 219 (30), 141 (30). HRMS. Calc'd for C$_{18}$H$_{18}$O$_2$S: 298.1028. Found: 298.1056. Anal. Calc'd for C$_{18}$H$_{18}$O$_2$S: C, 72.45; H, 6.08; S, 10.74. Found: C, 72.46; H, 6.17; S, 10.56.

EXAMPLE 8

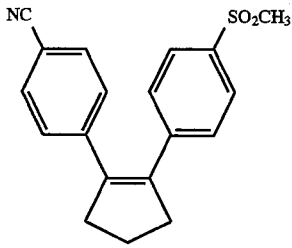

1-[2-(4-Cyanophenyl)cyclopenten-1-yl]-4-(methylsulfonyl)benzene

Step 1: Preparation of 4-cyanophenylboronic acid

Following the synthetic procedure outlined in Step 1 of Example 1, 4-bromobenzonitrile (Aldrich) was converted to 4-cyanophenylboronic acid: NMR (DMSO-d$_6$) δ 7.76 (d, J=7 Hz, 2H), 7.91 (d, J=8 Hz, 2H).

Step 2: preparation of 1-[2-(4-cyanophenyl) cyclopenten-1-yl]-4-(methylthio)benzene Following the synthetic procedure outlined in Step 3 of Example 1, 500 mg (1.9 mmol) of 1-(2-bromocyclopenten-1-yl)-4-(methylthio) benzene (Example 1, Step 2) was reacted with 540 mg (3.7 mmol) of 4-cyanophenylboronic acid (Step 1). Purification by silica gel chromatography (MPLC) with hexane/ethyl acetate (19:1) gave 480 mg (89%) of 1-[2-(4-cyanophenyl)cyclopenten-1-yl]-4-(methylthio)benzene as an oil: NMR (CDCl$_3$) δ2.07 (m, J=7 Hz, 2H), 2.42 (s, 3H), 2.89 (t, J=7 Hz, 4H), 7.05 (d, J=8 Hz, 2H), 7.11 (d, J=8 Hz, 2H), 7.26 (d, J=8 Hz, 2H), 7.48 (d, J=8 Hz, 2H).

Step 3: Preparation of 1-[2-(4-cyanophenyl) cyclopenten-1-yl]-4-(methylsulfonyl)benzene Following the synthetic procedure outlined in Step 4 of Example 1, 240 mg (0.82 mmol) of 1-[2-(4-cyanophenyl) cyclopenten-1-yl]-4-(methylthio)benzene (Step 2) was oxidized. Purification by silica gel chromatography (MPLC) with ethyl acetate/hexane (3:7) and subsequent recrystallization gave 174 mg (66%) of 1-[2-(4-cyanophenyl) cyclopenten-1-yl]-4-(methylsulfonyl)benzene as a colorless solid: mp 163.0°–164.5° C.; NMR (CDCl$_3$) δ2.13 (m, J=7 Hz, 2H), 2.95 (t, J=7 Hz, 4H), 3.05 (s, 3H), 7.22 (d, J=8 Hz, 2H), 7.30 (d, J=8 Hz, 2H), 7.51 (d, J=8 Hz, 2H), 7.79 (d, J=8 Hz, 2H); MS (EI) m/e (rel intensity) 323 (100), 308 (4), 244 (42); HRMS. Calc'd for C$_{19}$H$_{17}$NO$_2$S: 323.0980. Found: 323.1014. Anal. Calc'd for C$_{19}$H$_{17}$NO$_2$S: C, 70.56; H, 5.30; N, 4.33; S, 9.91. Found: C, 70.59; H, 5.34; N, 4.29; S, 9.67.

EXAMPLE 9

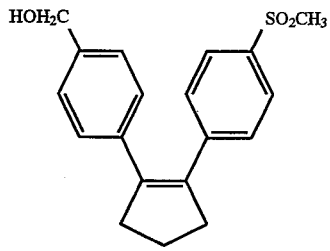

1-[2-(4-Hydroxymethylphenyl)cyclopenten-1-yl]-4-(methylsulfonyl)benzene

Step 1: Preparation of 4-hydroxymethylphenylboronic acid

Following the synthetic procedure outlined in Step 1 of Example 1, 4-bromobenzyl alcohol (Aldrich) was converted to 4-hydroxymethylphenyl boronic acid: NMR (DMSO-d$_6$) δ4.50 (d, J=5 Hz, 2H), 5.08 (s, 1H), 7.20–7.45 (m, 2H), 7.68–7.90 (m, 2H).

Step 2: Preparation of 1-[2-(4-hydroxymethylphenyl) cyclopenten-1-yl]-4-(methylphio)benzene Following the synthetic procedure outlined in Step 3 of Example 1, 250 mg (0.93 mmol) of 1-(2-bromocyclopenten-1-yl)-4-(methylthio) benzene (Example 1, Step 2) was reacted with 290 mg (1.9 mmol) of 4-hydroxymethylphenylboronic acid (Step 1). Purification by silica gel chromatography (MPLC) with ethyl acetate/ hexane (1:4) gave 255 mg (92%) of 1-[2-(4-hydroxymethylphenyl)cyclopenten-1-yl]-4-(methylthio) benzene as a solid: mp 82°–85° C.; NMR (CDCl$_3$) δ2.04 (m, J=7 Hz, 2H), 2.45 (s, 3H), 2.88 (t, J=7 Hz, 4H), 4.64 (s, 2H), 7.08 (s, 4H), (m, 2H), 7.15–7.25 (m, 4H).

61

Step 3: Preparation of 1-[2-(4-hydroxymethylphenyl) cyclopenten-1-yl]-4-(methylsulfonyl) benzene Following the synthetic procedure outlined in Step 4 of Example 1, 210 mg (0.71 mmol) of 1-[2-(4-hydroxymethylphenyl) cyclopenten-1-yl]-4-(methylthio) benzene (Step 2) was oxidized. Purification by silica gel chromatography with hexane/ethyl acetate (1:4) and subsequent recrystallization from ethyl acetate/hexane gave 1-[2-(4-hydroxymethylphenyl)cyclopenten-1-yl]-4-(methylsulfonyl)benzene as a colorless solid: mp 114°–115° C.; NMR (CDCl$_3$) δ2.09 (m, J=7 Hz, 2H), 2.92 (t, J=7 Hz, 4H), 3.03 (s, 3H), 4.67 (s, 2H), 7.13 (d, J=8 Hz, 2H), 7.24 (d, J=8 Hz, 1H), 7.33 (d, J=8 Hz, 2H), 7.74 (d, J=8 Hz, 2H); MS (EI) m/e (rel intensity) 328 (100), 311 (10), 297 (21), 218 (53); HRMS. Calc'd for C$_{19}$H$_{20}$O$_3$S: 328.1133. Found: 328.1147. Anal. Calc'd for C$_{19}$H$_{20}$O$_3$S: C, 69.48; H, 6.14; S, 9.76. Found: C, 69.51; H, 6.40; S, 9.68.

EXAMPLE 10

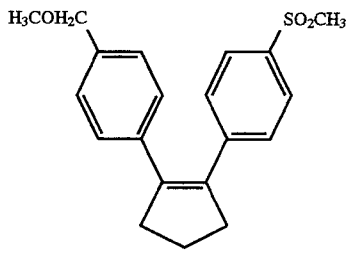

1-[2-(4-Methoxymethylphenyl)cyclopenten-1-yl]-4-(methylsulfonyl)benzene

Under nitrogen, a stirred solution of 79 mg (0.24 mmol) of 1-[2-(4-hydroxymethylphenyl)cyclopenten-1-yl]-4-(methylsulfonyl)benzene (Example 9) in 2 mL of dry THF at 0° C. was treated with 15 mg (0.6 mmol) of sodium hydride (95%). After 30 minutes, 0.1 mL (1.6 mmol) of methyl iodide was added and the reaction was allowed to warm to ambient temperature overnight. The solvent was removed in vacuo; the residue was dissolved in ethyl acetate and washed with water, dried (MgSO$_4$), and reconcentrated. Purification by silica gel chromatography (MPLC) with hexane/ethyl acetate (5:1) and subsequent lyophilization from acetonitrile/water (1:1) gave 25 mg (30%) of 1-[2-(4-methoxymethylphenyl)cyclopenten-1-yl]-4-(methylsulfonyl)benzene as a colorless solid: NMR (CDCl$_3$) δ2.09 (m, J=7 Hz, 2H), 2.92 (t, J=7 Hz, 4H), 3.03 (s, 3H), 3.40 (s, 3H), 4.42 (s, 2H), 7.12 (d, J=8 Hz, 2H), 7.20 (d, J=8 Hz, 2H), 7.33 (d, J=8 Hz, 2H), 7.73 (d, J=8 Hz, 2H); MS (EI) m/e (rel intensity) 342 (100), 81 (27), 69 (62). HRMS. Calc'd for C$_{20}$H$_{22}$O$_3$S: 342.1290. Found: 342.1301. Anal. Calc'd for C$_{20}$H$_{22}$O$_3$S: C, 70.15; H, 6.48; S, 9.36. Found: C, 69.86; H, 6.64; S, 9.38.

62

EXAMPLE 11

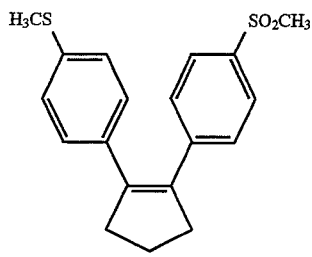

1-[2-(4-Methylthiophenyl)cyclopenten-1-yl]-4-(methylsulfonyl)benzene

Step 1: Preparation of 1-(2-bromocyclopenten-1-yl)-4-(methylsulfonyl)benzene

Following the synthetic procedure outlined in Step 4 of Example 1, 250 mg (0.93 mmol) of 1-(2-bromocyclopenten-1-yl)-4-(methylthio)benzene (Example 1, Step 2) was oxidized to give 280 mg (100%) of 1-(2-bromocyclopenten-1-yl)-4-(methylsulfonyl)benzene as a colorless solid: mp 103°–104° C.; NMR (CDCl$_3$) δ2.02–2.14 (m, 2H), 2.74–2.83 (m, 2H), 2.86–2.94 (m, 2H), 3.07 (s, 3H), 7.77 (d, J=8 Hz, 2H), 7.93 (d, J=8 Hz, 2H).

Step 2: Preparation of 1-[2-(4-methylthiophenyl) cyclopenten-1-yl]-4-(methylsulfonyl)benzene Following a synthetic procedure which was similar to the one outlined in Step 3 of Example 1, 270 mg (0.9 mmol) of 1-(2-bromocyclopenten-1-yl)-4-(methylsulfonyl)benzene (Step 1) was reacted with 300 mg (1.8 mmol) of 4-methylthiophenylboronic acid (Example 1, Step 1). Purification by silica gel chromatography (MPLC) with hexane/ethyl acetate (4:1) gave 265 mg (86%) of 1-[2-(4-methylthiophenyl)cyclopenten-1-yl]-4-(methylsulfonyl) benzene as a colorless solid: mp 138°–139° C.; NMR (CDCl$_3$) δ2.08 (m, J=7 Hz, 2H), 2.47 (s, 3H), 2.90 (t, J=7 Hz, 4H), 3.04 (s, 3H), 7.06 (d, J=8 Hz, 2H), 7.11 (d, J=8 Hz, 2H), 7.34 (d, J=8 Hz, 2H), 7.75 (d, J=8 Hz, 2H); MS (EI) m/e (rel intensity) 344 (100), 297 (4), 218 (33); HRMS. Calc'd for C$_{19}$H$_{20}$O$_2$S$_2$: 344.0905. Found: 344.0907. Anal. Calc'd for C$_{19}$H$_{20}$O$_2$S2: C, 66.24; H, 5.85; S, 18.16. Found: C, 66.28; H, 5.81; S, 18.95.

EXAMPLE 12

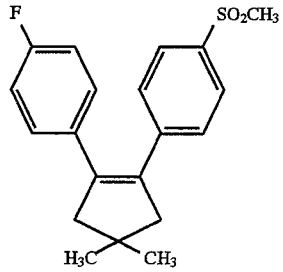

1-[2-(4-Fluorophenyl)-4,4-dimethylcyclopenten-1-yl]-4-(methylsulfonyl)benzene

Step 3: Preparation of the ethyl acetal of mucobromic acid

Under nitrogen, a stirred solution of 500 g (1.94 mol) of mucobromic acid (Lancaster) and 2 g of p-toluenesulfonic acid monohydrate in 600 mL of toluene and 400 mL of absolute ethanol was heated to reflux for 6 hours during which time 150 mL of a water, toluene, and ethanol azeotrope was removed by distillation. The solution was concentrated in vacuo; the residue was dissolved in 1500 mL of ethyl acetate and washed successively with water, saturated sodium carbonate, and brine, dried ($Na_2SO_4$), and reconcentrated to give 440 g (79%) of the ethyl acetal of mucobromic acid (5 in Synthetic Scheme II) as an oil: NMR ($CDCl_3$) δ1.31 (t, J=7 Hz, 3H), 3.73–3.96 (m, 2H), 5.81 (s, 1H).

Step 2; Preparation of cis-2,3-dibromobut-2-ene-1,4-diol

Under nitrogen, a stirred solution of 150 g (525 mmol) of the ethyl acetal of mucobromic acid (Step 1) in 150 mL of anhydrous THF at −78° C. was treated with 1400 mL of diisobutylaluminumhydride (1.5M in toluene) over a 30 minute period. The solution was allowed to warm to ambient temperature and stirred for 2 hours. The reaction was slowly treated (maintaining the temperature below 10° C.) with 100 mL of acetone followed by 50 mL of 2.5N sodium hydroxide. Water (1000 mL) was added and the solution extracted 5 times with ethyl acetate. The combined extracts were washed with brine, dried ($Na_2SO_4$), and concentrated. The residue was washed 3 times with hexane and dried in vacuo to give 88.5 g (69%) of cis-2,3-dibromo-2-ene-1,4-diol (6 in Synthetic Scheme II) as a colorless solid: mp 66°–67° C.; NMR (DMSO-$d_6$) δ4.27 (d, J=6 Hz, 4H), 5.44 (t, J=6 Hz, 2H).

Step 3: Preparation of cis-1,2,3,4-tetrabromobut-2-ene

Under nitrogen, a stirred solution of 25.2 g (102 mmol) of cis-2,3-dibromobut-2-ene-1,4-diol (Step 2) in 150 mL of methylene chloride at 0° C. was treated with 9.6 mL of phosphorus tribromide. The solution was allowed to warm to ambient temperature where it was allowed to stir for 1 hour prior to the addition of ice water. The aqueous phase was extracted 5 times with methylene chloride; these extracts were combined with the original methylene chloride phase and washed with water, saturated sodium carbonate, brine, dried ($Na_2SO_4$), and concentrated in vacuo to give 18 g (47%) of cis-1,2,3,4-tetrabromobut-2-ene [7 (X=Br) in Synthetic Scheme II] as an oil: NMR ($CDCl_3$) δ4.40 (s, 4H).

Step 4: Preparation of 1,2-dibromo-4,4-di(carboethoxy) cyclopentene

Under nitrogen, a solution of 9.7 g (60.6 mmol) of diethyl malonate in anhydrous THF at −10° C. was treated with 2.9 g (121 mmol) of sodium hydride (95%) and allowed to stir for 30 minutes. The resulting solution was then added slowly to 15 g (40.4 mmol) of cis-1,2,3,4-tetrabromobut-2-ene (Step 3) in 350 mL of anhydrous THF at −78° C.. The reaction was allowed to warm to ambient temperature overnight prior to concentration in vacuo. The residue was dissolved in ethyl acetate and washed with water, dried ($Na_2SO_4$), and reconcentrated. Purification by silica gel chromatography (Waters Prep-500) with ethyl acetate/ hexane (1:99) gave 3.7 g (25%) of 1,2,-dibromo-4,4-di (carboethoxy)cyclopentene (8 in Synthetic Scheme II) as a colorless oil: NMR ($CDCl_3$) δ1.26 (t, J=7 Hz, 6H), 3.26 (s, 4H), 4.22 (m, J=7 Hz, 4H); MS (FAB) for M+H m/e: 373, 371, 369.

Step 5: Preparation Of 1,2-dibromo-4,4-di(hydroxymethyl) cyclopentene

Under nitrogen, a stirred solution of 8.7 g (23.5 mmol) of 1,2-dibromo-4,4-di(carboethoxy)cyclopentene (Step 4) in 70 mL of anhydrous THF at −78° C. was treated with 80 mL of diisobutylaluminum hydride (1.5M in toluene) over a 20 minute period. The reaction was allowed to warm to ambient temperature overnight and was slowly treated with 20 mL of acetone followed by 10 mL of 2.5N sodium hydroxide. Water (100 mL) was added and the solution extracted 5 times with ethyl acetate. The combined extracts were washed with brine, dried ($Na_2SO_4$), and concentrated in vacuo to give 5.7 g (85%) of 1,2-dibromo-4,4-di (hydroxymethyl)cyclopentene (10 in Synthetic Scheme III) as a colorless oil: NMR ($CDCl_3$) δ 2.20 (s, 2H), 2.50 (s, 4H), 3.70 (s, 4H).

Step 6: Preparation of 1,2-dibromo-4,4-di(tosylmethyl) cyclopentene

Under nitrogen, a stirred solution of 5.7 g (19.9 mmol) of 1,2-dibromo-4,4-di(hydroxymethyl)cyclopentene (Step 5) in 50 mL of pyridine at ambient temperature was treated with 19 g (99.7 mmol) of p-toluenesulfonyl chloride. The reaction was allowed to stir overnight and was concentrated in vacuo. The residue was dissolved ethyl acetate and washed twice with 3% hydrochloric acid followed by brine. The solution was dried ($Na_2SO_4$) and concentrated in vacuo to give 5.2 g (44%) of 1,2-dibromo-4,4-di(tosylmethyl) cyclopentene (14 in Synthetic Scheme V) as a colorless semisolid: NMR ($CDCl_3$) δ2.42 (s, 4H), 2.47 (s, 6H), 3.90 (s, 4H), 7.37 (d, J=8 Hz, 4H), 7.74 (d, J=8 Hz, 4H).

Step 7; Preparation of 1,2-dibromo-4,4-di(iodomethyl) cyclopentene

Under nitrogen, a stirred solution of 5.2 g (8.7 mmol) of 1,2-dibromo-4,4-di(tosylmethyl)cyclopentene (Step 6) and 13 g (86 mmol) of sodium iodide in 40 mL of DMF/$H_2O$ (3:1) was heated to 150° C. in an oil bath overnight. The reaction was cooled, diluted with 200 mL of ethyl acetate, and washed with water. Drying ($Na_2SO_4$) and concentrating in vacuo gave 3.7 g (84%) of 1,2-dibromo-4,4-di (iodomethyl)cyclopentene (15 in Synthetic Scheme V) as an oil: NMR ($CDCl_3$) δ2.70 (s, 4H), 3.50 (s, 4H).

Step 8:Preparation of 1,2-dibromo-4,4-dimethylcyclopentene.

Under nitrogen, a stirred solution of 3.7 g (7.3 mmol) of 1,2-dibromo-4,4-di(iodomethyl)cyclopentene (Step 7) and 1.3 g (20.6 mmol) of sodium cyanoborohydride in 15 mL of hexamethylphosphoramide (HMPA) was heated to 100 ° C. in an oil bath overnight. The reaction was cooled, diluted with 50 mL of water, and extracted 5 times with ethyl acetate/hexane (1:5). The combined extracts were washed 3 times with water, dried ($Na_2SO_4$), and concentrated in vacuo. Purification by silica gel chromatography (Waters Prep-500) with hexane gave 1.3 g (70%) of 1,2-dibromo-4, 4-dimethylcyclopentene (16 in Synthetic Scheme V) as a colorless oil: NMR ($CDCl_3$) δ1.16 (s, 6H), 2.44 (s, 4H); MS (EI) m/e (rel intensity) 256 (24), 254 (63), 252(44), 175 (26), 173 (29), 94 (100).

Step 9: Preparation of 1-[2-(4-fluorophenyl)-4,4-dimethylcyclopenten-1-yl]-4-(methylthio) benzene Under nitrogen, 1.3 g (5.1 mmol) of 1,2-dibromo-4,4-dimethylcyclopentene (Step 8) was reacted with 600 mg (4.3 mmol) of 4-fluorophenylboronic acid (Lancaster) in 23 mL of toluene, 15 mL of ethanol, and 10 mL of 2M $Na_2CO_3$ in the presence of 250 mg (5 mol %) of Pd($PPh_3$)$_4$. The reaction was vigorously stirred at reflux overnight and concentrated in vacuo. The residue was dissolved in ethyl acetate and washed with water, dried ($Na_2SO_4$), and reconcentrated. Purification by silica gel chromatography (MPLC) with hexane gave 250 mg of 1-(2-bromocyclopenten-1-yl)-4-fluorobenzene (38 in Synthetic Scheme X when $R^1$ and $R^2$=$CH_3$, $R^5$=F, $R^3$, $R^4$, $R_6$, and $R^7$=H) as a pale yellow oil which was reacted with 200 mg (1.2 mmol) of 4-methylthiophenylboronic acid (Example 1, Step 1) in 5.2 mL of toluene, 3.4 mL of ethanol, and 2.2 mL of 2M $Na_2CO_3$ in the presence of 40 mg (5 mol %) of Pd($PPh_3$)$_4$. The reaction was vigorously stirred at reflux for 6 hours and concentrated in vacuo. The residue was dissolved in ethyl acetate and washed with water, dried ($Na_2SO_4$), and reconcentrated. Purification by silica gel chromatography (MPLC) with hexane gave 120 mg of 1-[2-(4-fluorophenyl)-4,4-dimethyl cyclopenten-1-]-4-(methylthio)benzene (41 in Synthetic Scheme X when $R^1$ and $R^2$=$CH_3$, $R^5$=F, $R^{10}$=$SCH_3$, $R^3$, $R^4$, $R^6$, $R^7$, $R^8$, $R^9$, $R^{11}$, and $R^{12}$=H) as an oil: NMR (CDCl$_3$) δ1.20 (s, 6H0, 2.42 (s, 3H), 2.63 (s, 4H), 6.90 (t, J=8 Hz, 2H), 7.00–7.18 (m, 4H), 7.30–7.60 (m, 2H).

Step 10: Preparation of 1-[2-(4-fluorophenyl)-4,4-dimethylcyclopenten-1-yl]-4-(methylsulfonyl)benzene A solution of 120 mg (0.39 mmol) of 1-[2-(4-fluorophenyl)-4,4-dimethylcyclopenten-1-yl]-4-(methylthio)benzene (Step 9) in 3 mL of methanol/water (1:1) was slowly treated with 470 mg (0.76 mmol) of Oxone® [2 $KHSO_5.KHSO_4.K_2SO_4$] in 2 mL of water. After stirring for 4 hours, the solvent was removed in vacuo. The residue was dissolved in ethyl acetate and washed with water and brine, dried ($MgSO_4$), and reconcentrated. Purification by silica gel chromatography (MPLC) with hexane/ethyl acetate (5:1) and subsequent lyophilization from acetonitrile/water (1:1) gave 50 mg (38%) of 1-[2-(4-fluorophenyl)-4,4-dimethyl cyclopenten-1-yl]-4-(methylsulfonyl)benzene (41 in Synthetic Scheme X when $R^1$ and $R^2$=$CH_3$, $R^5$=, $R^{10}$=$SO_2CH_3$, $R^3$, $R^4$, $R^6$, $R^7$, $R^8$, $R^9$, $R^{11}$, and $R^{12}$=H) as a colorless solid: NMR (CDCl$_3$) d 1.24 (s, 6H), 2.71 (s, 4H), 3.4 (s, 3H), 6.92 (t, J=8 Hz, 2H), 7.05–7.12 (m, 2H), 7.30 (d, J=9 Hz, 2H), 7.75 (d, J=9 Hz, 3H); MS (EI) m/e (rel intensity) 344 (100), 329 (33), 250 (18), 235 (20), 109 (35), 69 (44); HRMS. Calc'd for $C_{20}H_{21}FO_{2}S$: 344.1246. Found: 344.1272.

EXAMPLE 13

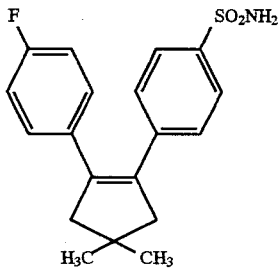

4-[2-(4-Fluorophenyl)-4,4-dimethylcyclopenten-1-yl]benzenesulfonamide

Under nitrogen, a solution of 4.55 g (13.2 mmol) of 1-[2-(4-fluorophenyl)-4,4-dimethylcyclopenten-1-yl]-4-(methylsulfonyl)benzene (the title compound of Example 12) in 50 mL of THF at −78° C. was treated with 6.3 mL (15.8 mmol) of n-butyllithium (2.5M in hexane) over a period of 5 minutes. The reaction was stirred at ambient temperature for 25 minutes, cooled to −78° C., and treated with 19.8 mL (19.8 mmol) of tributylborane (1.0M in THF). The resulting dark brown solution was stirred at ambient temperature for 20 minutes and then at reflux for 16 hours prior to the addition of 8.7 g (106 mmol) of sodium acetate, 10 mL of water, and 5.2 g (46 mmol) of hydroxyamine-O-sulfonic acid. The resulting light orange mixture was stirred at ambient temperature for 3 hours and the aqueous phase extracted with ethyl acetate. The combined extracts were washed first with water and then with brine, dried ($MgSO_4$), and concentrated in vacuo. The residue was chromatographed on silica gel to give 2.0 g (44%) of 4-[2-(4-fluorophenyl)-4,4-dimethylcyclopenten-1-yl] benzenesulfonamide as a colorless solid: mp 117°–18° C.; NMR (CDCl$_3$) δ1.23 (s, 6H), 2.70 (s, 4H), 4.72 (s, 2H), 6.92 (t, J=9 Hz, 2H), 7.05–7.12 (m, 2H), 7.26 (d, J=9 Hz, 2H), 7.74 (d, J=9 Hz, 2H); MS (EI) m/e (rel intensity) 345 (100), 330 (39), 250 (28), 109 (50), 80 (31), 69 (58); HRMS. Calc'd for $C_{19}H_{20}FNO_2S$: 45.1199. Found: 345.1194. Anal. Calc'd for [$C_{19}H_{20}FNO_2S$+0.27 $H_2O$]: C, 65.15; H, 5.91; N, 4.00; S, 9.15. Found: C, 65.07; H, 5.94; N, 3.86; S, 9.29.

EXAMPLE 14

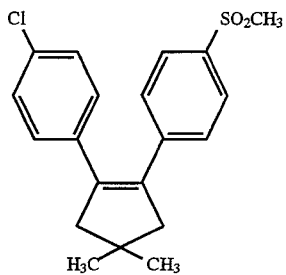

1-[2-(4-Chlorophenyl)-4,4-dimethylcyclopenten-1-yl]-4-(methylsulfonyl)benzene

Following the general procedures outlined in Synthetic Schemes XV, XX, XXI, and XXII, 1-[2-(4-chlorophenyl)-4,4-dimethylcyclopenten-1-yl]-4-(methylsulfonyl)benzene was isolated as a colorless solid: mp 144°–145° C.; NMR (CDCl$_3$) d 1.23 (s, 6H), 2.71 (s, 4H), 3.04 (s, 3H), 7.05 (d, J=8 Hz, 2H), 7.21 (d, J=8 Hz, 2H), 7.30 (d, J=8 Hz, 2H), 7.76 (d, J=8 Hz, H); MS (EI) m/e (rel intensity) 360 (100), 345 (30), (20), 231 (20); HR/4S. Calc'd for $C_{20}H_{21}ClLiO_2S$: 367.1111. Found: 367.1105. Anglo Calc'd for $C_{20}H_{21}ClO_2S$: C, 66.50; H, 5.82; Cl, 9.84. Found: C, 66.61; H, 6.10, Cl, 9.85.

EXAMPLE 15

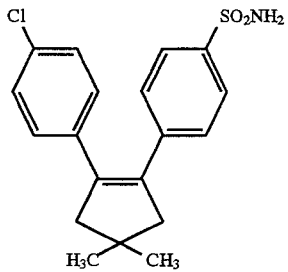

4-[2-(4-Chlorophenyl)-4,4-dimethylcyclopenten-1-yl]benzenesulfonamide

Following the general procedure outlined in Synthetic Scheme XXIII, 1-[2-(4-chlorophenyl)-4,4-dimethylcyclopenten-1-yl]-4-(methylsulfonyl) benzene (the title compound of Example 14) was converted to 4-[2-(4-chlorophenyl)-4,4-dimethylcyclopenten-1-yl] benzenesulfonamide as a colorless solid: mp 144°–145° C.; NMR (CDCl$_3$) δ1.24 (s, 6H), 2.71 (s, 4H), 4.78 (s, 2H), 7.05 (d, J=9 Hz, 2H), 7.20 (d, J=9 Hz, 2H), 7.26 (d, J=9 Hz, 2H), 7.75 (d, J=9 Hz, 2H); HRMS. Calc'd for $C_{19}H_{20}ClNO_2S$: 361.0903. Found: 361.0882. Anal. Calc'd for $C_{19}H_{20}ClNO_2S$: C, 62.72; H, 5.55; Cl, 10.31; S, 8.80. Found: C, 62.35; H, 5.71; Cl, 10.04; S, 8.74.

EXAMPLE 16

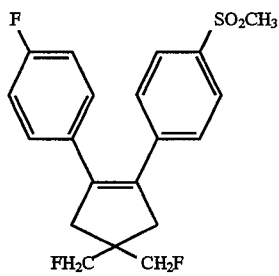

1-[2-(4-Fluorophenyl)-4,4-di(fluoromethyl)
cyclopenten-1-yl]-4-(methylsulfonyl)benzene Step 1: Preparation of 4-(methylthio)acetophenone To a stirred solution of 50 g (340 mmol) of 4-(methylthio) benzonitrile in 2 L of THF at −78° C. under an atmosphere of nitrogen, was added 282 mL (390 mmol) of methyllithium (1.4M in diethyl ether) over a period of ten minutes. The solution was stirred at −78° C. for one hour, and then the dry ice bath was removed. After five hours, 100 mL of water followed by 200 mL of 3N hydrochloric acid were added to the reaction mixture and it was stirred overnight. Concentration in vacuo gave a residue which was partitioned between ethyl acetate and water. The water layer was extracted with three portions of ethyl acetate and the combined ethyl acetate layers were dried (MgSO$_4$). Concentration in vacuo gave 58 g of crude (4-methylthio) acetophenone as a solid: NMR (CDCl$_3$) δ2.52 (s, 3H), 2.57 (s, 3H), 7.26 (d, J=9 Hz, 2H), 7.87 (d, J=9 Hz, 2H).

Step 2: Preparation of 4-(methylsulfonyl)acetophenone

To a solution of 11.73 g (71.1 mmol) of 4-(methylthio) acetophenone (prepared in Step 1) in 500 mL of dichloromethane at ambient temperature was added 61.14 g (177 mmol) of m-chloroperoxybenzoic acid (50%) (MCPBA) in portions over 20 minutes. The reaction was stirred for two hours, quenched slowly with aqueous sodium bisulfite, washed with three 100 mL portions of saturated sodium bicarbonate, dried (MgSO$_4$), and concentrated in vacuo to give 11.91 g (91%) of (4-methylsulfonyl)acetophenone as an colorless solid: NMR (CDCl$_3$) δ2.67 (s, 3H), 3.08 (s, 3H), 8.06 (d, J=9 Hz, 2H), 8.14 (d, J=9 Hz, 2H).

Step 3: Preparation of 2-bromo-4'-(methylsulfonyl) acetophenone

To a stirred solution of 11.91 g (60.5 mmol) of 4-(methylsulfonyl)acetophenone (prepared in Step 2) in 133 mL of glacial acetic acid and 0.11 mL of hydrochloric acid at ambient temperature was added a solution of 8.22 g (51.4 mmol) of bromine in 9.3 mL of glacial acetic acid over a period of three hours. The reaction mixture was diluted with 500 mL of water and extracted with chloroform. The combined extracts were dried (MgSO$_4$) and concentrated in vacuo to give 15.7 g of crude 2-bromo-(4'-methylsulfonyl) acetophenone as a solid: NMR (CDCl$_3$) δ3.10 (s, 3H), 4.45 (s, 2H), 8.08 (d, J=9 Hz, 2H), 8.17 (d, J=9 Hz, 2H).

Step 4: Preparation of 2-(4-fluorophenyl)-1-[2-[4-(methylsulfonyl)phenyl]-2-oxoethoxy]ethanone To a stirred solution of 4.45 g (28.9 mmol) of 4-fluorophenylacetic acid in 3.26 g (31.8 mmol) of triethylamine and 275 mL of acetonitrile was added 8.9 g (28.9 mmol) of 2-bromo-4'-(methylsulfonyl)acetophenone (prepared in Step 3) at ambient temperature. The reaction mixture was stirred for 30 minutes, concentrated in vacuo, and partitioned between ethyl acetate and water. The organic phase was dried (MgSO$_4$) and concentrated in vacuo. Purification by silica gel chromatography with ethyl acetate/hexane (1:1) gave 6.87 g (68%) of 2-(4-fluorophenyl)-1-[2-[4-(methylsulfonyl)phenyl]-2-oxoethoxy]ethanone as a colorless solid: NMR (CDCl$_3$) δ3.08 (s, 3H), 3.79 (s, 2H), 5.35 (s, 2H), 7.06 (s, t, J=9 Hz, 2H), 7.32 (dd, J=6 and 9 Hz, 2H), 8.06 (s, 4H).

Step 5: Preparation of 3-(4-fluorophenyl)-4-[(4-methylsulfonyl)phenyl]-5H-furan-2-one Under nitrogen, 4.10 g (11.7 mmol) of 2-(4-fluorophenyl) -1-[2-[4-(methylsulfonyl)phenyl]-2-oxoethoxy]ethanone (prepared in Step 4), 6.52 mL (46.8 mmol) of triethylamine, 4.89 g (25.7 mmol) of p-toluenesulfonic acid, and 12 g of 4Å molecular sieves were added to 117 mL of acetonitrile and stirred at reflux for 16 hours. The reaction mixture was concentrated in vacuo and the residue partitioned between dichloromethane and water. The dichloromethane layer was dried (MgSO$_4$) and reconcentrated in vacuo. Recrystallization from hexane/ethyl acetate (2:1) gave 3.65 g (94%) of 3-(4-fluorophenyl)-4-[4-(methylsulfonyl)phenyl]-5H-furan-2-one as a solid: mp 166°–167° C.; NMR (CDCl$_3$) δ3.08 (s, 3H), 5.19 (s, 2H), 7.10 (t, J=9 Hz, 2H), 7.42 (dd, J=6 and 9 Hz, 2H), 7.52 (d, J=9 Hz, 2H), 7.97 (d, J=9 Hz, 2H); HRMS. Calc'd for C$_{17}$H$_{13}$FO$_{4}$S: 332.0519. Found: 332.0501. Anal. Calc'd for C$_{17}$H$_{13}$FO$_{4}$S: C, 61.44; H, 3.94; O, 19.26. Found: C, 61.11; H, 4.06; O, 19.32.

Step 6: Preparation of 2-(4-fluorophenyl)-3-[(4-methylsulfonyl)phenyl]-1,4-dihydroxy-2-butene To a solution of 3.08 g (9.28 mmol) of 3-(4-fluorophenyl) -4-(4-methylsulfonyl)phenyl]-5H-furan-2-one (prepared in Step 5) in 93 mL of tetrahydrofuran (THF) at −78° C. under an atmosphere of nitrogen was added 20 mL (30 mmol) of diisobutylaluminumhydride (1.5M in THF) (DIBAL) over a 10 minute period. The solution was stirred at −78° C. for 20 minutes, allowed to warm to ambient temperature, and stirred overnight. An additional 15 mL (22 mmol) aliquot of DIBAL was added and stirring was continued for 2 hours. The reaction was cooled to −78° C., treated dropwise with 25 mL of acetone, warmed to room temperature, and slowly treated with 25 mL of water. The mixture was stirred for 30 minutes prior to the careful addition of 35 mL of 1.2N sodium hydroxide. The mixture was extracted with ethyl acetate, washed with 1N hydrochloric acid followed by brine, dried (MgSO$_4$), and concentrated in vacuo to give 3.8 g of crude 2-(4-fluorophenyl)-3-[(4-methylsulfonyl)phenyl] -1,4-dihydroxy-2-butene as a colorless oil: NMR (CDCl$_3$) δ2.98 (s, 3H), 4.60 (d, J=6 Hz, 4H), 6.8 (t, J=9 Hz, 2H), 6,94–7.02 (m, 2H), 7.22 (d, J=9 Hz, 2H), 7.65 (d, J=9 Hz, 2H).

Step 7: Preparation of 2-(4-fluorophenyl)-3-[(4-methylsulfonyl)phenyl]-1,4-dichloro-2-butene To a solution of 3.5 g (7.62 mmol) of crude 2-(4-fluorophenyl)-3-[(4-methylsulfonyl)phenyl]-1,4-dihydroxy-2-butene (prepared in Step 6) in 58 mL of N,N-dimethylformamide (DMF) at 5° C. under an atmosphere of nitrogen was added dropwise 1.52 mL (20.84 mmol) of thionyl chloride. The reaction was stirred at 5° C. for 22 hours, stirred at ambient temperature for an additional 8 hours, and concentrated in vacuo. The residue was partitioned between ethyl acetate and water; the ethyl acetate phase was dried (MgSO$_4$) and concentrated in vacuo to give crude 2-(4-fluorophenyl)-3-[(4-methylsulfonyl)phenyl]-1,4-dichloro-2-butene as a solid: NMR (CDCl$_3$) δ3.0 (s, 3H), 4.55 (d, J=3.4 Hz, 4H), 6.86 (t, J=9 Hz, 2H), 6.75 (d, J=8.3 Hz, 2H), 7.45 (d, J=9 Hz, 2H).

Step 8A: Preparation of 1-[2-(4-fluorophenyl)-4,4-dicarbomethoxycyclopenten-1-yl]-4-(methylsulfonyl) benzene To a solution of 1.2 mL (10.5 mmol) of dimethyl malonate in 10 mL of DMF under an atmosphere of nitrogen was added 215 mg (26.9 mmol) of lithium hydride in portions. The resulting suspension was stirred at ambient temperature for 20 minutes prior to the addition of a solution of crude 2-(4-fluorophenyl)-3-[(4-methylsulfonyl)phenyl]-1,4-dichloro-2-butene (prepared in Step 7) in 10 mL of DMF. The reaction was stirred at ambient temperature for 15 hours, treated with another 150 mg (18.8 mmol) of lithium hydride, and stirred for another 4 hours. The mixture was concentrated in vacuo and partitioned between ethyl acetate and water; the organic phase was dried (MgSO$_4$), and concentrated in vacuo. The residue was chromatographed on silica gel to give 1.1 g (34%) of 1-[2-(4-fluorophenyl)-4,4-dicarbomethoxycyclopenten-1-yl]-4-(methylsulfonyl)benzene as an oil: NMR (CDCl$_3$) δ3.03 (s, 3H), 3.55 (s, 4H), 3.79 (s, 6H), 6.93 (t, J=9 Hz, 2H), 7.11 (dd, J=6 and 9 Hz, 2H), 7.32 (d, J=9 Hz, 2H), 7.77 (d, J=9 Hz, 2H).

Step 8B: Preparation of 1-[2-(4-fluorophenyl)-4,4-dicarbomethoxycyclopenten-1-yl]-4-(methylsulfonyl)benzene To a solution of 7.18 mL (63 mmol) of dimethyl malonate in 160 mL of DMF at 0° C. under an atmosphere of nitrogen was added 3.0 g (75 mmol) of sodium hydride (60% suspension in oil). The reaction was stirred at ambient temperature for 15 minutes (or until the gas evolution has ceased), cooled to −20° C., and treated with 15 g (69 mmol) of 2-bromo-4'-fluoroacetophenone (Aldrich) in one portion. The mixture was stirred at ambient temperature for 1 hour and then cooled to 0° C.; another 75 mmol of sodium hydride was added and the resulting mixture stirred at ambient temperature for 15 minutes (or until the gas evolution has ceased). The reaction was recooled to −20° C. and treated with 19.1 g (69 mmol) of 2-bromo-4'-(methylsulfonyl)acetophenone (prepared in Step 3). The reaction was stirred at room temperature for 2 hours and concentrated in vacuo. The residue was partitioned between water and ethyl acetate; the ethyl acetate phase was dried (MgSO$_4$) and reconcentrated in vacuo. The residue was chromatographed on silica gel to give 13.8 g (51%) of dimethyl 2-[2-(4-fluorophenyl)-2-oxoethyl]-2-[2-[4-(methylsulfonyl)phenyl]-2-oxoethyl]propanedioate as an oil: NMR (CDCl$_3$) d 3.06 (s, 3H), 3.76 (s, 6H), 4.03 (s, 2H), 4.08 (s, 2H), 7.13 (t, J=8.6 Hz, 2H), 7.97–8.05 [m with d at 8.03 (J=8.7 Hz), 4H], 8.14 (d, J=8.5 Hz, 2H).

To a vigorously stirred mixture of 50.4 g (771 mmol) of zinc dust in 640 mL of THF at −78° C. under an atmosphere of nitrogen was added dropwise 60.4 mL (551 mmol) of titanium (IV) chloride. The reaction was warmed to ambient temperature with a water bath and then stirred at reflux for 1 hour. To the resulting dark mixture under reflux was added a solution of 15 g (32.3 mmol) of dimethyl 2-[2-(4-fluorophenyl)-2-oxoethyl]-2-[2-[4-(methylsulfonyl)phenyl]-2-oxoethyl]propanedioate (prepared above) in 20 mL of THF. The resulting mixture was stirred at ambient temperature for 16 hours, filtered through a pad of celite, rinsed with ethyl acetate, and concentrated in vacuo. The residue was partitioned between water and ethyl acetate; the organic phase was washed with brine, dried (MgSO$_4$), and concentrated in vacuo. The residue was chromatographed on silica gel to give 6.26 g (44%) of 1-[2-(4-fluorophenyl)-4,4-dicarbomethoxycyclopenten-1-yl]-4-(methylsulfonyl)benzene which was identical to the material prepared in Step 8, Method A.

Step 9: Preparation of 1-[2-(4-fluorophenyl)-4,4-di(hydroxymethyl)cyclopenten-1-yl]-4-(methylsulfonyl)benzene Under nitrogen, a solution of 1.01 g (2.34 mmol) of 1-[2-(4-fluorophenyl)-4,4-dicarbomethoxycyclopenten-1-yl]-4-(methylsulfonyl)benzene (prepared in Step 8) in 1.5 mL of THF at −78° C. was treated with 11.6 mL (11.6 mmol) of DIBAL (1.0M in THF). The reaction was stirred at ambient temperature for 1.5 hours, quenched with acetone and aqueous NaOH, extracted with ethyl acetate, dried (MgSO$_4$), and concentrated in vacuo to give 840 mg of crude 1-[2-(4-fluorophenyl)-4,4-di(hydroxymethyl)cyclopenten-1-yl]-4-(methylsulfonyl)benzene as a colorless oil: NMR (CDCl$_3$) δ2.82 (d, J=5 Hz, 4H), 3.04 (s, 3H), 3.86 (d, J=5 Hz, 4H), 6.94 (t, J=9 Hz, 2H), 7.11 (dd, J=5 and 9 Hz, 2H), 7.33 (d, J=9 Hz, 2H), 7.77 (d, J=9 Hz, 2H).

Step 10: Preparation of 1-[2-(4-fluorophenyl)-4,4-di(tosylmethyl)cyclopenten-1-yl]-4-(methylsulfonyl)benzene Under nitrogen, a solution of 2.34 mmol of the crude 1-[2-(4-fluorophenyl)-4,4-di(hydroxymethyl)cyclopenten-1-yl]-4-(methylsulfonyl)benzene (prepared in Step 9) in 8 mL of pyridine at ambient temperature was treated with 1.2 g (6.3 mmol) of p-totuenesulfonyl chloride (tosyl chloride). The resulting solution was stirred at room temperature for 17 hours, concentrated in vacuo, and chromatographed on silca gel to give 1.06 g (66% overall yield from Step 9) of 1-[2-(4-fluorophenyl)-4,4-di (tosylmethyl) cyclopenten-1-yl]-4-(methylsulfonyl)benzene as a colorless solid: NHR (CDCl$_3$) δ2.46 (s, 6H), 2.73 (s, 3H), 3.04 (s, 3H), 4.05 (s, 4H), 6.85–7.0 (m, 4H), 7.20 (d, J=8 Hz, 2H), 7.34 (d, J=8 Hz, 4H), 7.75 (d, J=8 Hz, 6H).

Step 11: Preparation of 1-[2-(4-fluorophenyl)-4,4-di(fluoromethyl)cyclopenten-1-yl]-4-(methylsulfonyl)benzene Under nitrogen, 20 mL (20 mmol) of Bu$_4$NF (1.0 M in THF) was added to a stirred solution of 3.7 g (5.4 mmol) of 1-[2-(4-fluorophenyl)-4,4-di(tosylmethyl)cyclopenten-1-yl]-4-(methylsulfonyl)benzene (prepared in Step 10) in 10 mL of anhydrous THF. The reaction was stirred at reflux for 14 hours and allowed to cool to ambient temperature. Purification by silica gel chromatography (MPLC) using hexane/ethyl acetate (9:1) gave 1.0 g (49%) of 1-[2-(4-fluorophenyl)-4,4-di(fluoromethyl)cyclopenten-1-yl]-4-(methylsulfonyl)benzene as a pale-yellow solid: mp 134°–135° C.; NMR (CDCl$_3$) δ2.84 (s, 4H), 3.04 (s, 3H), 4.52 (d, J=47 Hz, 2H), 6.95 (t, J=9 Hz, 2H), 7.06–7.13 (m, 2H), 7.32 (d, J=9 Hz, 2H),7.79 (d, J=9 Hz, 2H); HRMS. Calc'd for C$_{20}$H$_{19}$F$_3$O$_2$S: 380.1058. Found: 380.1077. Anal. Calc'd for C$_{20}$H$_{19}$F$_3$O$_2$S+0.30 H20: C, 62.26; H, 5.12; F, S, 8.31. Found: C, 62.47; H, 5.26; S, 8.47.

EXAMPLE 17

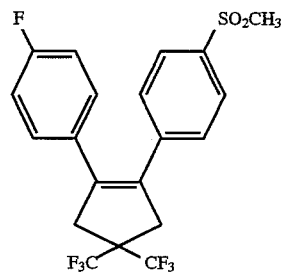

1-[2-(4-Fluorophenyl)-4,4-di(triflnoromethyl)cyclopenten-1-yl]-4-(methylsulfonyl)benzene Following the general procedures outlined in Synthetic Schemes XV, XX, XXI, and XXII, 1-[2-(4-fluorophenyl)-4,4-di(trifluoromethyl)cyclopenten-1-yl]-4-(methylsulfonyl)benzene was isolated as a colorless solid:

mp 137.7°–138.5° C.; NMR (CDCl$_3$) δ3.04 (s, 3H), 3.36 (s, 4H), 6.98 (t, J=9 Hz, 2H), 7.07–7.15 (m, 2H), 7.33 (t, J=9 Hz, 2H), 7.82 (t, J=9 Hz, 2H); MS (FAB) m/e (rel intensity) 459 (100), 374 (10); HRMS. Calc'd for C$_{20}$H$_{15}$F$_7$O$_2$S: 452.0681. Found: 452.0712. Anal. Calc'd for C$_{20}$H$_{15}$F$_7$O$_2$S+0.23 H$_2$O: C, 53.16; 3.60; F, 28.11. Found: C, 52.85; H, 3.40; N, 28.06.

EXAMPLE 18

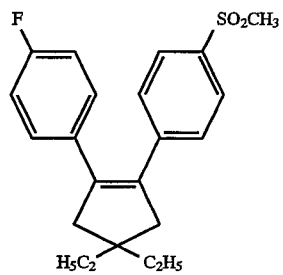

1-[2-(4-Fluorophenyl)-4,4-diethylcyclopenten-1-yl]-4-(methylsulfonyl)benzene

Following the general procedures outlined in Synthetic Schemes XV, XX, XXI, and XXII, 1-[2-(4-fluorophenyl)-4,4-diethylcyclopenten-1-yl]-4-(methylsulfonyl)benzene was isolated as a pale-yellow oil: NMR (CDCl$_3$) δ0.91 (t, J=8 Hz, 6H), 1.56 (q, J=8 Hz, 4H), 2.69 (s, 4H), 3.03 (s, 3H), 6.92 (t, J=8 Hz, 2H), 7.09 (t, J=8 Hz, 2H), 7.31 (t, J=8 Hz, 2H), 7.75 (t, J=8 Hz, 2H); MS (EI) m/e (rel intensity) 372 (100), 343 (46), 264 (18), 235 (20); HRMS. Calc'd for C$_{22}$H$_{25}$FO$_2$S: 372.1559. Found: 372.1532. Anal. Calc'd for C$_{22}$H$_{25}$FO$_2$S: C, 69.08; H, 6.88; F, 4.97; S, 8.38. Found: C, 69.05; H, 6.96; F, 4.92; S, 8.71.

EXAMPLE 19

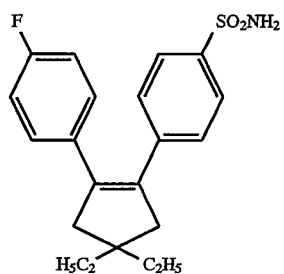

4-[2-(4-Fluorophenyl)-4,4-diethylcyclopenten-1-yl] benzenesulfonamide

Following the general procedure outlined in Synthetic Scheme XXIII, 1-[2-(4-fluorophenyl)-4,4-diethylcyclopenten-1-yl]-4-(methylsulfonyl) benzene (the title compound of Example 18) was converted to 4-[2-(4-fluorophenyl)-4,4-diethylcyclopenten-1-yl] benzenesulfonamide as a colorless solid: mp 100.8°–101.2° C.; NMR (CDCl$_3$) δ0.91 (t, J=8 Hz, 6H), 1.49–1.60 (m, 4H), 2.68 (s, 4H), 4.69–4.77 (m, 2H), 6.92 (t, J=9 Hz, 2H), 7.05–7.13 (m, 2H), 7.26 (t, J=9 Hz, 2H), 7.74 (t, J=9 Hz, 2H); MS (EI) m/e (rel intensity) 373 (100), 344 (38), 264 (12), 235 (25), 109 (63); HRMS. Calc'd for C$_{21}$H$_{24}$FNO$_2$S: 373.1512. Found: 373.1572. Anal. Calc'd for C$_{21}$H$_{24}$FNO$_2$S: C, 67.53; H, 6.48; N, 3.75. Found: C, 67.55; H, 6.43; N, 3.75.

EXAMPLE 20

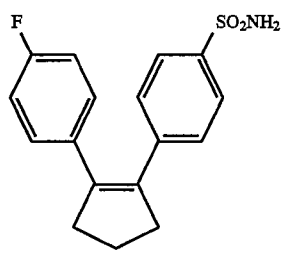

4-[2-(4-Fluorophenyl)cyclopenten-1-yl] benzenesulfonamide

Following the general procedure outlined in Synthetic Scheme XXIII, 1-[2-(4-fluorophenyl)cyclopenten-1-yl]-4-(methylsulfonyl)benzene (the title compound of Example 1) was converted to 4-[2-(4-fluorophenyl)cyclopenten-1-yl] benzenesulfonamide as a colorless solid: mp 173°–174° C.; NMR (CDCl$_3$) δ2.02–2.15 (m, 2H), 2.92 (t, J=7 Hz, 4H), 4.73 (br s, 2H), 6.93 (t, J=10 Hz, 2H), 7.06–7.15 (m, 2H), 7.28 (d, J=8 Hz, 2H), 7.75 (d, J=8 Hz, 2H); MS (EI) m/e (rel intensity) 317 (100) 237 (40), 221 (30), 109 (55); HEMS. Calc'd for C$_{17}$H$_{16}$FNO$_2$S: 317.0886. Found: 317.0916. Anal. Calc'd for C$_{17}$H$_{16}$FNO$_2$S: C, 64.28; H, 5.05; N, 4.42. Found: C, 63.98; H, 5.29; N, 4.21.

EXAMPLE 21

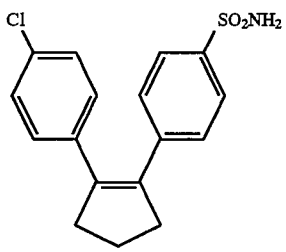

4-[2-(4-Chlorophenyl)cyclopenten-1-yl] benzenesulfonamide

Following the general procedure outlined in Synthetic Scheme XXIII, 1-[2-(4-chlorophenyl)cyclopenten-1-yl]-4-(methylsulfonyl)benzene (the title compound of Example 3) was converted to 4-[2-(4-chlorophenyl) cyclopenten-1-yl] benzenesulfonamide as a colorless solid: mp 177°–178° C.; NMR (CDCl$_3$) δ2.09 (p, J=8 Hz, 2H), 2.90 (t, J=8 Hz, 4H), 4.78 (s, 2H), 7.06 (d, J=9 Hz, 2H), 7.20 (d, J=9 Hz, 2H), 7.27 (d, J=9 Hz, 2H), 7.76 (d, J=9 Hz, 2H); MS (EI) m/e (rel intensity) 335 (57), 333 (100), 253 (24), 218 (70), 217 (47), 202 (36), 125 (29), 115 (36), 91 (24); HRMS. Calc'd for C$_{17}$H$_{16}$ClNO$_2$S: 333.0590. Found: 333.0587. Anal. Calc'd for C$_{17}$H$_{16}$ClNO$_2$S: C, 60.04; H, 4.95; Cl, 10.42; N, 4.12; S, 9.43. Found: C, 59.83; H, 4.84; Cl, 10.99; S, 10.77.

EXAMPLE 22

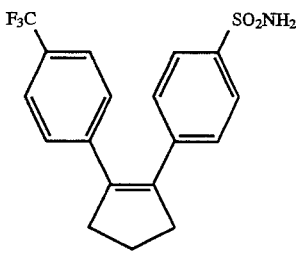

4-[2-(4-(Trifluoromethyl)phenyl) cyclopenten-1-yl] benzenesulfonamide

Following the general procedures outlined in Synthetic Scheme XXIII, 1-[2-(4-(trifluoromethyl)phenyl)cyclopenten-1-yl]-4-(methylsulfonyl)benzene (the title compound of Example 6) was converted to 4-[2-(4-(trifluoromethyl)phenyl)cyclopenten-1-yl] benzenesulfonamide as a colorless solid: mp 164°165° C. (dec); NMR C(CDCl$_3$) δ2.05–2.18 (m, 2H), 2.93 (t, J=8 Hz, 4H), 4.75 (s, 2H), 7.20–7.30 (m, 4H), 7.48 (t, J=8 Hz, 2H), 7.66 (t, J=8 Hz, 2H); MS (FAB) m/e (rel intensity) 392 (26), 374 (100), 334 (13), 308 (8); HRMS. Calc'd for C$_{18}$H$_{16}$F$_3$NO$_2$S: 367.0854. Found: 367.0832. Anal. Calc'd for C$_{18}$H$_{16}$F$_3$NO$_2$S: C, 58.85; H, 4.39; N, 3.81. Found: C, 58.75; H, 4.45; N, 3.53.

EXAMPLE 23

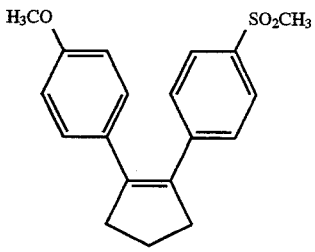

1-[2-(4-Methoxyphenyl)cyclopenten-1-yl]-4-(methylsulfonyl)benzene

Following the general procedures outlined in Synthetic Schemes I, VII, and X, 1-[2-(4-methoxyphenyl) cyclopenten-1-yl]-4-(methylsulfonyl) benzene was isolated as a colorless solid: mp 128.8°–129.8° C.; NMR (CDCl$_3$) δ2.01–2.14 (m, 2H), 2.90 (t, J=8 Hz, 4H), 3.04 (s, 3H), 3.79 (s, 3H), 6.78 (t, J=9 Hz, 2H), 7.08 (t, J=9 Hz, 2H), 7.36 (t, J=9 Hz, 2H), 7.75 (t, J=9 Hz, 2H); MS (FAB) m/e (rel intensity) 335 (100); HRMS. Calc'd for C$_{19}$H$_{20}$O$_3$S: 328.1133. Found: 328.1125. Anal. Calc'd for C$_{19}$H$_{20}$O$_3$S: C, 69.48; H, 6.14; S, 9.76. Found: C, 69.62; H, 6.19; S, 9.80.

EXAMPLE 24

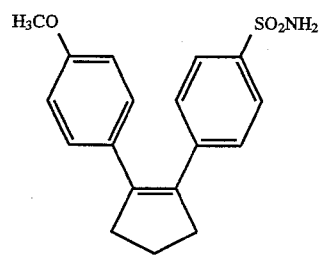

4-[9.-(4-Methoxyphenyl) cyclopenten-1-yl] benzenesulfonamide

Following the general procedure outlined in Synthetic Scheme XXIII, 1-[2-(4-methoxyphenyl) cyclopenten-1-yl]-4-(methylsulfonyl) benzene (the title compound of Example 23) was converted to 4-[2-(4-methoxyphenyl) cyclopenten-1-yl]benzenesulfonamide as a colorless solid: mp 171°–175° C. (dec); NMR (CDCl$_3$) δ 2.00–2.12 (m, 2H), 2.89 (t, J=8 Hz, 4H), 3.79 (s, 3H), 4.70–4.76 (m, 2H), 6.77 (t, J=9 Hz, 2H), 7.08 (t, J=9 Hz, 2H), 7.30 (t, J=9 Hz, 2H), 7.73 (t, J=9 Hz, 2H); MS (FAB) m/e (rel intensity) 329 (100), 297 (11), 249 (64); HRMS. Calc'd for C$_{18}$H$_{19}$NO$_3$S: 329.1086. Found: 329.1112. Anal. Calc'd for C$_{18}$H$_{19}$NO$_3$S: C, 65.63; H, 5.81; N, 4.25. Found: C, 65.46; H, 5.89; N, 4.26.

EXAMPLE 25

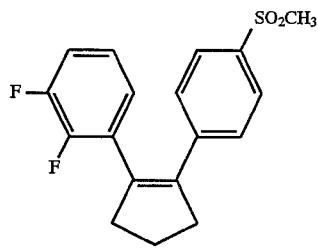

1-[2-(2,3-Difluorophenyl)cyclopenten-1-yl]-4-(methylsulfonyl)benzene

Following the general procedures outlined in Synthetic Schemes I, VII, and X, 1-[2-(2,3-difluorophenyl) cyclopenten-1-yl]-4-(methylsulfonyl) benzene was isolated as a colorless solid: mp 151°–152° C.; NMR (CDCl$_3$) δ2.14 (p, J=8 Hz, 2H), 2.87–3.00 (m, 4H), 3.02 (s, 3H), 6.77–6.84 (m, 1H), 6.91–7.11 (m, 2H), 7.28 (d, J=9 Hz, 2H), 7.74 (d, J=9 Hz, 2H); MS (EI) m/e (rel intensity) 334 (100), 255 (54), 227 (24), 128 (29), 127 (33); HRMS. Calc'd for C$_{18}$H$_{16}$F$_2$O$_2$S: 334.0839. Found: 334.0835. Anal. Calc'd for C$_{18}$H$_{16}$F$_2$O$_2$S: C, 64.66; H, 4.82; S, 9.59. Found: C, 64.67; H, 4.87; S, 9.46.

EXAMPLE 26

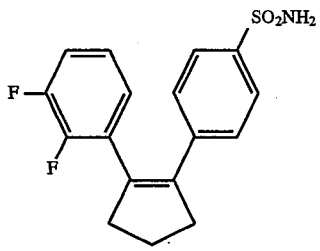

4-[2-(2,3-Difluorophenyl)cyclopenten-1-yl]
benzenesulfonamide

Following the general procedure outlined in Synthetic Scheme XXIII, 1-[2-(2,3-difluorophenyl)cyclopenten-1-yl]-4-(methylsulfonyl)benzene (the title compound of Example 25) was converted to 4-[2-(2,3-difluorophenyl)cyclopenten-1-yl]benzenesulfonamide as a colorless solid: mp 133°–134° C.; NMR (CDCl$_3$) δ2.13 (p, J=8 Hz, 2H), 2.85–3.00 (m, 4H), 4.75 (s, 2H), 6.76–6.84 (m, 1H), 6.90–7.11 (m, 2H), 7.20–7.27 (m, 2H), 7.72 (d, J=8 Hz, 2H); HRMS. Calc'd for $C_{17}H_{15}F_2NO_2S$: 335.0792. Found: 335.0774. Anal. Calc'd for $C_{17}H_{15}F_2NO_2S+0.18$ H2O: C, 60.29; H, 4.57; F, 11.22; N, 4.14; S, 9.47. Found: C, 60.27; H, 4.69; F, 11.35; N, 4.06; S, 9.52.

EXAMPLE 27

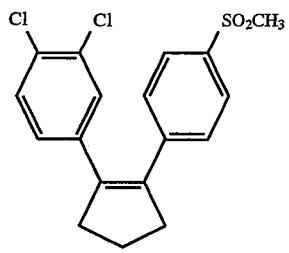

1-[2-(3,4-Dichlorophenyl)cyclopenten-1-yl]-4-(methylsulfonyl)benzene

Following the general procedures outlined in Synthetic Schemes I, VII, and X, 1-[2-(3,4-dichlorophenyl)cyclopenten-1-yl]-4-(methylsulfonyl)benzene was isolated as a colorless solid: mp 100°–101° C.; NMR (CDCl$_3$) δ2.10 (p, J=8 Hz, 2H), 2.85–2.96 (m, 4H), 3.05 (s, 3H), 6.91 (dd, J=9 and 2 Hz, 1H), 7.23–7.28 (m, 2H), 7.32 (d, J=9 Hz, 2H), 7.79 (d, J=9 Hz, 2H); HRMS. Calc'd for $C_{18}H_{16}Cl_2O_2S$: 366.0248. Found: 366.0269. Anal. Calc'd for $C_{18}H_{16}Cl_2O_2S$: C, 58.86; H, 4.39; Cl, 19.31; S, 8.73. Found: C, 58.53; H, 4.53; Cl, 19.26; S, 8.78.

EXAMPLE 28

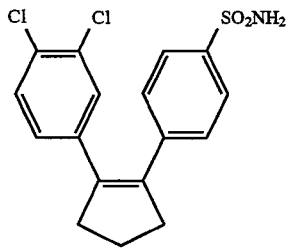

4-[2-(3,4-Dichlorophenyl)cyclopenten-1-yl]
benzenesulfonamide

Following the general procedure outlined in Synthetic Scheme XXIII, 1-[2-(3,4-dichlorophenyl)cyclopenten-1-yl]-4-(methylsulfonyl)benzene (the title compound of Example 27) was converted to 4-[2-(3,4-dichlorophenyl)cyclopenten-1-yl]benzenesulfonamide as a colorless solid: mp 134°–135° C.; NMR (CDCl$_3$) δ2.10 (p, J=8 Hz, 2H), 2.84–2.95 (m, 4H), 4.76 (s, 2H), 6.91 (dd, J=9 and 2 Hz, 1H), 7.23–7.30 (m, 4H), 7.78 (d, J=9 Hz, 2H); MS (FAB) m/e 372, 370, 368. Anal. Calc'd for $C_{17}H_{15}Cl_2NO_2S$: C, 55.43; H, 4.11; Cl, 19.25; N, 3.80; S, 8.71. Found: C, 55.57; H, 4.02; Cl, 19.24; N, 3.67; S, 8.62.

EXAMPLE 29

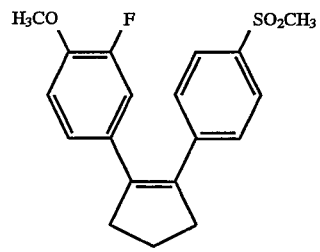

1-[2-(3-Fluoro-4-methoxyphenyl)cyclopenten-1-yl]-4-(methylsulfonyl)benzene

Following the general procedures outlined in Synthetic Schemes I, VII, and X, 1-[2-(3-fluoro-4-methoxyphenyl)cyclopenten-1-yl]-4-(methylsulfonyl)benzene was isolated as a colorless solid: mp 127.8°–128.6° C.; NMR (CDCl$_3$) δ2.02–2.14 (m, 2H), 2.84–2.94 (m, 4H), 3.05 (s, 3H), 3.86 (s, 3H), 6.76–6.92 (m 3H), 7.34 (t, J=9 Hz, 2H), 7.78 (t, J=9 Hz, 2H); MS (EI) m/e (rel intensity) 346 (100), 315 (7), 267 (10), 191 (10), 139 (12), 107 (7); HRMS. Calc'd for $C_{19}H_{19}FO_3S$: 346.1039. Found: 346.1049. Anal. Calc'd for $C_{19}H_{19}FO_3S$: C, 65.88; H, 5.53; F, 5.48. Found: C, 65.71; H, 5.49; F, 5.13.

EXAMPLE 30

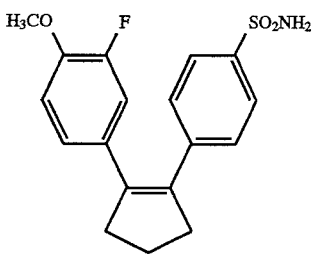

4-[2-(3-Fluoro-4-methoxyphenyl)cyclopenten-1-yl]
benzenesulfonamide

Following the general procedure outlined in Synthetic Scheme XXIII, 1-[2-(3-fluoro-4-methoxyphenyl) cyclopenten-1-yl]-4-(methylsulfonyl)benzene (the title compound of Example 29) was converted to 4-[2-(3-fluoro-4-methoxyphenyl)cyclopenten-1-yl]benzenesulfonamide as a colorless solid: mp 170.0°–170.8° C.; NMR (CDCl$_3$) δ2.01–2.13 (m, 2H), 2.83–2.93 (m, 4H), 3.87 (s, 3H), 4.75 (s, 2H), 6.76–6.92 (m, 3H), 7.30 (t, J=9 Hz, 2H), 7.76 (t, J=2H); MS (EI) m/e (rel intensity) 347 (100), 316 (12), 267 (12), 252 (19), 236 (20), 191 (16), 139 (12); HRMS. Calc'd for C$_{18}$H$_{18}$FNO$_3$S: 347.0991. Found: 347.0955. Anal. Calc'd for C$_{18}$H18FNO$_3$S: C, 62.23; H, 5.22; N, 4.03. Found: 62.37; H, 5.36; 3.99.

EXAMPLE 32

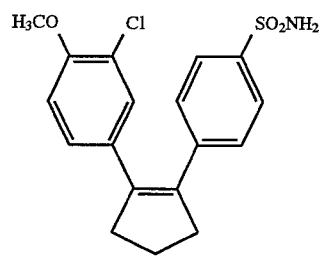

4-[2-(3-Chloro-4-methoxyphenyl)cyclopenten-1-yl]
benzenesulfonamide

Following the general procedure outlined in Synthetic Scheme XXIII, 1-[2-(3-chloro-4-methoxyphenyl) cyclopenten-1-yl]-4-(methylsulfonyl)benzene (the title compound of Example 31) was converted to 4-[2-(3-chloro-4-methoxyphenyl)cyclopenten-1-yl]benzenesulfonamide as a colorless solid: mp 178.8°–180.0° C.; NMR (CDCl$_3$) δ2.01–2.13 (m, 2H), 2.83–2.93 (m, 4H), 3.87 (s, 3H), 4.75 (s, 2H), 6.76 (d, J=9 Hz, 1H), 6.94 (dd, J=9 and 2 Hz, 1H), 7.20 (d, J=2 Hz, 1H), 7.30 (t, J=8 Hz, 2H), 7.76 (t, J=8 Hz, 2H); MS (EI) m/e (rel intensity) 363 (100), 328 (14), 268 (16), 233 (17); HRMS. Calc'd for C$_{18}$H$_{18}$ClNO$_3$S: 363.0696. Found: 363.0701. Anal. Calc'd for C$_{18}$H$_{18}$ClNO$_3$S: C, 59.41; H, 5.00; N, 3.85. Found: C, 59.12; H, 5.06; N, 3.69.

EXAMPLE 31

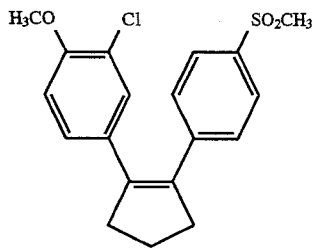

1-[2-(3-Chloro-4-methoxyphenyl)cyclopenten-1-yl]-
4-(methylsulfonyl)benzene

Following the general procedures outlined in Synthetic Schemes I, VII, and X, 1-[2-(3-chloro-4-methoxyphenyl) cyclopenten-1-yl]-4-(methylsulfonyl)benzene was isolated as a colorless solid: mp 118°–120° C.; NMR (CDCl$_3$) δ2.01–2.14 (m, 2H), 2.83–2.95 (m, 4H), 3.04 (s, 3H), 3.87 (s, 3H), 6.77 (d, J=9 Hz, 1H), 6.94 (d, J=9 Hz, 1H), 7.18 (d, J=2 Hz, 1H), 7.34 (t, J=9 Hz, 2H), 7.77 (t, J=9 Hz, 2H); MS (EI) m/e (rel intensity) 362 (100), 327 (13), 248 (18), 233 (8); HRMS. Calc'd for C$_{19}$H$_{19}$ClO$_3$S: 362.0743. Found: 362.0727. Anal. Calc'd for C$_{19}$H$_{19}$ClO$_3$S: C, 62.89; H, 5.28; Cl, 9.77. Found: C, 62.89; H, 5.42; 9.95.

EXAMPLE 33

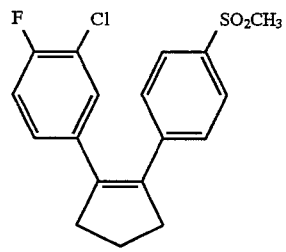

1-[2-(3-Chloro-4-fluorophenyl)cyclopenten-1-yl]-4-
(methylsulfonyl)benzene

Following the general procedures outlined in Synthetic Schemes I, VII, and X, 1-[2-(3-chloro-4-fluorophenyl) cyclopenten-1-yl]-4-(methylsulfonyl)benzene was isolated as a colorless solid: mp 87.5°–88.5° C.; NMR (CDCl$_3$) δ2.03–2.15 (m, 2H), 2.84–2.95 (m, 4H), 3.04 (s, 3H), 3.87 (s, 3H), 6.91–7.02 (m, 2H), 7.19 (dd, J=8 and 2 Hz, 1H), 7.31 (t, J=9 Hz, 2H), 7.79 (t, J=9 Hz, 2H);MS (EI) m/e (rel intensity) 350 (100), 315 (6), 271 (22), 236 (69); HRMS. Calc'd for C$_{18}$H$_{16}$ClFO$_2$S: 350.0544. Found: 350.0523. Anal. Calc'd for C$_{18}$H$_{16}$ClFO$_2$S: C, 61.62; H, 4.60; F, 5.42. Found: C, 61.37; H, 4.67; F, 5.09.

EXAMPLE 34

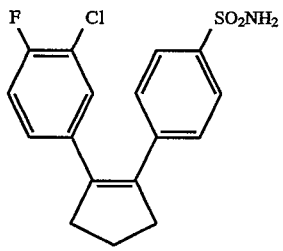

4-[2-(3-Chloro-4-fluorophenyl)cyclopenten-1-yl]benzenesulfonamide

Following the general procedure outlined in Synthetic Scheme XXIII, 1-[2-(3-chloro-4-fluorophenyl)cyclopenten-1-yl]-4-(methylsulfonyl)benzene (the title compound of Example 33) was converted to 4-[2-(3-chloro-4-fluorophenyl)cyclopenten-1-yl]benzenesulfonamide as a colorless solid: mp 150.5°–151.5° C.; NMR (CDCl$_3$) δ2.02–2.16 m, 2H), 2.83–2.96 (m, 4H), 4.78 (s, 2H), 6.90–7.03 (m, 2H), 7.18–7.24 (m, 1H), 7.28 (t, J=9 Hz, 2H), 7.78 (t, J=9 Hz, 2H); MS (EI) m/e (rel intensity) 351 (100), 316 (16), 271 (40), 236 (28); HRMS. Calc'd for C$_{17}$H$_{15}$ClFNO$_2$S: 351.0496. Found: 351.0516. Anal. Calc'd for C$_{17}$H$_{15}$ClFNO$_2$S: C, 58.04; H, 4.30; N, 3.98. Found: C, 57.94; H, 4.41; N, 3.93.

EXAMPLE 35

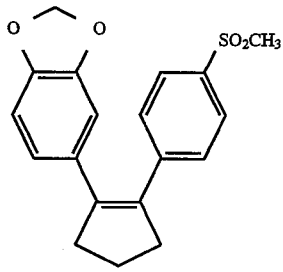

5-[2-[4-(Methylsulfonyl)phenyl]cyclopenten-1-yl]-1,3-benzodioxole

Following the general procedures outlined in Synthetic Schemes I, VII, and X, 5-[2-[4-(methylsulfonyl)phenyl]cyclopenten-1-yl]-1,3-benzodioxole was isolated as a colorless solid: mp 140.0°–140.7° C.; NMR (CDCl$_3$) δ2.06 (p, J=8 Hz, 2H), 2.82–2.93 (m, 4H), 3.04 (s, 3H), 5.93 (s, 2H), 6.59–6.72 (m, 3H), 7.35 (d, J=9 Hz, 2H), 7.76 (d, J=9 Hz, 2H); HRMS. Calc'd for C$_{19}$H$_{18}$O$_4$S: 342.0926. Found: 342.0932. Anal. Calc'd for C$_{19}$H$_{18}$O$_4$S: C, 66.65; H, 5.30. Found: C, 66.43; H, 5.47.

EXAMPLE 36

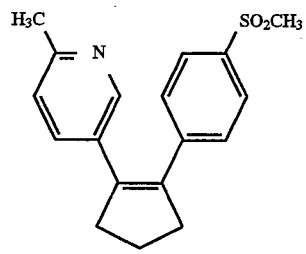

4-[2-(2-Methylpyridin-5-yl)cyclopenten-1-yl]benzenesulfonamide

Following the general procedure outlined in Synthetic Scheme XI (with the substitution of 33 for 43), 1-(2-bromocyclopenten-1-yl)-4-(methylsulfonyl)benzene (prepared in Step 1 of Example 11) was reacted with 2-methylpyridin-5-yltrimethyltin (prepared in Synthetic Scheme VIII) to provide 4-[2-(2-methylpyridin-5-yl)cyclopenten-1-yl]benzenesulfonamide as a colorless solid: mp 108.0°–109.5° C.; NMR (CDCl$_3$) δ2.05–2.19 (m, 2H), 2.46 (s, 3H), 2.86 (t, J=7 Hz, 4H), 3.05 (s, 3H), 7.02 (d, J=8 Hz, 1H), 7.32 (br s, 1H), 7.33 (d, J=8 Hz, 2H), 7.78 (d, J=8 Hz, 2H), 8.82 (d, J=2Hz, 1H); MS (CI) m/e (rel intensity) 314 (100), 234 (5), 89 (20); HRMS. Calc'd for C$_{18}$H$_{19}$LiNO$_2$S: 320.1297. Found: 320.1281. Anal. Calc'd for C$_{18}$H$_{19}$NO$_2$S: C, 69.01; H, 6.07; N, 4.47. Found: C, 68.91; H, 6.40; 4.28.

EXAMPLE 37

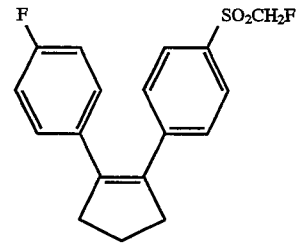

1-[2-(4-Fluorophenyl)cyclopenten-1-yl]-4-(fluoromethylsulfonyl)benzene

Under nitrogen, 2.7 mL (3.8 mmol) of methyllithium (1.4M in ether) was added to a stirred solution of 1.0 g (3.2 mmol) of 1-[2-(4-fluorophenyl)cyclopenten-1-yl]-4-(methylsulfonyl)benzene (the title compound of Example 1) in 10 mL of anhydrous THF at −78° C. The reaction was allowed to warm to ambient temperature and stir for 1 hour. A solution of 1.2 g (4.8 mmol) of N-fluorodibenzenesulfonamide (Aldrich) in 5 mL of anhydrous THF was slowly added at 0° C. The reaction was stirred for 1 hour at ambient temperature and quenched with water. Purification by silica gel chromatography (MPLC) using hexane/ethyl acetate (9:1) gave 110 mg (10%) of 1-[2-(4-fluorophenyl)cyclopenten-1-yl]-4-(fluoromethylsulfonyl)benzene as a colorless solid: mp 123°–124° C.; NMR (CDCl$_3$) δ2.10 (p, J=7 Hz, 2H), 2.92 (t, J=7 Hz, 4H), 5.11 (d, J=47 Hz, 2H), 6.94 (dd, J=9 and 2 Hz, 2H), 7.07–7.14 (m, 2H), 7.3 6 (d, J=9 Hz, 2H), 7.77 (d, J=9 Hz, 2H); MS (EI) m/e (rel intensity) 334 (100), 237 (24), 209 (22); HIMS. Calc'd for C$_{18}$H$_{16}$F$_2$O$_2$S: 334.0839. Found: 334.0828. Anal. Calc'd for C$_{18}$H$_{16}$F$_2$O$_2$S+0.22 H$_2$O: C, 63.90; H, 4.90; F, 11.23; S, 9.48. Found: C, 63.89; H, 4.90; F, 11.07; 9.76.

EXAMPLE 38

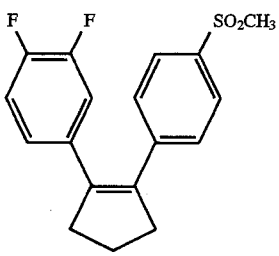

1-[2-(3,4-Difluorophenyl)cyclopenten-1-yl]-4-(methylsulfonyl)benzene

Following the general procedures outlined in Synthetic Schemes I, VII, and X, 1-[2-(3,4-difluorophenyl)cyclopenten-1-yl]-4-(methylsulfonyl)benzene was isolated as a colorless solid: mp 114°–115 °C.; NMR (CDCl$_3$) δ2.10 (p, J=8 Hz, 2H), 2.85–2.96 (m, 4H), 3.05 (s, 3H), 6.79–6.86 (m, 1H), 6.89–7.07 (m, 2H), 7.32 (d, J=9 Hz, 2H), 7.79 (d, J=9 Hz, 2H); MS (FAB) m/e 341 (M+Li); HRMS. Calc'd for C$_{18}$H$_{17}$F$_2$O$_2$S: 335.0917. Found: 335.0925. Anal. Calc'd for C$_{18}$H$_{16}$F$_2$O$_2$S: C, 64.66; H, 4.82; F, 11.36. Found: C, 64.77; H, 4.91; F, 11.39.

EXAMPLE 39

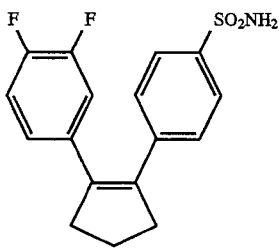

4-[2-(3,4-Difluorophenyl)cyclopenten-1-yl]benzenesulfonamide

Following the general procedure outlined in Synthetic Scheme XXIII, 1-[2-(3,4-difluorophenyl)cyclopenten-1-yl]-4-(methylsulfonyl)benzene (the title compound of Example 38) was converted to 4-[2-(3,4-difluorophenyl)cyclopenten-1-yl]benzenesulfonamide as a colorless solid: mp 147–147.5° C.; NMR (CDCl$_3$) δ2.10 (p, J=9 Hz, 2H), 2.84–2.95 (m, 4H), 4.76 (s, 2H), 6.80–6.86 (m, 1H), 6.90–7.07 (m, 2H), 7.27 (d, J=9 Hz, 2H), 7.78 (d, J=9 Hz, 2H); MS (FAB) m/e 342 (M+Li); HRMS. Calc'd for C$_{17}$H$_{16}$F$_2$NO$_2$S: 336.0870. Found: 336.0856. Anal. Calc'd for C$_{17}$H$_{15}$F$_2$NO$_2$S: C, 60.88; H, 4.51; N, 4.18. Found: C, 60.97; H, 4.56; N, 4.15.

BIOLOGICAL EVALUATION

Rat Carrageenan Foot Pad Edema Test

The carrageenan foot edema test was performed with materials, reagents and procedures essentially as described by Winter, et al., (Proc. Soc. Exp. Biol. Med., 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, Laboratory Models for Testing NSAIDs, in Non-steroidal Anti-Inflammatory Drugs, (J. Lombardino, ed. 1985)). Results are shown in Table I.

Rat Carrageenan-induced Analgesia Test

The analgesia test using rat carrageenan was performed with materials, reagents and procedures essentially as described by Hargreaves, et al., (Pain, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

| Examples | RAT PAW EDEMA % Inhibition @ 10 mg/kg body weight | ANALGESIA % Inhibition @ 20 mg/kg body weight |
|---|---|---|
| 1 | 32 | 66 |
| 2 | 39 | |
| 3 | 33 | 41 |
| 4 | 25 | |
| 5 | 16 | |
| 6 | 39 | 29 |
| 11 | 28 | 39 |
| 12 | 45[1] | |
| 13 | 34[2] | 14[2] |
| 14 | 31[2] | |
| 15 | 41[2] | |
| 20 | 26 | 44[2] |
| 21 | 49[2] | |
| 23 | 22 | 15[2] |
| 25 | 32[2] | |
| 28 | 10 | 26[2] |
| 30 | 47[2] | |
| 31 | 28[2] | |
| 32 | 13 | 17[2] |
| 34 | 37 | 46[2] |
| 35 | 6[2] | |
| 36 | 33[2] | |

[1]Assay performed at 20 mg/kg body weight.
[2]Assay performed at 30 mg/kg body weight.

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of recombinant COX baculoviruses

A 2.0 kb fragment containing the coding region of either human or murine COX-I or human or murine COX-II was cloned into a BamHI site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2x10e8) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7-10E8 pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000xG for 30 minutes, and the resultant supernatant was stored at $-80°$ C. before being assayed for COX activity.

b. Assay for COX I and COX II activity

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at $37°$ C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

TABLE II

| Examples | HUMAN COX I $ID_{50}$ µM | HUMAN COX II $ID_{50}$ µM |
| --- | --- | --- |
| 1 | >100 | <.1 |
| 2 | >100 | <.1 |
| 3 | >100 | <.1 |
| 4 | >100 | <.1 |
| 5 | >100 | <.1 |
| 6 | >100 | .9 |
| 7 | >100 | 2.2 |
| 8 | >100 | 77.9 |
| 9 | >100 | 3.2 |
| 10 | >100 | 6.6 |
| 11 | >100 | .2 |
| 12 | 18.3 | <.1 |
| 13 | .5 | <.1 |
| 14 | 1.6 | <.1 |
| 15 | <.1 | <.1 |
| 16 | .58 | <.1 |
| 17 | >100 | <.1 |
| 18 | >100 | 65 |
| 19 | 10 | 3.9 |
| 20 | 4.2 | <.1 |
| 21 | 1.3 | <.1 |
| 22 | 4.0 | .1 |
| 23 | 9.9 | <.1 |
| 24 | .2 | <.1 |
| 25 | >100 | <.1 |
| 26 | 3.6 | <.1 |
| 27 | >100 | <.1 |
| 28 | 3.7 | <.1 |

TABLE II-continued

| Examples | HUMAN COX I $ID_{50}$ µM | HUMAN COX II $ID_{50}$ µM |
| --- | --- | --- |
| 29 | >100 | .1 |
| 30 | 8.1 | <.1 |
| 31 | >100 | .1 |
| 32 | 21.3 | <.1 |
| 33 | >100 | <.1 |
| 34 | 2.1 | <.1 |
| 35 | >100 | <.1 |
| 36 | >100 | .8 |
| 37 | >100 | <.1 |
| 38 | >100 | 1.0 |
| 39 | 9.9 | <.1 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 1000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably from about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A method of treating inflammation or an inflammation-associated disorder in a subject, said method comprising administering to the subject having such inflammation or inflammation-associated disorder, a therapeutically-effective amount of a compound of Formula I

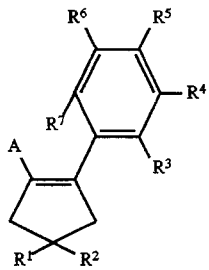

wherein A is selected from

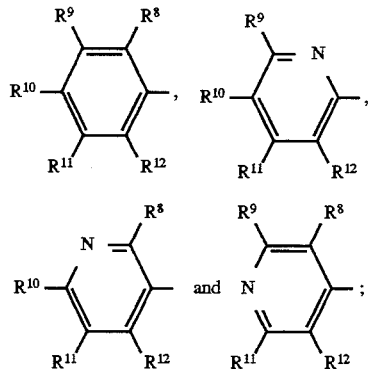

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkytsulfonyl and sulfamyl; or a pharmaceutically-acceptable salt thereof.

2. A method of treating inflammation or an inflammation-associated disorder in a subject, said method comprising administering to the subject having such inflammation or inflammation-associated disorder, a therapeutically-effective amount of a compound of Formula II

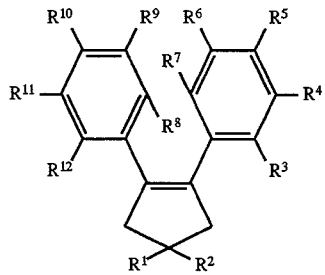

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl; or a pharmaceutically-acceptable salt thereof.

3. The method of of claim 2 wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl; or a pharmaceutically suitable salt thereof;

or a pharmaceutically-acceptable salt or prodrug thereof.

4. The method of claim 3 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, fluoromethylsulfonyl, trifluoromethylsulfonyl and sulfamyl; or a pharmaceutically suitable salt thereof.

5. The method of claim 4 wherein said compound is 4-[2-(3-chloro-4-fluorophenyl)cyclopenten-1-yl] benzenesulfonamide; or a pharmaceutically-acceptable salt thereof.

6. The method of claim 4 wherein said compound is 1-[2-(3-chloro-4-fluorophenyl)cyclopenten-1-yl]-4-(methylsulfonyl)benzene, or a pharmaceutically-acceptable salt thereof.

7. The method of claim 2 for use in treatment of inflammation.

8. The method of claim 2 for use in treatment of an inflammation-associated disorder.

9. The method of claim 8 wherein the inflammation-associated disorder is arthritis.

10. The method of claim 8 wherein the inflammation-associated disorder is pain.

11. The method of claim 8 wherein the inflammation-associated disorder is fever.

12. The method of claim 4 wherein compounds, and their pharmaceutically-acceptable salts, of the group consisting of 1-[2-(2,3-difluorophenyl)cyclopenten-1-yl]-4-(methylsulfonyl)benzene;
4-[2-(2,3-difluorophenyl)cyclopenten-1-yl]benzenesulfonamide;
1-[2-(4-chlorophenyl)-4,4-dimethylcyclopenten-1-yl]-4-(methylsulfonyl)benzene;
1-[2-(4-fluorophenyl)-4,4-diethylcyclopenten-1-yl]-4-(methylsulfonyl)benzene;
4-[2-(4-fluorophenyl)-4,4-diethylcyclopenten-1-yl]benzenesulfonamide;
4-[2-(4-methoxyphenyl)cyclopenten-1-yl]benzenesulfonamide;
4-[2-(4-chlorophenyl)-4,4-dimethylcyclopenten-1-yl]benzenesulfonamide;
1-[2-(4-fluorophenyl)cyclopenten-1-yl]-4-(fluoromethylsulfonyl)benzene;
1-[2-(4-fluoro-2-methylphenyl)cyclopenten-1-yl]-4-(fluoromethylsulfonyl)benzene;
5-[2-(4-(methylsulfonyl)phenyl]cyclopenten-1-yl]-1,3-benzodioxole;
1-[2-(4-fluorophenyl)-4,4-di(fluoromethyl)cyclopenten-1-yl]-4-(methylsulfonyl)benzene;
1-[2-(4-fluorophenyl)-4,4-di(trifluoromethyl)cyclopenten-1-yl]-4-(methylsulfonyl)benzene;
4-[2-(4-trifluoromethylphenyl)-4-carboxycyclopenten-1-yl]benzenesulfonamide;
1-[2-(3,4-dimethylphenyl)cyclopenten-1-yl]-4-(methylsulfonyl)benzene;
1-[2-(3-fluoro-4-methylphenyl)cyclopenten-1-yl]-4-(methylsulfonyl)benzene;
1-[2-(3-chloro-4-methylphenyl)cyclopenten-1-yl](methylsulfonyl)benzene;
1-[2-(3-trifluoromethyl-4-methylphenyl)cyclopenten-1-yl]-4-(methylsulfonyl)benzene;
1-[2-(3-methoxy-4-methylphenyl)cyclopenten-1-yl]-4-(methylsulfonyl)benzene;
1-[2-(3,4-difluorophenyl)cyclopenten-1-yl]-4-(methylsulfonyl)benzene;
1-[2-(3-methyl-4-fluorophenyl)cyclopenten-1-yl]-4-(methylsulfonyl)benzene;
1-[2-(3-chloro-4-fluorophenyl)cyclopenten-1-yl](methylsulfonyl)benzene;
1-[2-(3-trifluoromethyl-4-fluorophenyl)cyclopenten-1-yl]-4-(methylsulfonyl)benzene;
1-[2-(3-methoxy-4-fluorophenyl)cyclopenten-1-yl]-4-(methylsulfonyl)benzene;
1-[2-(3,4-dichlorophenyl)cyclopenten-1-yl]-4-(methylsulfonyl)benzene;
1-[2-(3-methyl-4-chlorophenyl)cyclopenten-1-yl](methylsulfonyl)benzene;
1-[2-(3-fluoro-4-chlorophenyl)cyclopenten-1-yl]-4-(methylsulfonyl)benzene;
1-[2-(3-trifluoromethyl-4-chlorophenyl)cyclopenten-1-yl]-4-(methylsulfonyl)benzene;
1-[2-(3-methoxy-4-chlorophenyl)cyclopenten-1-yl]-4-(methylsulfonyl)benzene;
1-[2-(3,4-methoxyphenyl)cyclopenten-1-yl]-4-(methylsulfonyl)benzene;
1-[2-(3-methyl-4-methoxyphenyl)cyclopenten-1-yl]-4-(methylsulfonyl)benzene;
1-[2-(3-fluoro-4-methoxyphenyl)cyclopenten-1-yl]-4-(methylsulfonyl)benzene;
1-[2-(3-trifluoromethyl-4-methoxyphenyl)cyclopenten-1-yl]-4-(methylsulfonyl)benzene;
1-[2-(3-chloro-4-methoxyphenyl)cyclopenten-1-yl]-4-(methylsulfonyl)benzene;
1-[2-[3,4-di(trifluoromethyl)phenyl]cyclopenten-1-yl]-4-(methylsulfonyl)benzene;
1-[2-(3-methyl-4-trifluoromethylphenyl)cyclopenten-1-yl]-4-(methylsulfonyl)benzene;
1-[2-(3-fluoro-4-trifluoromethylphenyl)cyclopenten-1-yl]-4-(methylsulfonyl)benzene;
1-[2-(3-methoxy-4-trifluoromethylphenyl)cyclopenten-1-yl]-4-(methylsulfonyl)benzene;
1-[2-(3-chloro-4-trifluoromethylphenyl)cyclopenten-1-yl]-4-(methylsulfonyl)benzene;
1-[2-(3-difluoromethyl-4-methylphenyl)cyclopenten-1-yl]-4-(methylsulfonyl)benzene;
1-[2-(3-difluoromethyl-4-fluorophenyl)cyclopenten-1-yl]-4-(methylsulfonyl)benzene;
1-[2-(3-difluoromethyl-4-chlorophenyl)cyclopenten-1-yl]-4-(methylsulfonyl)benzene;
1-[2-(3-difluoromethyl-4-methoxyphenyl)cyclopenten-1-yl]-4-(methylsulfonyl)benzene;
1-[2-[3,4-di(difluoromethyl)phenyl]cyclopenten-1-yl]-4-(methylsulfonyl)benzene;
1-[2-(3-methyl-4-difluoromethylphenyl)cyclopenten-1-yl]-4-(methylsulfonyl)benzene;
1-[2-(3-fluoro-4-difluoromethylphenyl)cyclopenten-1-yl]-4-(methylsulfonyl)benzene;
1-[2-(3-methoxy-4-difluoromethylphenyl)cyclopenten-1-yl]-4-(methylsulfonyl)benzene;
1-[2-(3-chloro-4-difluoromethylphenyl)cyclopenten-1-yl]-4-(methylsulfonyl)benzene;
4-[2-(4-methylthiophenyl)cyclopenten-1-yl]benzenesulfonamide;
4-[2-(4-cyanophenyl)cyclopenten-1-yl]benzenesulfonamide;
4-[2-(4-hydroxymethylphenyl)cyclopenten-1-yl]benzenesulfonamide;
4-[2-(4-methoxymethylphenyl)cyclopenten-1-yl]benzenesulfonamide;
4-[2-(4-fluoro-2-methylphenyl)cyclopenten-1-yl]benzenesulfonamide;
4-[2-(4-fluorophenyl)-4,4-di(fluoromethyl)cyclopenten-1-yl]benzenesulfonamide;
4-[2-(4-fluorophenyl)-4,4-di(trifluoromethyl)cyclopenten-1-yl]benzenesulfonamide;
5-[2-(4-(aminosulfonyl)phenyl]cyclopenten-1-yl]-1,3-benzodioxole;
4-[2-(3,4-dimethylphenyl)cyclopenten-1-yl]benzenesulfonamide;
4-[2-(3-fluoro-4-methylphenyl)cyclopenten-1-yl]benzenesulfonamide;
4-[2-(3-chloro-4-methylphenyl)cyclopenten-1-yl]benzenesulfonamide;
4-[2-(3-trifluoromethyl-4-methylphenyl)cyclopenten-1-yl]benzenesulfonamide;
4-[2-(3-methoxy-4-methylphenyl)cyclopenten-1-yl]benzenesulfonamide;
4-[2-phenylcyclopenten-1-yl]benzenesulfonamide;
4-[2-(3,4-difluorophenyl)cyclopenten-1-yl]benzenesulfonamide;
4-[2-(3-methyl-4-fluorophenyl)cyclopenten-1-yl]benzenesulfonamide;

4-[2-(3-chloro-4-fluorophenyl)cyclopenten-1-yl]
benzenesulfonamide;
4-[2-(3-trifluoromethyl-4-fluorophenyl)cyclopenten-1-yl]
benzenesulfonamide;
4-[2-(3-methoxy-4-fluorophenyl)cyclopenten-1-yl]
benzenesulfonamide;
4-[2-(3,4-dichlorophenyl)cyclopenten-1-yl]
benzenesulfonamide;
4-[2-(3-methyl-4-chlorophenyl)cyclopenten-1-yl]
benzenesulfonamide;
4-[2-(3-fluoro-4-chlorophenyl)cyclopenten-1-yl]
benzenesulfonamide;
4-[2-(3-trifluoromethyl-4-chlorophenyl)cyclopenten-1-yl]
benzenesulfonamide;
4-[2-(3-methoxy-4-chlorophenyl)cyclopenten-1-yl]
benzenesulfonamide;
4-[2-(3,4-methoxyphenyl)cyclopenten-1-yl]
benzenesulfonamide;
4-[2-(3-methyl-4-methoxyphenyl)cyclopenten-1-yl]
benzenesulfonamide;
4-[2-(3-fluoro-4-methoxyphenyl)cyclopenten-1-yl]
benzenesulfonamide;
4-[2-(3-trifluoromethyl-4-methoxyphenyl)cyclopenten-1-yl]benzenesulfonamide;
4-[2-(3-chloro-4-methoxyphenyl)cyclopenten-1-yl]
benzenesulfonamide;
4-[2-[3,4-di(trifluoromethyl)phenyl]cyclopenten-1-yl]
benzenesulfonamide;
4-[2-(3-methyl-4-trifluoromethylphenyl)cyclopenten-1-yl]
benzenesulfonamide;
4-[2-(3-fluoro-4-trifluoromethylphenyl)cyclopenten-1-yl]
benzenesulfonamide;
4-[2-(3-methoxy-4-trifluoromethylphenyl)cyclopenten-1-yl]benzenesulfonamide;
4-[2-(3-chloro-4-trifluoromethylphenyl)cyclopenten-1-yl]
benzenesulfonamide;
4-[2-(3-difluoromethyl-4-methylphenyl)cyclopenten-1-yl]
benzenesulfonamide;
4-[2-(3-difluoromethyl-4-fluorophenyl)cyclopenten-1-yl]
benzenesulfonamide;
4-[2-(3-difluoromethyl-4-chlorophenyl)cyclopenten-1-yl]
benzenesulfonamide;
4-[2-(3-difluoromethyl-4-methoxyphenyl)cyclopenten-1-yl]
benzenesulfonamide;
4-[2-[3,4-di(difluoromethyl)phenyl]cyclopenten-1-yl]
benzenesulfonamide;
4-[2-(3-methyl-4-difluoromethylphenyl)cyclopenten-1-yl]
benzenesulfonamide;
4-[2-(3-fluoro-4-difluoromethylphenyl)cyclopenten-1-yl]
benzenesulfonamide;
4-[2-(3-methoxy-4-difluoromethylphenyl)cyclopenten-1-yl]
benzenesulfonamide; and
4-[2-(3-chloro-4-difluoromethylphenyl)cyclopenten-1-yl]
benzenesulfonamide.

13. A compound of Formula I

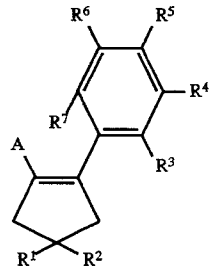

I wherein A is selected from

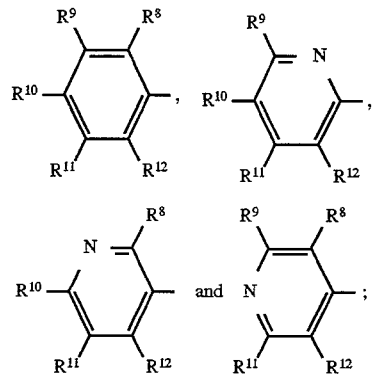

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl;

provided that when A is

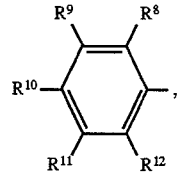

$R^5$ cannot be hydrido when $R^{10}$ is selected from hydrido, cyano, halo, methyl, trifluoromethyl and methoxy; further provided that $R^{10}$ cannot be hydrido when $R^5$ is selected from cyano, halo, methyl, trifluoromethyl and methoxy; and further provided that $R^5$ and $R^{10}$ are not both methoxy; or a pharmaceutically suitable salt thereof.

14. Compound of claim 13 wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl; or a pharmaceutically suitable salt thereof.

15. Compound of claim 14 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, fluoromethylsulfonyl, trifluoromethylsulfonyl and sulfamyl; or a pharmaceutically suitable salt thereof.

16. A compound of Formula III

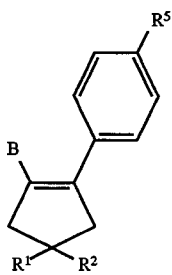

wherein each of $R^1$ and $R^2$ is independently selected from alkyl, hydrido, hydroxyalkyl, halo, haloalkyl, alkoxycarbonyl and carboxyl;

wherein $R^5$ is selected from alkylsulfonyl, haloalkylsulfonyl and sulfamyl; and wherein B is phenyl or pyridyl, wherein B is optionally substituted at a substitutable position with alkyl, halo, alkylthio, cyano, haloalkyl, alkoxy, hydroxyalkyl and alkoxyalkyl; or a pharmaceutically-acceptable salt thereof.

17. The compound of claim 16 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; wherein $R^5$ is selected from methylsulfonyl, fluoromethylsulfonyl, and sulfamyl; and wherein B is optionally substituted with a radical selected from fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl and pentoxymethyl; or a pharmaceutically-acceptable salt thereof.

18. A pharmaceutical composition comprising a therapeutically-effective amount of a compound, said compound selected from a compound of Formula I

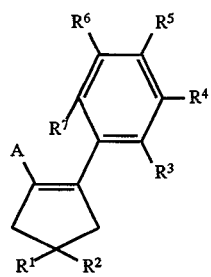

wherein A is selected from

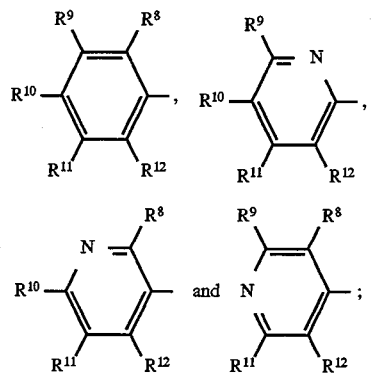

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl; or a pharmaceutically-acceptable salt thereof.

19. A compound of Formula IV

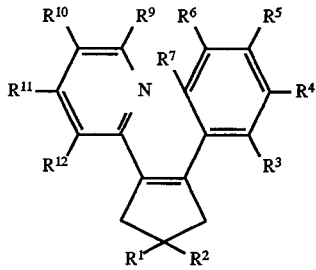

wherein each of $R^1$ and $R^2$ is independently selected from alkyl, hydrido, hydroxyalkyl, halo, haloalkyl, alkoxycarbonyl and carboxyl; and wherein each of $R^3$ through $R^7$ and $R^9$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl;

or a pharmaceutically-acceptable salt thereof.

20. The compound of claim 19 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^7$ and $R^9$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, fluoromethylsulfonyl, trifluoromethylsulfonyl and sulfamyl; or a pharmaceutically suitable salt thereof.

21. A compound of Formula V

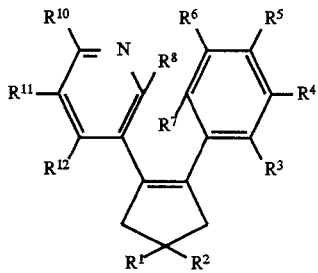

wherein each of $R^1$ and $R^2$ is independently selected from alkyl, hydrido, hydroxyalkyl, halo, haloalkyl, alkoxycarbonyl and carboxyl; and wherein each of $R^3$ through $R^7$, $R^8$, $R^{10}$, $R^{11}$ and $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl;

or a pharmaceutically-acceptable salt thereof.

22. The compound of claim 21 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^8$ and $R^{10}$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, fluoromethylsulfonyl, trifluoromethylsulfonyl and sulfamyl; or a pharmaceutically suitable salt thereof.

23. Compound of claim 22 selected from compounds, and their pharmaceutically-acceptable salts, of the group consisting of 1-[2-(2,3-dimethylpyridin-5-yl)cyclopenten-1-yl]-4-(methylsulfonyl)benzene;

1-[2-(3-fluoro-2-methylpyridin-5-yl)cyclopenten-1-yl]-4-(methylsulfonyl)benzene;

1-[2-(3-chloro-2-methylpyridin-5-yl)cyclopenten-1-yl] (methylsulfonyl)benzene;

1-[2-(3-trifluoromethyl-2-methylpyridin-5-yl)cyclopenten-1-yl]-4-(methylsulfonyl)benzene;

1-[2-(3-methoxy-2-methylpyridin-5-yl)cyclopenten-1-yl]-4-(methylsulfonyl)benzene;

1-[2-(2,3-difluoropyridin-5-yl)cyclopenten-1-yl]-4-(methylsulfonyl)benzene;

1-[2-(3-methyl-2-fluoropyridin-5-yl)cyclopenten-1-yl]-4-(methylsulfonyl)benzene;

1-[2-(3-chloro-2-fluoropyridin-5-yl)cyclopenten-1-yl]-4-(methylsulfonyl)benzene;

1-[2-(3-trifluoromethyl-2-fluoropyridin-5-yl)cyclopenten-1-yl]-4-(methylsulfonyl)benzene;

1-[2-(3-methoxy-2-fluoropyridin-5-yl)cyclopenten-1-yl]-4-(methylsulfonyl)benzene;

1-[2-(2,3-dichloropyridin-5-yl)cyclopenten-1-yl]-4-(methylsulfonyl)benzene;

1-[2-(3-methyl-2-chloropyridin-5-yl)cyclopenten-1-yl]-4-(methylsulfonyl)benzene;

1-[2-(3-fluoro-2-chloropyridin-5-yl)cyclopenten-1-yl]-4-(methylsulfonyl)benzene;

1-[2-(3-trifluoromethyl-2-chloropyridin-5-yl)cyclopenten-1-yl]-4-(methylsulfonyl)benzene;

1-[2-(3-methoxy-2-chloropyridin-5-yl)cyclopenten-1-yl]-4-(methylsulfonyl)benzene;

1-[2-(2,3-dimethoxypyridin-5-yl)cyclopenten-1-yl]-4-(methylsulfonyl)benzene;

1-[2-(3-methyl-2-methoxypyridin-5-yl)cyclopenten-1-yl]-4-(methylsulfonyl)benzene;

1-[2-(3-fluoro-2-methoxypyridin-5-yl)cyclopenten-1-yl]-4-(methylsulfonyl)benzene;

1-[2-(3-trifluoromethyl-2-methoxypyridin-5-yl)cyclopenten-1-yl]-4-(methylsulfonyl)benzene 1-[2-(3-chloro-2-methoxypyridin-5-yl cyclopenten-1-yl]-4-(methylsulfonyl)benzene;

1-[2-[2,3-di(trifluoromethyl)pyridin-5-yl]cyclopenten-1-yl]-4-(methylsulfonyl)benzene;

1-[2-(3-methyl-2-trifluoromethylpyridin-5-yl)cyclopenten-1-yl]-4-(methylsulfonyl)benzene;

1-[2-(3-fluoro-2-trifluoromethylpyridin-5-yl)cyclopenten-1-yl]-4-(methylsulfonyl)benzene;

1-[2-(3-methoxy-2-trifluoromethylpyridin-5-yl)cyclopenten-1-yl]-4-(methylsulfonyl)benzene;

1-[2-(3-chloro-2-trifluoromethylpyridin-5-yl)cyclopenten-1-yl]-4-(methylsulfonyl)benzene;

1-[2-(3-difluoromethyl-2-methylpyridin-5-yl)cyclopenten-1-yl]-4-(methylsulfonyl)benzene;

1-[2-(3-difluoromethyl-2-fluoropyridin-5-yl)cyclopenten-1-yl]-4-(methylsulfonyl)benzene;

1-[2-(3-difluoromethyl-2-chloropyridin-5-yl)cyclopenten-1-yl]-4-(methylsulfonyl)benzene;

1-[2-(3-difluoromethyl-2-methoxypyridin-5-yl)cyclopenten-1-yl]-4-(methylsulfonyl)benzene 1-[2-[2,3-di(difluoromethyl)pyridin-5-yl]cyclopenten-1-yl]-4-(methylsulfonyl)benzene;

1-[2-(3-methyl-2-difluoromethylpyridin-5-yl)cyclopenten-1-yl]-4-(methylsulfonyl)benzene;

1-[2-(3-fluoro-2-difluoromethylpyridin-5-yl)cyclopenten-1-yl](methylsulfonyl)benzene;

1-[2-(3-methoxy-2-difluoromethylpyridin-5-yl)cyclopenten-1-yl]-4-(methylsulfonyl)benzene;

1-[2-(3-chloro-2-difluoromethylpyridin-5-yl)cyclopenten-1-yl]-4-(methylsulfonyl)benzene;
4-[2-(2,3-dimethylpyridin-5-yl)cyclopenten-1-yl]benzenesulfonamide;
4-[2-(3-fluoro-2-methylpyridin-5-yl)cyclopenten-1-yl]benzenesulfonamide;
4-[2-(3-chloro-2-methylpyridin-5-yl)cyclopenten-1-yl]benzenesulfonamide;
4-[2-(3-trifluoromethyl-2-methylpyridin-5-yl)cyclopenten-1-yl]benzenesulfonamide;
4-[2-(3-methoxy-2-methylpyridin-5-yl)cyclopenten-1-yl]benzenesulfonamide;
4-[2-(2,3-difluoropyridin-5-yl)cyclopenten-1-yl]benzenesulfonamide;
4-[2-(3-methyl-2-fluoropyridin-5-yl)cyclopenten-1-yl]benzenesulfonamide;
4-[2-(3-chloro-2-fluoropyridin-5-yl)cyclopenten-1-yl]benzenesulfonamide;
4-[2-(3-trifluoromethyl-2-fluoropyridin-5-yl)cyclopenten-1-yl]benzenesulfonamide;
4-[2-(3-methoxy-2-fluoropyridin-5-yl)cyclopenten-1-yl]benzenesulfonamide;
4-[2-(2,3-dichloropyridin-5-yl)cyclopenten-1-yl]benzenesulfonamide;
4-[2-(3-methyl-2-chloropyridin-5-yl)cyclopenten-1-yl]benzenesulfonamide;
4-[2-(3-fluoro-2-chloropyridin-5-yl)cyclopenten-1-yl]benzenesulfonamide;
4-[2-(3-trifluoromethyl-2-chloropyridin-5-yl)cyclopenten-1-yl]benzenesulfonamide;
4-[2-(3-methoxy-2-chloropyridin-5-yl)cyclopenten-1-yl]benzenesulfonamide;
4-[2-(2,3-dimethoxypyridin-5-yl)cyclopenten-1-yl]benzenesulfonamide;
4-[2-(3-methyl-2-methoxypyridin-5-yl)cyclopenten-1-yl]benzenesulfonamide;
4-[2-(3-fluoro-2-methoxypyridin-5-yl)cyclopenten-1-yl]benzenesulfonamide;
4-[2-(3-trifluoromethyl-2-methoxypyridin-5-yl)cyclopenten-1-yl]benzenesulfonamide;
4-[2-(3-chloro-2-methoxypyridin-5-yl)cyclopenten-1-yl]benzenesulfonamide;
4-[2-[2,3-di(trifluoromethyl)pyridin-5-yl]cyclopenten-1-yl]benzenesulfonamide;
4-[2-(3-methyl-2-trifluoromethylpyridin-5-yl)cyclopenten-1-yl]benzenesulfonamide;
4-[2-(3-fluoro-2-trifluoromethylpyridin-5-yl)cyclopenten-1-yl]benzenesulfonamide;
4-[2-(3-methoxy-2-trifluoromethylpyridin-5-yl)cyclopenten-1-yl]benzenesulfonamide;
4-[2-(3-chloro-2-trifluoromethylpyridin-5-yl)cyclopenten-1-yl]benzenesulfonamide;
4-[2-(3-difluoromethyl-2-methylpyridin-5-yl)cyclopenten-1-yl]benzenesulfonamide;
4-[2-(3-difluoromethyl-2-fluoropyridin-5-yl)cyclopenten-1-yl]benzenesulfonamide;
4-[2-(3-difluoromethyl-2-chloropyridin-5-yl)cyclopenten-1-yl]benzenesulfonamide;
4-[2-(3-difluoromethyl-2-methoxypyridin-5-yl)cyclopenten-1-yl]benzenesulfonamide;
4-[2-[2,3-di(difluoromethyl)pyridin-5-yl]cyclopenten-1-yl]benzenesulfonamide;
4-[2-(3-methyl-2-difluoromethylpyridin-5-yl)cyclopenten-1-yl]benzenesulfonamide;
4-[2-(3-fluoro-2-difluoromethylpyridin-5-yl)cyclopenten-1-yl]benzenesulfonamide;
4-[2-(3-methoxy-2-difluoromethylpyridin-5-yl)cyclopenten-1-yl]benzenesulfonamide; and
4-[2-(3-chloro-2-difluoromethylpyridin-5-yl)cyclopenten-1-yl]benzenesulfonamide.

24. A compound of Formula VI

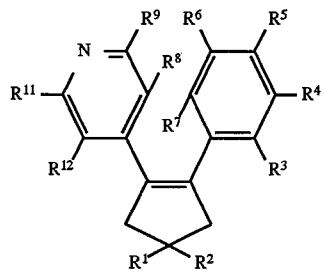

wherein each of $R^1$ and $R^2$ is independently selected from alkyl, hydrido, hydroxyalkyl, halo, haloalkyl, alkoxycarbonyl and carboxyl;

wherein $R^5$ is selected from alkylsulfonyl, haloalkylsulfonyl and sulfamyl; and.

wherein each of $R^3$, $R^4$, $R^6$, $R^7$, $R^8$, $R^9$, $R^{11}$ and $R^{12}$ is independently selected from hydrido, halo, alkyl, alkylthio, cyano, haloalkyl, alkoxy, haloalkoxy, hydroxyalkyl and alkoxyalkyl;

or a pharmaceutically-acceptable salt thereof.

25. The compound of claim 24 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; wherein $R^5$ is selected from methylsulfonyl, ethylsulfonyl, fluoromethylsulfonyl, trifluoromethylsulfonyl and sulfamyl; and wherein each of $R^3$, $R^4$, $R^6$, $R^7$, $R^8$, $R^9$, $R^{11}$ and $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, trifluoromethylsulfonyl and sulfamyl;

or a pharmaceutically-acceptable salt thereof.

26. A compound of Formula II

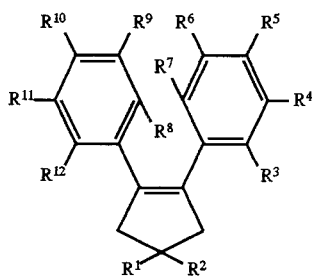

wherein each of R¹ and R² is independently selected from alkyl, hydrido, hydroxyalkyl, halo, haloalkyl, alkoxycarbonyl and carboxyl; and wherein each of R³ through R¹² is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl;

provided that R⁵ cannot be hydrido when R¹⁰ is selected from hydrido, cyano, halo, methyl, trifluoromethyl and methoxy; further provided that R¹⁰ cannot be hydrido when R⁵ is selected from cyano, halo, methyl, trifluoromethyl and methoxy; and further provided that R⁵ and R¹⁰ are not both methoxy; or a pharmaceutically suitable salt thereof.

27. Compound of claim 26 wherein each of R¹ and R² is independently selected from lower alkyl, hydrido, lower hydroxyalkyl, halo, lower haloalkyl, lower alkoxycarbonyl and carboxyl; and wherein each of R³ through R¹² is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl; or a pharmaceutically suitable salt thereof.

28. The compound of claim 27 wherein each of R¹ and R² is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of R³ through R¹² is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, fluoromethylsulfonyl, trifluoromethylsulfonyl and sulfamyl; or a pharmaceutically suitable salt thereof.

29. Compound of claim 28 which is 1-[2-(3-chloro-4-fluorophenyl)cyclopenten-1-yl)-4-(methylsulfonyl)benzene, or a pharmaceutically-acceptable salt thereof.

30. Compound of claim 28 which is 4-[2-(3-chloro-4-fluorophenyl)cyclopenten-1-yl)benzenesulfonamide, or a pharmaceutically-acceptable salt thereof.

31. Compound of claim 28 selected from compounds, and their pharmaceutically-acceptable salts, of the group consisting of 1-[2-(2,3-difluorophenyl)cyclopenten-1-yl]-4-(methylsulfonyl)benzene;
4-[2-(2,3-difluorophenyl)cyclopenten-1-yl]benzenesulfonamide;
1-[2-(4-chlorophenyl)-4,4-dimethylcyclopenten-1-yl]-4-(methylsulfonyl)benzene;
1-[2-(4-fluorophenyl)-4,4-diethylcyclopenten-1-yl]-4-(methylsulfonyl)benzene;
4-[2-(4-fluorophenyl)-4,4-diethylcyclopenten-1-yl]benzenesulfonamide;
4-[2-(4-methoxyphenyl)cyclopenten-1-yl]benzenesulfonamide;
4-[2-(4-chlorophenyl)-4,4-dimethylcyclopenten-1-yl]benzenesulfonamide;
1-[2-(4-fluorophenyl)cyclopenten-1-yl]-4-(fluoromethylsulfonyl)benzene;
1-[2-(4-fluoro-2-methylphenyl)cyclopenten-1-yl]-4-(fluoromethylsulfonyl)benzene;
5-[2-(4-(methylsulfonyl)phenyl]cyclopenten-1-yl]-1,3-benzodioxole;
1-[2-(4-fluorophenyl)-4,4-di(fluoromethyl)cyclopenten-1-yl]-4-(methylsulfonyl)benzene;
1-[2-(4-fluorophenyl)-4,4-di(trifluoromethyl)cyclopenten-1-yl]-4-(methylsulfonyl)benzene;
4-[2-(4-trifluoromethylphenyl)-4-carboxycyclopenten-1-yl]benzenesulfonamide;
1-[2-(3,4-dimethylphenyl)cyclopenten-1-yl]-4-(methylsulfonyl)benzene;
1-[2-(3-fluoro-4-methylphenyl)cyclopenten-1-yl]-4-(methylsulfonyl)benzene;
1-[2-(3-chloro-4-methylphenyl)cyclopenten-1-yl]-4-(methylsulfonyl)benzene;
1-[2-(3-trifluoromethyl-4-methylphenyl)cyclopenten-1-yl]-4-(methylsulfonyl)benzene;
1-[2-(3-methoxy-4-methylphenyl)cyclopenten-1-yl]-4-(methylsulfonyl)benzene;
1-[2-(3,4-difluorophenyl)cyclopenten-1-yl]-4-(methylsulfonyl)benzene;
1-[2-(3-methyl-4-fluorophenyl)cyclopenten-1-yl]-4-(methylsulfonyl)benzene;
1-[2-(3-chloro-4-fluorophenyl)cyclopenten-1-yl]-4-(methylsulfonyl)benzene;
1-[2-(3-trifluoromethyl-4-fluorophenyl)cyclopenten-1-yl]-4-(methylsulfonyl)benzene;
1-[2-(3-methoxy-4-fluorophenyl)cyclopenten-1-yl]-4-(methylsulfonyl)benzene;
1-[2-(3,4-dichlorophenyl)cyclopenten-1-yl]-4-(methylsulfonyl)benzene;
1-[2-(3-methyl-4-chlorophenyl)cyclopenten-1-yl](methylsulfonyl)benzene;
1-[2-(3-fluoro-4-chlorophenyl)cyclopenten-1-yl]-4-(methylsulfonyl)benzene
1-[2-(3-trifluoromethyl-4-chlorophenyl)cyclopenten-1-yl]-4-(methylsulfonyl)benzene;
1-[2-(3-methoxy-4-chlorophenyl)cyclopenten-1-yl]-4-(methylsulfonyl)benzene;
1-[2-(3,4-methoxyphenyl)cyclopenten-1-yl]-4-(methylsulfonyl)benzene;
1-[2-(3-methyl-4-methoxyphenyl)cyclopenten-1-yl]-4-(methylsulfonyl)benzene;
1-[2-(3-fluoro-4-methoxyphenyl)cyclopenten-1-yl]-4-(methylsulfonyl)benzene;
1-[2-(3-trifluoromethyl-4-methoxyphenyl)cyclopenten-1-yl]-4-(methylsulfonyl)benzene;
1-[2-(3-chloro-4-methoxyphenyl)cyclopenten-1-yl]-4-(methylsulfonyl)benzene;

1-[2-[3,4-di(trifluoromethyl)phenyl]cyclopenten-1-yl]-4-(methylsulfonyl)benzene;
1-[2-(3-methyl-4-trifluoromethylphenyl)cyclopenten-1-yl]-4-(methylsulfonyl)benzene;
1-[2-(3-fluoro-4-trifluoromethylphenyl)cyclopenten-1-yl]-4-(methylsulfonyl)benzene;
1-[2-(3-methoxy-4-trifluoromethylphenyl)cyclopenten-1-yl]-4-(methylsulfonyl)benzene;
1-[2-(3-chloro-4-trifluoromethylphenyl)cyclopenten-1-yl]-4-(methylsulfonyl)benzene;
1-[2-(3-difluoromethyl-4-methylphenyl)cyclopenten-1-yl]-4-(methylsulfonyl)benzene;
1-[2-(3-difluoromethyl-4-fluorophenyl)cyclopenten-1-yl]-4-(methylsulfonyl)benzene;
1-[2-(3-difluoromethyl-4-chlorophenyl)cyclopenten-1-yl]-4-(methylsulfonyl)benzene;
1-[2-(3-difluoromethyl-4-methoxyphenyl)cyclopenten-1-yl]-4-(methylsulfonyl)benzene;
1-[2-[3,4-di(difluoromethyl)phenyl]cyclopenten-1-yl]-4-(methylsulfonyl)benzene;
1-[2-(3-methyl-4-difluoromethylphenyl)cyclopenten-1-yl]-4-(methylsulfonyl)benzene;
1-[2-(3-fluoro-4-difluoromethylphenyl)cyclopenten-1-yl]-4-(methylsulfonyl)benzene;
1-[2-(3-methoxy-4-difluoromethylphenyl)cyclopenten-1-yl]-4-(methylsulfonyl)benzene;
1-[2-(3-chloro-4-difluoromethylphenyl)cyclopenten-1-yl]-4-(methylsulfonyl)benzene;
4-[2-(4-methylthiophenyl)cyclopenten-1-yl]benzenesulfonamide;
4-[2-(4-cyanophenyl)cyclopenten-1-yl]benzenesulfonamide;
4-[2-(4-hydroxymethylphenyl)cyclopenten-1-yl]benzenesulfonamide;
4-[2-(4-methoxymethylphenyl)cyclopenten-1-yl]benzenesulfonamide;
4-[2-(4-fluoro-2-methylphenyl)cyclopenten-1-yl]benzenesulfonamide;
4-[2-(4-fluorophenyl)-4,4-di(fluoromethyl)cyclopenten-1-yl]benzenesulfonamide;
4-[2-(4-fluorophenyl)-4,4-di(trifluoromethyl)cyclopenten-1-yl]benzenesulfonamide;
5-[2-(4-(aminosulfonyl)phenyl]cyclopenten-1-yl]-1,3-benzodioxole;
4-[2-(3,4-dimethylphenyl)cyclopenten-1-yl]benzenesulfonamide;
4-[2-(3-fluoro-4-methylphenyl)cyclopenten-1-yl]benzenesulfonamide;
4-[2-(3-chloro-4-methylphenyl)cyclopenten-1-yl]benzenesulfonamide;
4-[2-(3-trifluoromethyl-4-methylphenyl)cyclopenten-1-yl]benzenesulfonamide;
4-[2-(3-methoxy-4-methylphenyl)cyclopenten-1-yl]benzenesulfonamide;
4-[2-phenylcyclopenten-1-yl]benzenesulfonamide;
4-[2-(3,4-difluorophenyl)cyclopenten-1-yl]benzenesulfonamide;
4-[2-(3-methyl-4-fluorophenyl)cyclopenten-1-yl]benzenesulfonamide;
4-[2-(3-chloro-4-fluorophenyl)cyclopenten-1-yl]benzenesulfonamide;
4-[2-(3-trifluoromethyl-4-fluorophenyl)cyclopenten-1-yl]benzenesulfonamide;
4-[2-(3-methoxy-4-fluorophenyl)cyclopenten-1-yl]benzenesulfonamide;
4-[2-(3,4-dichlorophenyl)cyclopenten-1-yl]benzenesulfonamide;
4-[2-(3-methyl-4-chlorophenyl)cyclopenten-1-yl]benzenesulfonamide;
4-[2-(3-fluoro-4-chlorophenyl)cyclopenten-1-yl]benzenesulfonamide;
4-[2-(3-trifluoromethyl-4-chlorophenyl)cyclopenten-1-yl]benzenesulfonamide;
4-[2-(3-methoxy-4-chlorophenyl)cyclopenten-1-yl]benzenesulfonamide;
4-[2-(3,4-methoxyphenyl)cyclopenten-1-yl]benzenesulfonamide;
4-[2-(3-methyl-4-methoxyphenyl)cyclopenten-1-yl]benzenesulfonamide;
4-[2-(3-fluoro-4-methoxyphenyl)cyclopenten-1-yl]benzenesulfonamide;
4-[2-(3-trifluoromethyl-4-methoxyphenyl)cyclopenten-1-yl]benzenesulfonamide;
4-[2-(3-chloro-4-methoxyphenyl)cyclopenten-1-yl]benzenesulfonamide;
4-[2-[3,4-di(trifluoromethyl)phenyl]cyclopenten-1-yl]benzenesulfonamide;
4-[2-(3-methyl-4-trifluoromethylphenyl)cyclopenten-1-yl]benzenesulfonamide,
4-[2-(3-fluoro-4-trifluoromethylphenyl)cyclopenten-1-yl]benzenesulfonamide
4-[2-(3-methoxy-4-trifluoromethylphenyl)cyclopenten-1-yl]benzenesulfonamide
4-[2-(3-chloro-4-trifluoromethylphenyl)cyclopenten-1-yl]benzenesulfonamide
4-[2-(3-difluoromethyl-4-methylphenyl)cyclopenten-1-yl]benzenesulfonamide
4-[2-(3-difluoromethyl-4-fluorophenyl)cyclopenten-1-yl]benzenesulfonamide
4-[2-(3-difluoromethyl-4-chlorophenyl)cyclopenten-1-yl]benzenesulfonamide;
4-[2-(3-difluoromethyl-4-methoxyphenyl)cyclopenten-1-yl]benzenesulfonamide;
4-[2-[3,4-di(difluoromethyl)phenyl]cyclopenten-1-yl]benzenesulfonamide;
4-[2-(3-methyl-4-difluoromethylphenyl)cyclopenten-1-yl]benzenesulfonamide;
4-[2-(3-fluoro-4-difluoromethylphenyl)cyclopenten-1-yl]benzenesulfonamide;
4-[2-(3-methoxy-4-difluoromethylphenyl)cyclopenten-1-yl]benzenesulfonamide; and
4-[2-(3-chloro-4-difluoromethylphenyl)cyclopenten-1-yl]benzenesulfonamide.

32. A pharmaceutical composition comprising a therapeutically-effective amount of Formula II

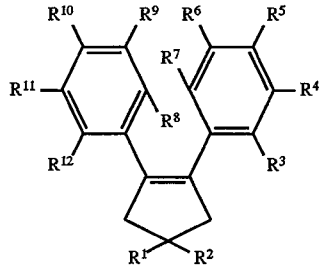

wherein each of $R^1$ and $R^2$ is independently selected from alkyl, hydrido, hydroxyalkyl, halo, haloalkyl, alkoxycarbonyl and carboxyl; and wherein each of $R^3$ through $R^{12}$ is independently selected from hydrido, halo, alkyl, alkylthio, cyano, haloalkyl, alkoxy, haloalkoxy, hydroxyalkyl, alkoxyalkyl, alkylsulfonyl, haloalkylsulfonyl and sulfamyl; or a pharmaceutically suitable salt thereof.

33. A pharmaceutical composition of claim 32 wherein each of $R^1$ and $R^2$ is independently selected from lower alkyl, hydrido, lower hydroxyalkyl, halo, lower haloalkyl, lower alkoxycarbonyl and carboxyl; and wherein each of $R^3$ through $R^{12}$ is independently selected from hydrido, halo, lower alkyl, lower alkylthio, cyano, lower haloalkyl, lower alkoxy, lower haloalkoxy, lower hydroxyalkyl, lower alkoxyalkyl, lower alkylsulfonyl, lower haloalkylsulfonyl and sulfamyl; or a pharmaceutically suitable salt thereof.

34. A pharmaceutical composition of claim 33 wherein each of $R^1$ and $R^2$ is independently selected from hydrido, methyl, ethyl, propyl, butyl, pentyl, isopropyl, isobutyl, tert-butyl, pentyl, hexyl, hydroxymethyl, fluoro, chloro, bromo, iodo, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxycarbonyl, ethoxycarbonyl, isopropoxycarbonyl, tertbutoxycarbonyl, propoxycarbonyl, butoxycarbonyl, isobutoxycarbonyl, pentoxycarbonyl and carboxyl; and wherein each of $R^3$ through $R^{12}$ is independently selected from hydrido, fluoro, chloro, bromo, iodo, methyl, ethyl, propyl, butyl, pentyl, isopropyl, isobutyl, tert-butyl, pentyl, hexyl, methylthio, cyano, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, propoxy, butoxy, isopropoxy, tert-butoxy, methylenedioxy, trifluoromethoxy, hydroxymethyl, methoxymethyl, ethoxymethyl, isopropoxymethyl, tert-butoxymethyl, propoxyethyl, butoxymethyl, isobutoxymethyl, pentoxymethyl, methylsulfonyl, ethylsulfonyl, fluoromethylsulfonyl, trifluoromethylsulfonyl and sulfamyl; or a pharmaceutically suitable salt thereof.

35. The pharmaceutical composition of claim 34 wherein said compound is 1-[2-(3-chloro-4-fluorophenyl) cyclopenten-1-yl)-4-(methylsulfonyl)benzene, or a pharmaceutically-acceptable salt thereof.

36. The pharmaceutical composition of claim 34 wherein said compound is 4-[2-(3-chloro-4-fluorophenyl) cyclopenten-1-yl)benzenesulfonamide, or a pharmaceutically-acceptable salt thereof.

37. A pharmaceutical composition of claim 34 wherein compounds, and their pharmaceutically-acceptable salts, of the group consisting of 1-[2-(2,3-difluorophenyl)cyclopenten-1-yl]-4-(methylsulfonyl)benzene;

4-[2-(2,3-difluorophenyl)cyclopenten-1-yl] benzenesulfonamide;

1-[2-(4-chlorophenyl)-4,4-dimethylcyclopenten-1-yl]-4-(methylsulfonyl)benzene;

1-[2-(4-fluorophenyl)-4,4-diethylcyclopenten-1-yl]-4-(methylsulfonyl)benzene;

4-[2-(4-fluorophenyl)-4,4-diethylcyclopenten-1-yl] benzenesulfonamide;

4-[2-(4-methoxyphenyl)cyclopenten-1-yl] benzenesulfonamide;

4-[2-(4-chlorophenyl)-4,4-dimethylcyclopenten-1-yl] benzenesulfonamide;

1-[2-(4-fluorophenyl)cyclopenten-1-yl]-4-(fluoromethylsulfonyl)benzene;

1-[2-(4-fluoro-2-methylphenyl)cyclopenten-1-yl]-4-(fluoromethylsulfonyl)benzene;

5-[2-(4-(methylsulfonyl)phenyl]cyclopenten-1-yl]-1,3-benzodioxole;

1-[2-(4-fluorophenyl)-4,4-di(fluoromethyl)cyclopenten-1-yl]-4-(methylsulfonyl)benzene;

1-[2-(4-fluorophenyl)-4,4-di(trifluoromethyl)cyclopenten-1-yl]-4-(methylsulfonyl)benzene;

4-[2-(4-trifluoromethylphenyl)-4-carboxycyclopenten-1-yl]benzenesulfonamide;

1-[2-(3,4-dimethylphenyl)cyclopenten-1-yl]-4-(methylsulfonyl)benzene;

1-[2-(3-fluoro-4-methylphenyl)cyclopenten-1-yl]-4-(methylsulfonyl)benzene;

1-[2-(3-chloro-4-methylphenyl)cyclopenten-1-yl]-4-(methylsulfonyl)benzene;

1-[2-(3-trifluoromethyl-4-methylphenyl)cyclopenten-1-yl]-4-(methylsulfonyl)benzene;

1-[2-(3-methoxy-4-methylphenyl)cyclopenten-1-yl]-4-(methylsulfonyl)benzene;

1-[2-(3,4-difluorophenyl)cyclopenten-1-yl]-4-(methylsulfonyl)benzene;

1-[2-(3-methyl-4-fluorophenyl)cyclopenten-1-yl]-4-(methylsulfonyl)benzene;

1-[2-(3-chloro-4-fluorophenyl)cyclopenten-1-yl]-4-(methylsulfonyl)benzene;

1-[2-(3-trifluoromethyl-4-fluorophenyl)cyclopenten-1-yl]-4-(methylsulfonyl)benzene;

1-[2-(3-methoxy-4-fluorophenyl)cyclopenten-1-yl]-4-(methylsulfonyl)benzene;

1-[2-(3,4-dichlorophenyl)cyclopenten-1-yl]-4-(methylsulfonyl)benzene;

1-[2-(3-methyl-4-chlorophenyl)cyclopenten-1-yl]-4-(methylsulfonyl)benzene;

1-[2-(3-fluoro-4-chlorophenyl)cyclopenten-1-yl]-4-(methylsulfonyl)benzene

1-[2-(3-trifluoromethyl-4-chlorophenyl)cyclopenten-1-yl] (methylsulfonyl)benzene;

1-[2-(3-methoxy-4-chlorophenyl)cyclopenten-1-yl] (methylsulfonyl)benzene;

1-[2-(3,4-methoxyphenyl)cyclopenten-1-yl]-4-(methylsulfonyl)benzene;

1-[2-(3-methyl-4-methoxyphenyl)cyclopenten-1-yl]-4-(methylsulfonyl)benzene;

1-[2-(3-fluoro-4-methoxyphenyl)cyclopenten-1-yl]-4-(methylsulfonyl)benzene;

1-[2-(3-trifluoromethyl-4-methoxyphenyl)cyclopenten-1-yl]-4-(methylsulfonyl)benzene;

1-[2-(3-chloro-4-methoxyphenyl)cyclopenten-1-yl]-4-(methylsulfonyl)benzene;

1-[2-[3,4-di(trifluoromethyl)phenyl]cyclopenten-1-yl]-4-(methylsulfonyl)benzene;

1-[2-(3-methyl-4-trifluoromethylphenyl)cyclopenten-1-yl]-4-(methylsulfonyl)benzene;

1-[2-(3-fluoro-4-trifluoromethylphenyl)cyclopenten-1-yl]-4-(methylsulfonyl)benzene;

1-[2-(3-methoxy-4-trifluoromethylphenyl)cyclopenten-1-yl]-4-(methylsulfonyl)benzene;

1-[2-(3-chloro-4-trifluoromethylphenyl)cyclopenten-1-yl]-4-(methylsulfonyl)benzene;

1-[2-(3-difluoromethyl-4-methylphenyl)cyclopenten-1-yl]-4-(methylsulfonyl)benzene;

1-[2-(3-difluoromethyl-4-fluorophenyl)cyclopenten-1-yl]-4-(methylsulfonyl)benzene;

1-[2-(3-difluoromethyl-4-chlorophenyl)cyclopenten-1-yl]-4-(methylsulfonyl)benzene;

1-[2-(3-difluoromethyl-4-methoxyphenyl)cyclopenten-1-yl]-4-(methylsulfonyl)benzene;

1-[2-[3,4-di(difluoromethyl)phenyl]cyclopenten-1-yl]-4-(methylsulfonyl)benzene;

1-[2-(3-methyl-4-difluoromethylphenyl)cyclopenten-1-yl]-4-(methylsulfonyl)benzene;

1-[2-(3-fluoro-4-difluoromethylphenyl)cyclopenten-1-yl]-4-(methylsulfonyl)benzene;
1-[2-(3-methoxy-4-difluoromethylphenyl)cyclopenten-1-yl]-4-(methylsulfonyl)benzene;
1-[2-(3-chloro-4-difluoromethylphenyl)cyclopenten-1-yl]-4-(methylsulfonyl)benzene;
4-[2-(4-methylthiophenyl)cyclopenten-1-yl]benzenesulfonamide;
4-[2-(4-cyanophenyl)cyclopenten-1-yl]benzenesulfonamide;
4-[2-(4-hydroxymethylphenyl)cyclopenten-1-yl]benzenesulfonamide;
4-[2-(4-methoxymethylphenyl)cyclopenten-1-yl]benzenesulfonamide;
4-[2-(4-fluoro-2-methylphenyl)cyclopenten-1-yl]benzenesulfonamide;
4-[2-(4-fluorophenyl)-4,4-di(fluoromethyl)cyclopenten-1-yl]benzenesulfonamide;
4-[2-(4-fluorophenyl)-4,4-di(trifluoromethyl)cyclopenten-1-yl]benzenesulfonamide;
5-[2-(4-(aminosulfonyl)phenyl]cyclopenten-1-yl]-1,3-benzodioxole;
4-[2-(3,4-dimethylphenyl)cyclopenten-1-yl]benzenesulfonamide;
4-[2-(3-fluoro-4-methylphenyl)cyclopenten-1-yl]benzenesulfonamide;
4-[2-(3-chloro-4-methylphenyl)cyclopenten-1-yl]benzenesulfonamide;
4-[2-(3-trifluoromethyl-4-methylphenyl)cyclopenten-1-yl]benzenesulfonamide;
4-[2-(3-methoxy-4-methylphenyl)cyclopenten-1-yl]benzenesulfonamide;
4-[2-phenylcyclopenten-1-yl]benzenesulfonamide;
4-[2-(3,4-difluorophenyl)cyclopenten-1-yl]benzenesulfonamide;
4-[2-(3-methyl-4-fluorophenyl)cyclopenten-1-yl]benzenesulfonamide;
4-[2-(3-chloro-4-fluorophenyl)cyclopenten-1-yl]benzenesulfonamide;
4-[2-(3-trifluoromethyl-4-fluorophenyl)cyclopenten-1-yl]benzenesulfonamide;
4-[2-(3-methoxy-4-fluorophenyl)cyclopenten-1-yl]benzenesulfonamide;
4-[2-(3,4-dichlorophenyl)cyclopenten-1-yl]benzenesulfonamide;
4-[2-(3-methyl-4-chlorophenyl)cyclopenten-1-yl]benzenesulfonamide;
4-[2-(3-fluoro-4-chlorophenyl)cyclopenten-1-yl]benzenesulfonamide;
4-[2-(3-trifluoromethyl-4-chlorophenyl)cyclopenten-1-yl]benzenesulfonamide;
4-[2-(3-methoxy-4-chlorophenyl)cyclopenten-1-yl]benzenesulfonamide;
4-[2-(3,4-methoxyphenyl)cyclopenten-1-yl]benzenesulfonamide;
4-[2-(3-methyl-4-methoxyphenyl)cyclopenten-1-yl]benzenesulfonamide;
4-[2-(3-fluoro-4-methoxyphenyl)cyclopenten-1-yl]benzenesulfonamide;
4-[2-(3-trifluoromethyl-4-methoxyphenyl)cyclopenten-1-yl]benzenesulfonamide;
4-[2-(3-chloro-4-methoxyphenyl)cyclopenten-1-yl]benzenesulfonamide;
4-[2-[3,4-di(trifluoromethyl)phenyl]cyclopenten-1-yl]benzenesulfonamide;
4-[2-(3-methyl-4-trifluoromethylphenyl)cyclopenten-1-yl]benzenesulfonamide;
4-[2-(3-fluoro-4-trifluoromethylphenyl)cyclopenten-1-yl]benzenesulfonamide;
4-[2-(3-methoxy-4-trifluoromethylphenyl)cyclopenten-1-yl]benzenesulfonamide;
4-[2-(3-chloro-4-trifluoromethylphenyl)cyclopenten-1-yl]benzenesulfonamide;
4-[2-(3-difluoromethyl-4-methylphenyl)cyclopenten-1-yl]benzenesulfonamide;
4-[2-(3-difluoromethyl-4-fluorophenyl)cyclopenten-1-yl]benzenesulfonamide;
4-[2-(3-difluoromethyl-4-chlorophenyl)cyclopenten-1-yl]benzenesulfonamide;
4-[2-(3-difluoromethyl-4-methoxyphenyl)cyclopenten-1-yl]benzenesulfonamide;
4-[2-[3,4-di(difluoromethyl)phenyl]cyclopenten-1-yl]benzenesulfonamide;
4-[2-(3-methyl-4-difluoromethylphenyl)cyclopenten-1-yl]benzenesulfonamide;
4-[2-(3-fluoro-4-difluoromethylphenyl)cyclopenten-1-yl]benzenesulfonamide;
4-[2-(3-methoxy-4-difluoromethylphenyl)cyclopenten-1-yl]benzenesulfonamide; and
4-[2-(3-chloro-4-difluoromethylphenyl)cyclopenten-1-yl]benzenesulfonamide.

* * * * *